(12) United States Patent
Peng et al.

(10) Patent No.: US 8,227,621 B2
(45) Date of Patent: Jul. 24, 2012

(54) CYANINE DYES AND METHODS OF USE

(75) Inventors: Xinzhan Peng, Lincoln, NE (US); Xinshe Xu, Lincoln, NE (US); Daniel R. Draney, Lincoln, NE (US); Garrick M. Little, Lincoln, NE (US); Jiyan Chen, Lincoln, NE (US); William M. Volcheck, Lincoln, NE (US); Charles Prescott, Lincoln, NE (US)

(73) Assignee: Li-Cor, Inc., Lincoln, NE (US)

( * ) Notice: Subject to any disclaimer, the term of this patent is extended or adjusted under 35 U.S.C. 154(b) by 594 days.

(21) Appl. No.: 11/423,675

(22) Filed: Jun. 12, 2006

(65) Prior Publication Data

US 2007/0042398 A1    Feb. 22, 2007

Related U.S. Application Data

(60) Provisional application No. 60/762,910, filed on Jan. 25, 2006, provisional application No. 60/696,207, filed on Jun. 30, 2005.

(51) Int. Cl.
*C07D 209/56* (2006.01)
*A61B 5/00* (2006.01)

(52) U.S. Cl. .......................................... 548/427; 424/9.6

(58) Field of Classification Search .................. 548/427; 424/9.6
See application file for complete search history.

(56) References Cited

U.S. PATENT DOCUMENTS

| | | | |
|---|---|---|---|
| 4,871,656 A | 10/1989 | Parton et al. | |
| 5,106,990 A * | 4/1992 | Ohno et al. | 548/427 |
| 5,107,063 A * | 4/1992 | West et al. | 548/455 |
| 5,268,486 A | 12/1993 | Waggoner et al. | |
| 5,519,145 A | 5/1996 | Fabricius et al. | |
| 5,556,959 A | 9/1996 | Brush et al. | |
| 5,571,388 A * | 11/1996 | Patonay et al. | 204/461 |
| 5,719,031 A | 2/1998 | Haugland et al. | |
| 6,027,709 A * | 2/2000 | Little et al. | 424/1.65 |
| 6,037,137 A | 3/2000 | Komoriya et al. | |
| 6,083,486 A | 7/2000 | Weissleder et al. | |
| 6,136,612 A | 10/2000 | Della Ciana et al. | |
| 6,180,085 B1 | 1/2001 | Achileful et al. | |
| 6,258,340 B1 | 7/2001 | Licha et al. | |
| 6,287,662 B1 | 9/2001 | Takagishi et al. | |
| 6,287,774 B1 | 9/2001 | Nikiforov | |
| 6,291,201 B1 | 9/2001 | Garman | |
| 6,472,141 B2 | 10/2002 | Nikiforov | |
| 6,534,041 B1 | 3/2003 | Licha et al. | |
| 6,592,847 B1 | 7/2003 | Weissleder et al. | |
| 6,641,798 B2 | 11/2003 | Achilefu et al. | |
| 6,642,375 B2 | 11/2003 | Inomata et al. | |
| 6,649,335 B2 | 11/2003 | Missfeldt | |
| 6,673,334 B1 | 1/2004 | Achilefu et al. | |
| 6,716,509 B2 * | 4/2004 | Yeh et al. | 428/64.1 |
| 6,716,994 B1 | 4/2004 | Menchen et al. | |
| 6,743,640 B2 | 6/2004 | Whitten | |
| 6,747,159 B2 | 6/2004 | Caputo et al. | |
| 6,761,878 B2 | 7/2004 | Achilefu et al. | |
| 6,787,329 B1 | 9/2004 | Wei et al. | |
| 6,828,116 B1 * | 12/2004 | Hamilton et al. | 435/23 |
| 6,893,868 B2 | 5/2005 | Packard et al. | |
| 6,949,635 B1 | 9/2005 | Kumar et al. | |
| 6,995,274 B2 * | 2/2006 | Lugade et al. | 548/427 |
| 7,172,907 B2 | 2/2007 | Chen et al. | |
| 7,230,117 B2 * | 6/2007 | Michael et al. | 548/414 |
| 7,271,265 B2 * | 9/2007 | Haugland et al. | 546/277.4 |
| 7,504,089 B2 * | 3/2009 | Lugade et al. | 424/9.6 |
| 7,547,721 B1 * | 6/2009 | Miwa et al. | 514/414 |
| 2002/0022004 A1 | 2/2002 | Licha et al. | |
| 2002/0034766 A1 | 3/2002 | Huang | |
| 2002/0065421 A1 * | 5/2002 | Caputo et al. | 548/427 |
| 2003/0232999 A1 * | 12/2003 | Sasaki et al. | 548/402 |
| 2004/0014981 A1 | 1/2004 | Lugade et al. | |
| 2004/0058406 A1 | 3/2004 | Nikiforov | |
| 2004/0186275 A1 | 9/2004 | Olson et al. | |
| 2005/0119490 A1 * | 6/2005 | Kawakami | 548/427 |
| 2005/0214833 A1 * | 9/2005 | Carter et al. | 548/455 |
| 2005/0226815 A1 | 10/2005 | Kawakami et al. | |
| 2005/0281741 A1 | 12/2005 | Achilefu et al. | |
| 2006/0223076 A1 * | 10/2006 | Diwu et al. | 435/6 |
| 2007/0021621 A1 | 1/2007 | Reddington | |
| 2007/0090331 A1 | 4/2007 | Seo et al. | |
| 2007/0232805 A1 | 10/2007 | Leung et al. | |

FOREIGN PATENT DOCUMENTS

| | | |
|---|---|---|
| CA | 2145405 | 2/1995 |
| EP | 0 428 000 A1 | 5/1991 |
| EP | 580145 | 1/1994 |
| JP | 01-303433 | * 12/1989 |
| JP | 6-145539 | 5/1994 |
| JP | 09-124599 | * 5/1997 |
| WO | WO 97/13810 A1 | 4/1997 |
| WO | WO 99/05221 A1 | 2/1999 |
| WO | WO 99/64519 A1 | 12/1999 |
| WO | WO 00/16810 A1 | 3/2000 |
| WO | WO 03/106703 A2 | 12/2003 |
| WO | WO 2005/082423 | * 9/2005 |
| WO | WO 2007/028118 A2 | 3/2007 |
| WO | WO 2007/088129 A2 | 8/2007 |

OTHER PUBLICATIONS

Vasilenko et al., Chemical Abstracts, 105:171673, 1986.*
Machine translation of JP 09-124599, May 13, 1997.*
McIntyre, Jonathan C. et al., "Fluorescence Assay for Phospholipid Membrane Asymmetry", Biochemistry, 30, 11819-11827, 1991.*
Mujumdar, et al., "Cyanine Dye Labeling Reagents Containing Isothiocyanate Groups", *Cytometry* 10(11-19) 1989; Pittsburgh, PA.
International Search Report mailed on Jul. 30, 2007, for PCT Application No. PCT/US2006/023231 filed on Jun. 13, 2006, six pages.
Narayanan, N., et al.; A New Method for the Synthesis of Heptamethine Cyanine Dyes: Synthesis of New Near Infrared Fluorescent Labels; Journal of Organic Chemistry, American Chemical Society; 1995, pp. 2391-2395, vol. 60, XP 002065376, ISSN: 0022-3263.

* cited by examiner

*Primary Examiner* — Rebecca Anderson
(74) *Attorney, Agent, or Firm* — Kilpatrick Townsend & Stockton LLP

(57) ABSTRACT

The present invention provides for cyanine dyes as near IR quenchers. The cyanine dyes have absorption wavelengths in the near-infrared region of about 650-900 nm and are essentially non-fluorescent. The dyes of the invention have at least one linking group. The present invention also provides substantially non-fluorescent, NIR probes. Biological assays based on these novel, substantially non-fluorescent, NIR probes are also provided.

17 Claims, 34 Drawing Sheets

Where D: a reporter dye
X: a quencher (X/D is a FRET pair)
P: a phosphate group
M: a transition metal ion

C

| Solvent | Extnctn. Coeff. $M^{-1} cm^{-1}$ | Abs Max nm | Em Max nm | Stokes Shift nm | MW gm/mole |
|---|---|---|---|---|---|
| Methanol | 300,000 | 770 | 786 | 16 | 961 |
| Water | 200,000 | 767 | 786 | 19 | 961 |
| 1X PBS | 200,000 | 767 | 786 | 19 | 961 |
| PBS:Methanol | 270,000 | 770 | 786 | 16 | 961 |

A
BACE1 Inhibitor III (Calbiochem): Statine-derived peptide inhibitor, H-Glu-Val-Asn-Statine-Val-Ala-Glu-Phe-NH2.

| Substrate Conc. (nM) | 200 | 200 | 200 | 200 | 200 | 200 | 200 | 200 | 200 | 200 | 200 | 200 | 200 |
|---|---|---|---|---|---|---|---|---|---|---|---|---|---|
| BACE1 Conc. (nM) | 100 | 100 | 100 | 100 | 100 | 100 | 100 | 100 | 100 | 100 | 100 | 100 | 0 |
| Inhibitor Conc. (nM) | 2500 | 1250 | 625 | 312 | 156 | 78.1 | 39.1 | 19.6 | 9.80 | 4.90 | 2.45 | 0 | 0 |

B

| Parameter | Estimate | ApproxStdErr | Lower CL | Upper CL |
|---|---|---|---|---|
| a | 22.764780788 | 0.98208544 | 20.7962102 | 25.1775578 |
| b | 1.0067569216 | 0.22494136 | 0.623962 | |
| c | 56.631670808 | 13.5658502 | 33.9743877 | 96.4302438 |
| d | 4.5513504932 | 1.14295032 | 1.29855541 | 6.48701996 |

# CYANINE DYES AND METHODS OF USE

CROSS-REFERENCE TO RELATED APPLICATIONS

The present application claims priority to U.S. Provisional Application Nos. 60/696,207 and 60/762,910, filed on Jun. 30, 2005 and Jan. 25, 2006, respectively. The disclosures of which are hereby incorporated by reference in their entireties for all purposes.

BACKGROUND OF THE INVENTION

Near infrared (NIR) fluorescent dyes and biological probes using NIR labeled biomolecules or ligands have become important in biological systems due to their advantages over UV and visible fluorophores. As a result, the number of near-IR (NIR) fluorophores useful for biological systems has grown substantially in recent years. These long-wavelength fluorophores include for example, cyanine, oxazine, rhodamine, and phthalocyanine dyes.

Dyes that fluoresce in the NIR region can serve as a reporting group when tagged to biomolecules. One advantage of using NIR fluorescence technology is the almost complete elimination of background from autofluorescence of biomolecules. Another benefit to near-IR fluorescent technology is that the background from the scattered light from the excitation source is greatly reduced since the scattering intensity is proportional to the inverse fourth power of the wavelength. Low background fluorescence is necessary for highly sensitive detection. Furthermore, the optically transparent window in the near-IR region (650 nm to 900 nm) in biological tissue makes NIR fluorescence a valuable technology for in vivo imaging and subcellular detection applications that require the transmission of light through biological components.

Another attraction of NIR fluorescence for biological applications is the availability and low cost of long-wavelength diode lasers for excitation and high efficiency silicon avalanche photodiodes for detection. However, commercial diode lasers are only available at a limited number of discrete wavelengths. To achieve optimum excitation, a fluorophore's maximum absorption wavelength should match the laser wavelength.

Cyanine dyes have been widely used for labeling biomolecules, e.g. antibodies, DNA probes, avidin, streptavidin, lipids, biochemical analogs, peptide, drug for a variety of applications such as DNA sequencing, DNA microarray, western blotting, flow cytometry analysis, protein microarray. See, for example, U.S. Patent Application No. 20040014981 to Lugade, et al. published Jan. 22, 2004, and U.S. Pat. No. 5,268,486, incorporated herein by reference, for exemplary cyanine dyes. Scientists favor using cyanine dyes in biological applications because, among other reasons, cyanine dyes 1) are biocompatible; 2) have high molar absorptivity (c.a. $10^5$ $M^{-1}$ $cm^{-1}$); 3) are readily modified to match a wide range of desired excitation and detection wavelengths (e.g. about 500 to about 900 nm); 4) are capable of incorporating water-soluble groups and linking groups; 5) and possess favorable fluorescence properties.

In certain applications, for example, detection of enzyme activity, screening of potential inhibitors in high throughput applications, detection of ligand-receptor interactions, and nucleic acid hybridizations, it is desirable to "quench" the fluorescence of the biomolecule or ligand. In order to monitor the biological process, the modulation of the fluorescence becomes important.

In one aspect, the modulation of fluorescence in a biomolecule can be achieved by, for example, labeling the biomolecule with a sufficient number of fluorescent dyes to an extent that the dyes are sufficiently quenched in the biomolecule, that the biomolecule is a substantially non-fluorescent substrate. Haughland, R. P. et al. (U.S. Pat. No. 5,719,031) describe polymers that are labeled with multiple borapolyaza-s-indacene fluorescent dyes (BODIPY) to the point such that fluorescence quenching occurs. Haughland R. P. et al. further describe that the degradation of the labeled polymer results in fluorescence enhancement and that the resulting fluorescence enhancement is useful for measuring the degradation of such polymers, for example, as a result of enzymatic hydrolysis of a protein, carbohydrate, nucleic acid, or other natural or synthetic polymer.

Assays for the detection of protease enzyme activity based on the self-quenching of fluorescence of visible fluorophores located on a small protein, e.g., casein or bovine serum albumin (BSA), have been described by various researchers. Commercial assay kits using this technology exist (Jones, L. J., et al., *Analytical Biochemistry*, 251, 144-152 (1997); Boonacker, E., et al., *The Journal of Histochemistry & Cytochemistry*, 49 (12), 1473-1486 (2001); Thompson, V. F., et al., *Analytical Biochemistry*, 279, 170-178 (2000); "One-step fluorescence-based protease assays," Molecular Probes technical information). These commercial assays are generic protease assays that are designed to inform the assay user of the presence or absence of protease enzymes, and thus rely on the use of a "generic protease substrate," meaning a substrate that is generally susceptible to proteolytic degradation by many proteases, as the protease substrate in the assay. Generic protease substrates can detect the presence of a variety of proteases and are can be especially important for assessing protease contamination in cells, cell lysates, tissue extracts, purified enzymes and purified recombinant proteins. Generic protease substrates can also be useful for comparing overall enzymatic activity in normal cells/tissues and diseased cells/tissues.

However, as the current protease assays available for detecting general protease activity all use "general protease substrates" having visible-range fluorophores associated therewith, these current assays suffer from the drawbacks of undesired background fluorescence (either from biological sample, library compounds, microplate, or scattering photons), and low assay sensitivity, all of which greatly hinder the utility of the current assays.

In another aspect, the modulation of fluorescence in a fluorescent probe can be achieved by associating a reporter-quencher dye pair with a biomolecule or ligand either through conjugation of each dye of the reporter-quencher dye pair to the same biomolecule, or through specific binding of a reporter-dye labeled biomolecule or ligand to a quencher-dye labeled biomolecule or ligand. Biological applications based on reporter-quencher dye pairs include, for example, kinase assays, nucleic acid hybridization assays, protein-protein interaction assays and protease assays. A protease assay of this type is typically configured such that a reporter-quencher dye pair is associated with a peptide protease substrate. Unlike a generic protease assay, described above, this type of protease assay is highly specific, and requires that certain peptide sequences in the protease substrate are recognized, bound and proteolytically processed by a specific protease. Protease assays designed to detect the activity of a specific protease are useful for detecting the presence of a specific protease in cells, cell lysates, tissues/tissue extracts; and are generally amenable to screening drug compound libraries for "hits" that is, compounds that are, for example, antagonists or agonists of the specific protease of interest, in which such modulation of protease activity may have therapeutic value.

Many organic dyes may be used as quenchers in bioassays as long as the spectrally matched fluorophore-quencher pair can be brought into proximity with proper alignment. However, many organic dyes that might be used as quenchers have intrinsic fluorescence. This can result in high background fluorescence and hence attenuate the sensitivity of assays. Dark quenchers with little or no intrinsic fluorescence can efficiently quench the fluorescence from the proximate fluorophores with little background when a large extent of spectral overlap exists between the emission spectrum of the donor/reporter fluorophore and the absorption spectrum of the acceptor quencher dye. Among the dark quenchers, an azo dye, 4-(4'dimethylaminophenylazo)benzoic acid (DABCYL) is a widely used dark quencher in many assays, such as "molecular beacons" for DNA detection (see, U.S. Pat. No. 5,989,823) and protease assay for protease activity or inhibition detection (see, Science, 1990, 247(4945), 954-958). However, the absorption wavelength region (absorption maxima around 540 nm) for DABCYL quenchers restricts the utility of these compounds to short wavelength fluorophores donors. Diazo dyes of the BHQ series, which are referred to as "Black Hole Quenchers" (International Patent Publication No. WO 01/86001), provide a broad range of absorption with absorption maxima around 670 nm which overlaps well with the emission of many fluorophores in the visible region. The QSY series dyes from Molecular Probes are another series of dark quenchers having little or no observable fluorescence which absorbs maximally above 530 nm. The QSY dyes are derivatives of 3- and/or 6-amino xanthenes that are substituted at one or more amino nitrogen atoms by an aromatic or heteroaromatic quenching moiety and are used extensively as quenching reagents in many bioassays (see, U.S. Pat. No. 6,399,392). Non-fluorescent cyanine type dyes have also been developed. A class of nitro-substituted non-fluorescent asymmetric cyanine dye compounds (see, U.S. Pat. Nos. 6,750,024; 6,348,596; and 6,080,868) are useful in the context of a reporter-quencher energy transfer compound pair, particularly useful in nucleic acid hybridization assays employing fluorescence energy transfer as a means of detection. This class of quencher dyes also have short absorption wavelength thus limiting their pairings to short wavelength xanthene fluorescent donor dyes such as fluorescein and rhodamine dyes.

Another problem associated with the current dark quencher dyes is their poor water solubility due to their highly hydrophobic structure characteristic. Poor water solubility of the quencher dyes limits their applications in biological assays as their corresponding bioconjugates 1) are more difficult to prepare and purify; 2) are often not sufficiently soluble in the aqueous assay medium; 3) and exhibit undesired non-specific binding with other biomolecules in the assay.

In view of the foregoing, there remains a need for new NIR reporter dyes, NIR quencher dyes and biological probes having associated therewith NIR reporter and/or quencher dyes; and for biological assays using NIR dye technology that overcome the disadvantages of assays based on visible fluorophores. A need for NIR quenchers that have good water solubility, have large spectral overlap of their absorption spectra with most NIR fluorophores of interest, and are essentially non-fluorescent over a broad pH range also exists. Additionally, there remains a need for an improved generic protease assay technology. Surprisingly, the present invention satisfies these and other needs.

BRIEF SUMMARY OF THE INVENTION

Quenchers having good water solubility, little or no intrinsic fluorescence and which can efficiently quench the fluorescence from a proximate NIR fluorophore with little background are needed. As such, in one embodiment, the present invention provides for near IR quenching cyanine dyes having formulae I-Id that 1) have absorption wavelengths in the near-infrared region of about 650-900 nm; and 2) are essentially non-fluorescent.

In one aspects, the essentially non-fluorescent cyanine dyes of the present invention have formula I:

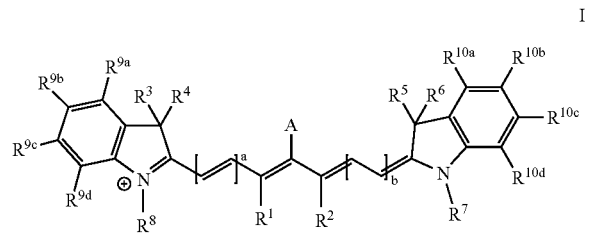

wherein the substituents in formula I are defined as follows: $R^1$ and $R^2$ are each independently selected from the group consisting of hydrogen and optionally substituted $(C_1$-$C_6)$ alkyl. Alternatively, $R^1$ and $R^2$ together with the

group to which they are bonded form a 5- to 7-membered ring, the ring being optionally substituted with 1 to 4 substituents selected from the group consisting of halogen, cyano, sulfonate, $(C_1$-$C_8)$haloalkyl, hydroxy, $(C_1$-$C_6)$alkoxy and optionally substituted $(C_1$-$C_8)$alkyl.

In formula I, $R^3$ and $R^4$ are each independently an optionally substituted $(C_1$-$C_6)$alkyl, and may optionally join together with the atoms to which they are attached to form a 5- to 7-membered carbocyclic ring; or alternatively, the substituents $R^3$ and $R^4$ are replaced with the group

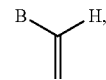

wherein B is $(C_1$-$C_6)$alkyl; or B and $R^{9a}$ together with the carbon atoms to which they are attached join to form a 5- or 6-membered ring optionally having 1 or 2 heteroatoms and optionally having up to 3 double bonds.

The substituents $R^5$ and $R^6$ are each independently an optionally substituted $(C_1$-$C_6)$alkyl, and may optionally join together with the atom to which they are attached to form a ring.

The substituents $R^7$ and $R^8$ are each independently selected from the group consisting of optionally substituted $(C_1$-$C_6)$ alkyl, optionally substituted aryl$(C_1$-$C_6)$alkyl, optionally substituted heteroaryl$(C_1$-$C_6)$alkyl, —$(CH_2)_c R^{13}$ and —$(CH_2)_d R^{15}$. Indices c and d are each independently an integer from 1-50. $R^{13}$ is a functional group that does not directly react with a carboxyl, hydroxyl, amino or thio group on a biomolecule. $R^{15}$ is a linking group selected from the group consisting of mercapto, amino, haloalkyl, phosphoramidityl, N-hydroxy succinimidyl ester, sulfo N-hydroxysuccinimidyl ester, isothiocyanato, iodoacetamidyl, maleimidyl and an activated carboxylic acid.

The substituents $R^{9a-9d}$ and $R^{10a-10d}$ are each independently selected from the group consisting of hydrogen, optionally substituted $(C_1-C_6)$alkyl, $—SO_3Cat^+$, halogen, $—C(O)OR^{11}$, $—C(O)NR^{11}R^{12}$, $—C(O)O(CH_2)_dR^{15}$, $—C(O)NR^{11}(CH_2)_dR^{15}$, $—NR^{12}C(O)O(CH_2)_dR^{15}$, $—NR^{12}C(O)OR^{11}$, $—(CH_2)_dR^{15}$, $—S(O)_2NR^{12}(CH_2)_dR^{15}$, $—R^{15}$ and $—NR^{20}R^{21}$, wherein $Cat^+$ is a cation. The substituents $R^{11}$ and $R^{12}$ are each independently selected from the group consisting of hydrogen and $(C_1-C_6)$alkyl; $R^{20}$ and $R^{21}$ are each independently selected from the group consisting of hydrogen, optionally substituted $(C_1-C_8)$alkyl, $CatO_3S(C_1-C_{50})$alkylene.

Alternatively, any two substituents of $R^{10a-10d}$ located on adjacent atoms, together with the atoms to which they are attached, join to form a 5- or 6-membered ring optionally having 1 or 2 heteroatoms and optionally having up to 3 double bonds; wherein the ring may be further substituted with 1 to 3 substituents selected from the group consisting of optionally substituted $(C_1-C_6)$alkyl, $—SO_3^-Cat$, halogen, $—C(O)OR^{11}$, $—C(O)NR^{11}R^{12}$, $—C(O)O(CH_2)_dR^{15}$, $—C(O)NR^{11}(CH_2)_dR^{15}$, $—NR^{12}C(O)O(CH_2)_dR^{15}$, $—NR^{12}C(O)OR^{11}$, $—S(O)_2NR^{12}(CH_2)_dR^{15}$, $—R^{15}$ and $—NR^{20}R^{21}$ In formula I, the variable a is an integer from 0-3 and the variable b is an integer from 0-2. A is selected from the group consisting of hydrogen, halogen, cyano, optionally substituted $(C_1-C_8)$alkyl, optionally substituted $(C_1-C_6)$dialkylamino, optionally substituted alkylthio, $—(CH_2)_dR^{15}$, $—R^{15}$, optionally substituted $(C_1-C_6)$heteroalkyl, phenoxy and an optionally substituted aryloxy group having the formula

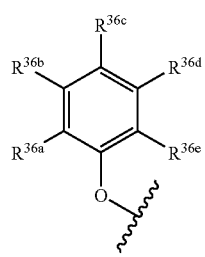

wherein $R^{36a}$-$R^{36e}$ are each independently selected from the group consisting of hydrogen, $—SO_3Cat^+$, $—(CH_2)_dR^{15}$, $—C(O)O(CH_2)_dR^{15}$, $—C(O)NR^{11}(CH_2)_dR^{15}$, $—NR^{12}C(O)O(CH_2)_dR^{15}$, $—S(O)_2NR^{12}(CH_2)_dR^{15}$, $—R^{15}$, $(C_1-C_6)$alkyl, carboxyl and $NR^{20}R^{21}$.

The compounds of the invention have at least one linking group. In certain aspects, the compounds of the invention have one or more linking groups such as for example, 1, 2, 3 or more linking groups. The at least one linking group $R^{15}$ can be attached at various positions on the compound of formula I.

In another aspect, the present invention provides substantially non-fluorescent NIR probes. In one aspect, the substantially non-fluorescent NIR probe is a biomolecule, or ligand comprising an essentially non-fluorescent NIR quencher dye of the invention conjugated thereto. In another aspect, the substantially non-fluorescent NIR probe is a biomolecule having a non-fluorescent NIR quencher dye of the invention further comprising a NIR fluorescent (reporter) dye conjugated thereto. In yet another aspect, the NIR probe is a protein comprising a plurality of NIR fluorescent (reporter) dyes to an extent such that fluorescence quenching occurs, and is a substantially non-fluorescent substrate. In yet another aspect, the present invention provides for biological assays based on these novel substantially non-fluorescent NIR probes. These and other embodiments will become more apparent when read with the detailed description and figures that follow.

BRIEF DESCRIPTION OF THE DRAWINGS

FIG. 1A shows that the intrinsic fluorescence of non-fluorescent quenchers disclosed in this invention in a methanol solution is extremely low, essentially non-fluorescent (left panel). An enlargement of the data in methanol is shown in the right panel (with the absence of NIR Reporter Dye A data). FIG. 1B shows that the intrinsic fluorescence of the non-fluorescent quenchers disclosed in this invention compared with a commercially available fluorescent dye, NIR Reporter Dye A, absorbing within the same wavelength region in a basic solution (50 mM TRIS-HCl buffer containing 10% DMSO, pH 7.5) is extremely low. An enlargement of the data at pH 7.5 is shown in the right panel (with the absence of NIR Reporter Dye A data). FIG. 1C shows that the intrinsic fluorescence of the non-fluorescent quenchers disclosed in this invention compared with a commercially available fluorescent dye, NIR Reporter Dye A, absorbing within the same wavelength region in an acidic solution (50 mM TRIS-HCl buffer containing 10% DMSO at pH 4.6) is extremely low. The right panel shows the enlargement of the data at acidic pH (with the absence of NIR Reporter Dye A data). FIG. 1D shows the direct comparison of the data from FIGS. 1B and 1C. The left panel shows that the intrinsic fluorescence of non-fluorescent quenchers disclosed in this invention is extremely low in both acidic and basic pH. The right panel shows the enlargement of this data (with the absence of NIR Reporter Dye A data). This comparison shows that several non-fluorescent quenchers of the invention, e.g., 9, 5 and 12 show a slight increase in their intrinsic fluorescence level in acidic pH buffer compared with a basic pH buffer. However, the change is so small that the difference can be considered negligible. Other quenchers disclosed in this invention such as 19B and 19A do not have pH dependent intrinsic fluorescence. FIG. 1E shows the intrinsic fluorescence of compound 21 in a methanol solution. The intrinsic fluorescence of compound 21 in methanol is ~0.2% of that of NIR Reporter Dye A (see, FIG. 1E, left panel). An enlargement of the data in methanol is shown in the right panel (with the absence of NIR Reporter Dye A data). FIG. 1F shows the intrinsic fluorescence of compound 21, as compared to a commercially available fluorescent dye, NIR Reporter Dye A, absorbing within the same wavelength region in a buffer solution (50 mM TRIS-HCl buffer, pH 7.8). The intrinsic fluorescence of compound 21 in TRIS buffer (pH 7.8) is ~1.1% of that of NIR Reporter Dye A (see, FIG. 1F, left panel). An enlargement of the data in this buffer solution is shown in the right panel (with the absence of NIR Reporter Dye A data).

FIG. 5A shows the assay plate as detected by the Aerius® Automated Infrared Imaging System. FIG. 5B shows the $IC_{50}$ curve from the inhibition experiments.

FIG. 8A shows the effect of background fluorescence on a HIV-1 protease assay of the invention. FIG. 8B shows the effect of a color quencher compound (Orange G) on a HIV-1 protease assay of the invention. FIG. 8C shows the effect of a light scattering compound on a HIV-1 protease assay.

FIG. 10 shows the properties of NIR Reporter Dye B in various solutions.

FIG. 19A illustrates the synthesis of a BACE-1 protease substrate of the invention (SEQ ID NOS:8-10 and 5, respectively). FIG. 19B shows the purity of a BACE-1 protease substrate of the invention by HPLC chromatography.

FIG. 20A shows the fluorescence intensity increase seen in a BACE-1 enzyme activity assay resulting from the proteolytic cleavage of BACE-1 protease substrate that is conjugated to NIR Reporter Dye A and a quencher compound 6. FIG. 20B shows the fluorescence standard curve obtained from the BACE-1 enzyme activity assay. FIG. 20C shows the results of a time course experiment using various concentration of the BACE-1 enzyme in the BACE-1 enzyme activity assay.

FIG. 22A shows the assay plate wherein each well contains 200 nm of a BACE-1 protease substrate, 100 nm of BACE-1 enzyme and varying concentrations of a BACE-1 inhibitor, i.e., Statine-derived peptide inhibitor (SEQ ID NO:11). The assay was performed in duplicate. The assay plate was detected by the Aerius® Automated Infrared Imaging System. FIG. 22B shows the $IC_{50}$ curve from the inhibition experiment.

FIG. 25A depicts a scheme that outlines the model tyrosine kinase assay. FIG. 25B illustrate the quenching efficiency results from the model tyrosine kinase assay.

FIG. 27A illustrates the result of the method using a quencher conjugated pTyr100 antibody with a D/P ratio of 3.5. FIG. 27B illustrates the same assay using a quencher conjugated pTyr100 antibody with a D/P ratio of 6.5.

DETAILED DESCRIPTION OF THE INVENTION

Figure 1:
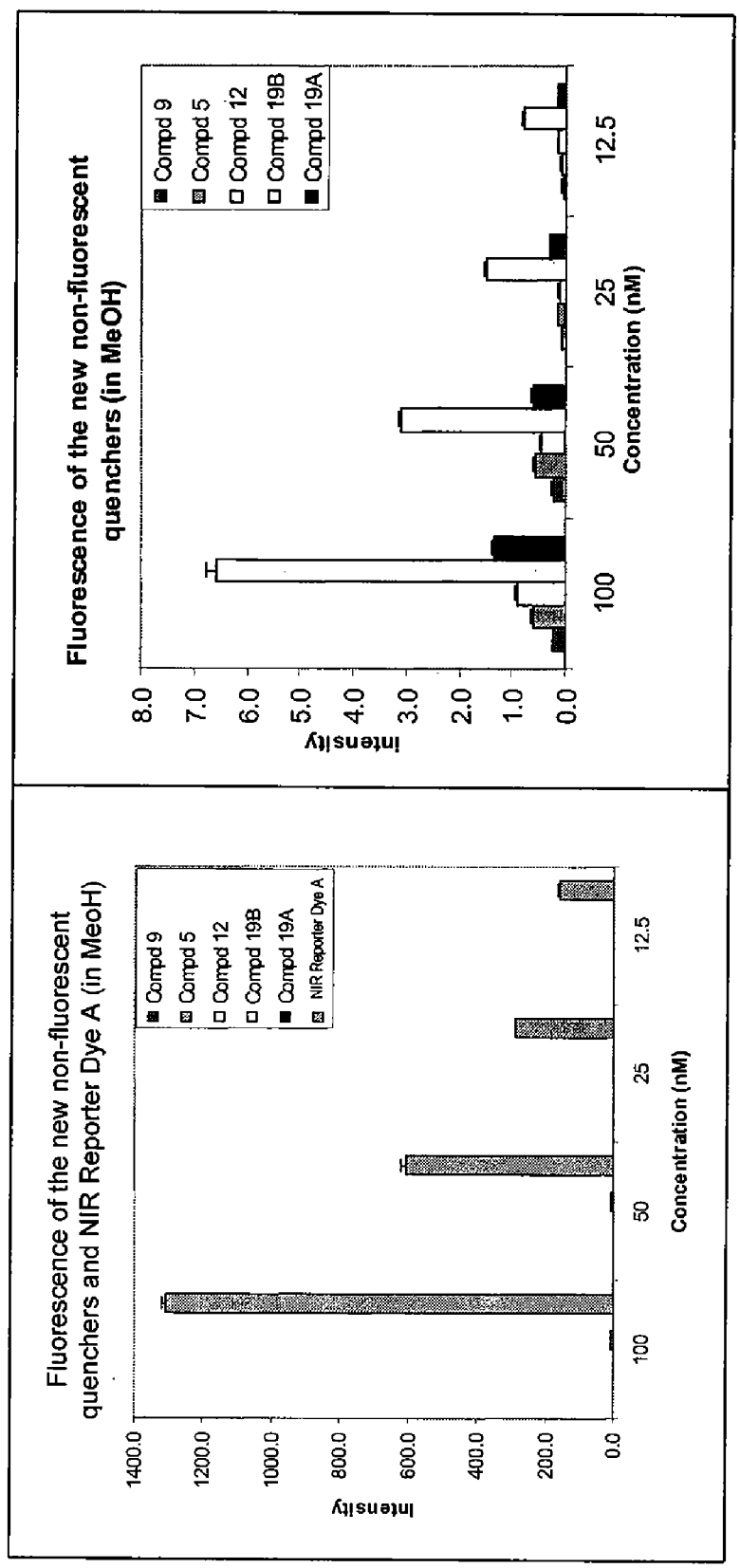
FIGS. 1A to 1D show in one example intrinsic fluorescence of the non-fluorescent quenchers disclosed in this invention compared with a commercially available fluorescent dye absorbing within the same wavelength region, NIR Reporter Dye A.
FIGS. 1E to 1F show the intrinsic fluorescence of another essentially non-fluorescent quencher, compound 21 as compared with a commercially available fluorescent dye absorbing within the same wavelength region, NIR Reporter Dye A.
Figure 1B:
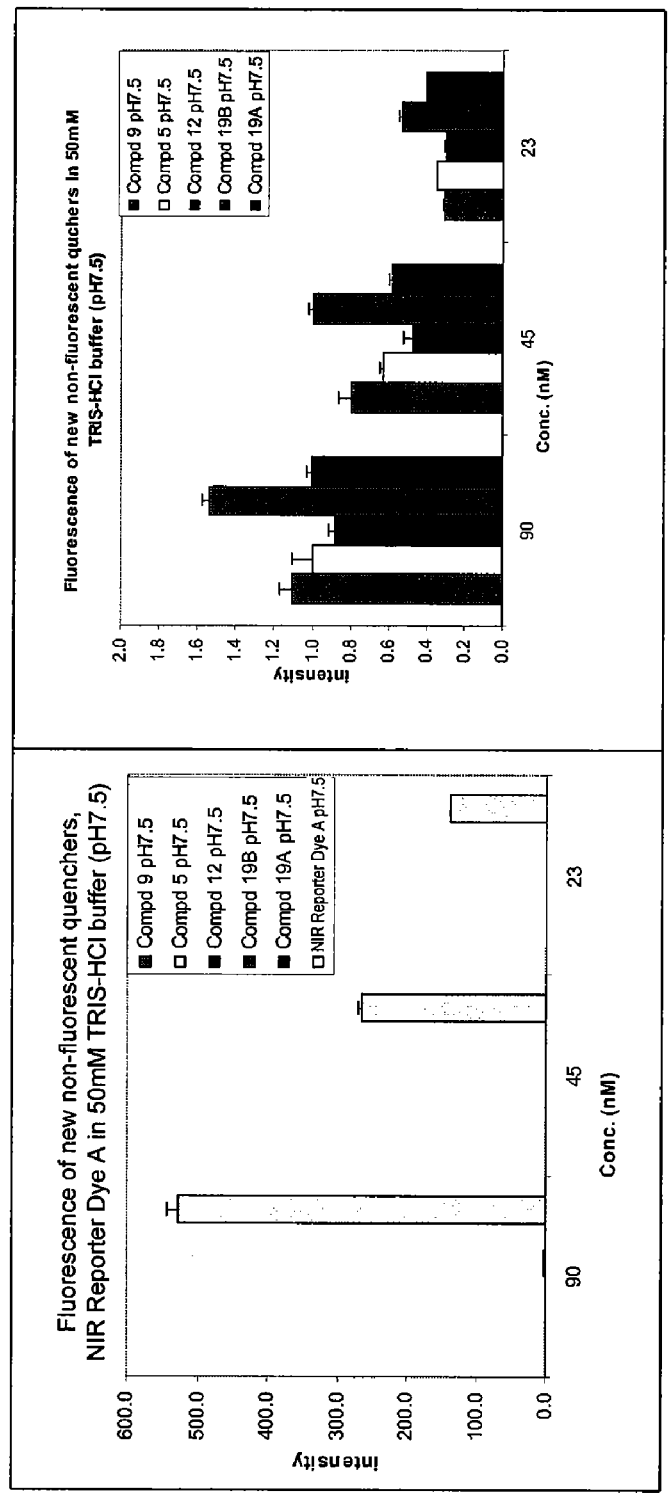
Figure 1:
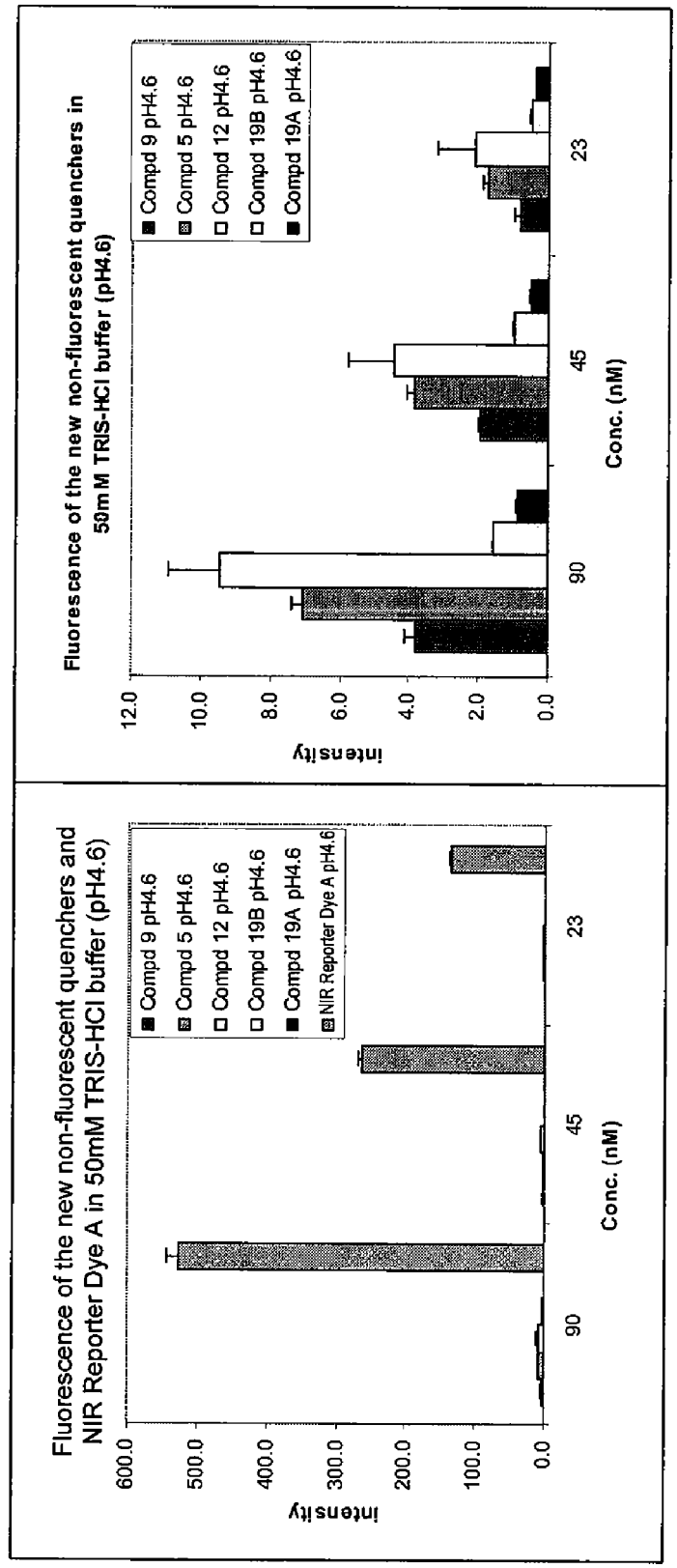
Figure 1:
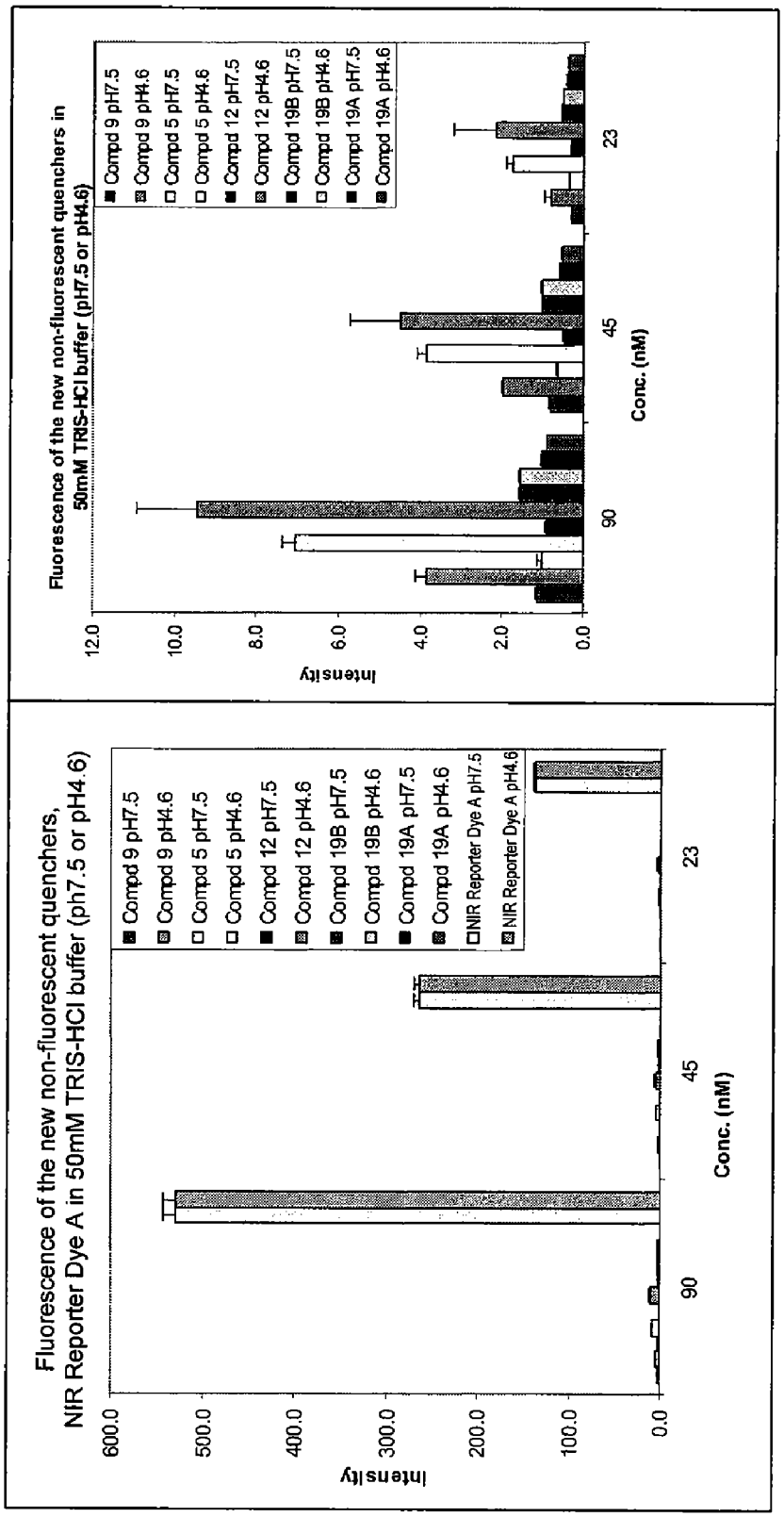
Figure 1:
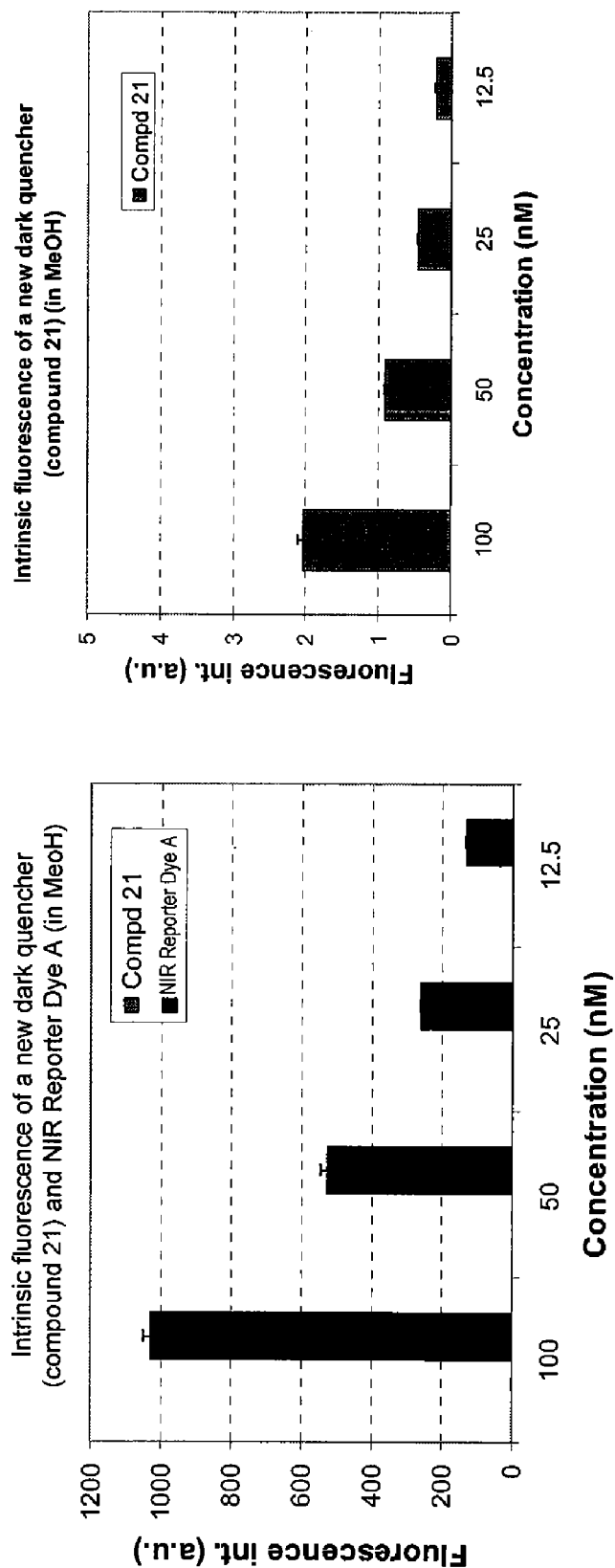
Figure 1:
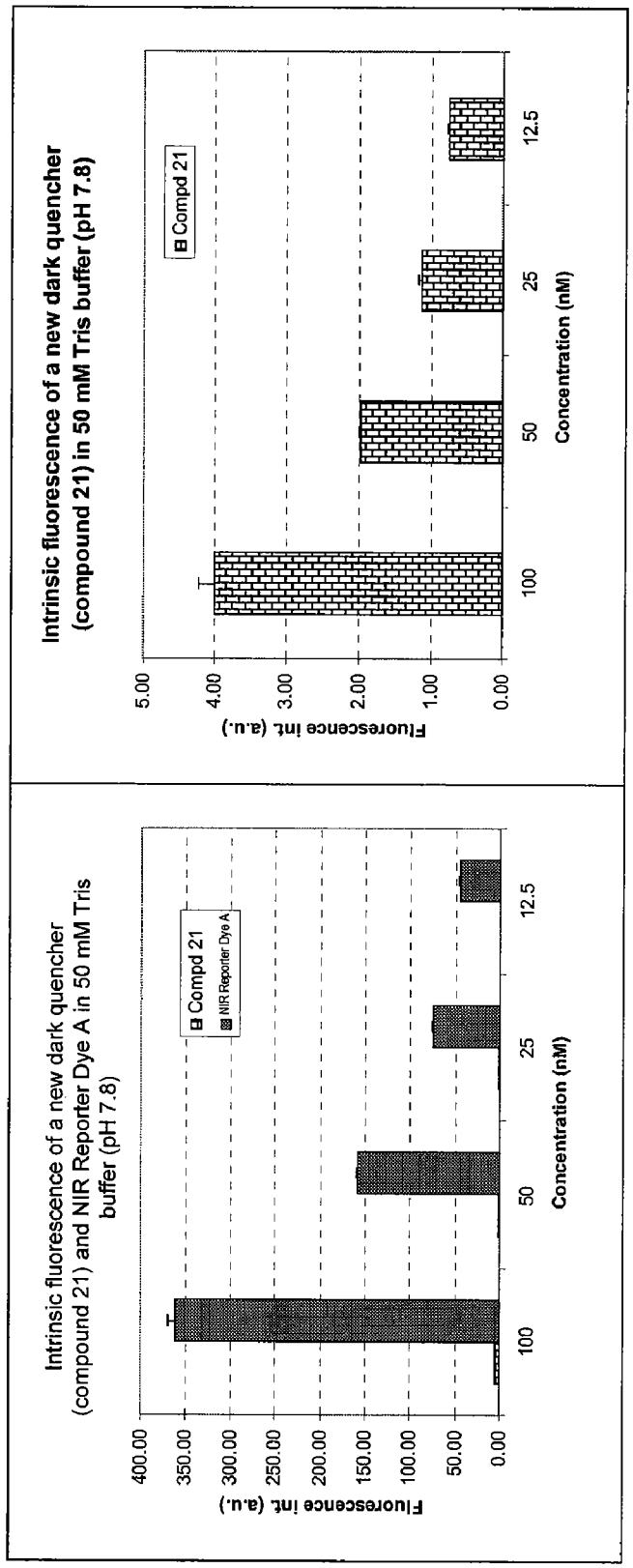

I. General
Definitions

The term "alkyl", by itself or as part of another substituent, includes, a straight or branched chain saturated hydrocarbon radical, having the number of carbon atoms designated (i.e., ($C_1$-$C_8$) means one to eight carbons). Examples of alkyl groups include methyl, ethyl, n-propyl, isopropyl, n-butyl, t-butyl, isobutyl, sec-butyl, n-pentyl, n-heptyl, n-hexyl, n-octyl, and the like. The term "alkenyl" refers to an unsaturated alkyl group having one or more double bonds. Similarly, the term "alkynyl" refers to an unsaturated alkyl group having one or more triple bonds. Example of unsaturated alkyl groups include vinyl, 2-propenyl, crotyl, 2-isopentenyl, 2-(butadienyl), 2-pentadienyl, 3-(1,4-pentadienyl), ethynyl, 1- and 3-propynyl, 3-butynyl, and higher homologs and isomers. The term "cycloalkyl" refers to the hydrocarbon ring having the indicated number of ring atoms (e.g., ($C_3$-$C_6$) cycloalkyl) and being fully saturated or having no more than one double bond. The term "alkylene" by itself or as part of another substituent means a divalent radical derived from an alkane, as exemplified by —$CH_2CH_2CH_2CH_2$—.

Typically, an alkyl or alkylene group has 50 or fewer carbon atoms in its backbone, more preferably 30 or fewer, and most preferably 10 or fewer. The term "lower alkyl" or "lower alkylene" means an alkyl group having from 1-10 carbon atoms in its backbone, more preferably from 1-6 carbon atoms. Similarly, "alkenylene" and "alkynylene" refer to the unsaturated forms of "alkylene" having double or triple bonds, respectively.

The terms "alkoxy," "alkylamino" and "alkylthio" (or thioalkoxy) are used in their conventional sense, and includes those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —$NR^aR^b$ is meant to include piperidinyl, pyrrolidinyl, morpholinyl, azetidinyl and the like.

The terms "halo" or "halogen," by themselves or as part of another substituent, include, unless otherwise stated, a fluorine, chlorine, bromine, or iodine atom. Additionally, terms such as "haloalkyl," are meant to include monohaloalkyl and polyhaloalkyl. For example, the term "($C_1$-$C_4$)haloalkyl" is mean to include trifluoromethyl, 2,2,2-trifluoroethyl, 4-chlorobutyl, 3-bromopropyl, and the like.

The term "aryl" include, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, benzopyrazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthio, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like).

The above terms (e.g., "alkyl," "aryl" and "heteroaryl"), in some embodiments, will include both substituted and unsubstituted forms of the indicated radical. Preferred substituents for each type of radical are provided below. For brevity, the terms aryl and heteroaryl will refer to substituted or unsubstituted versions as provided below, while the term "alkyl" and related aliphatic radicals is meant to refer to unsubstituted version, unless indicated to be substituted. For example, as used in the present invention a substituted version of an alkyl group can be referred to as an "optionally substituted" alkyl. Preferred substituents for an optionally substituted alkyl group of the invention are that are substituted with functional group that falls within the definition of a linking group as set forth herein, e.g., a NHS ester, a maleimidyl, a carboxylic acid, an amino group, and the like.

Substituents for the alkyl radicals (including those groups often referred to as alkylene, alkenyl, alkynyl and cycloalkyl) can be a variety of groups selected from: -halogen, —OR', —NR'R", —SR', —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NH—C($NH_2$)=NH, —NR'C($NH_2$)=NH, —NH—C($NH_2$)=NR', —S(O)R', —S(O)$_2$R', —S(O)$_2$NR'R", —NR'S(O)$_2$R", —CN and —$NO_2$ in a number ranging from zero to (2 m'+1), where m' is the total number of carbon atoms in such radical. R', R" and R'" each independently refer to hydrogen, unsubstituted ($C_1$-$C_8$)alkyl, ($C_1$-$C_8$)acyl, unsubstituted heteroalkyl, unsubstituted aryl, aryl substituted with 1-3 halogens, unsubstituted ($C_1$-$C_8$)alkyl, ($C_1$-$C_8$)alkoxy or ($C_1$-$C_8$)thioalkoxy groups, or unsubstituted aryl-($C_1$-$C_4$)alkyl groups. When R' and R" are attached to the same nitrogen atom, they can be combined with the nitrogen atom to form a 3-, 4-, 5-, 6-, or 7-membered ring optionally having 1-3 double bonds. For example, —NR'R" is meant to include 1-pyrrolidinyl, maleimidyl and 4-morpholinyl.

Similarly, substituents for the aryl and heteroaryl groups are varied and are generally selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R'", —NH—C($NH_2$)=NH, —NR'C($NH_2$)=NH, —NH—C($NH_2$)=NR', —S(O)R', —S(O)$_2$R', —S(O)$_2$NR'R", —NR'S(O)$_2$R", —$N_3$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, ($C_1$-$C_8$)alkyl, ($C_3$-$C_6$) cycloalkyl, ($C_2$-$C_8$) alkenyl, ($C_2$-$C_8$) alkynyl, unsubstituted aryl and heteroaryl, (unsubstituted aryl)-($C_1$-$C_4$)alkyl, and unsubstituted aryloxy-($C_1$-$C_4$)alkyl. Other suitable substituents include each of the above aryl substituents attached to a ring atom by an alkylene tether of from 1-4 carbon atoms.

The term "biomolecule" is a natural or synthetic molecule for use in biological systems. Examples of biomolecules include, but are not limited to, antigens, steroids, vitamins, drugs, haptens, metabolites, toxins, environmental pollutants, amino acids, peptides, proteins, nucleotides, oligonucleotides, nucleic acids, (nuclei acid polymers) carbohydrates, lipids, ion-complexing moieties, and non-biological polymers.

As used herein, the term "heteroatom" includes oxygen (O), nitrogen (N), sulfur (S) and silicon (Si).

The term "cation" or "Cat" includes a metal or organic molecule bearing a net positive charge. Non-limiting examples of "cations" include $Na^+$, $Ca^{2+}$, $NH_4^+$, $NR'_4^+$, among others. Preferably, the cation is a biologically acceptable cation.

The term "cyanine dye" includes a compound having two substituted or unsubstituted nitrogen-containing heterocyclic rings joined by a polymethine chain.

The term "linking group" includes a moiety on the compound that is capable of chemically reacting with a functional group on a different material (e.g., biomolecule) to form a linkage, such as a covalent linkage. See R. Haughland, *The Handbook—A Guide to Fluorescent Probes and Labeling Technologies*, 9th Edition, Molecular probes, Inc. (1992). Typically, the linking group is an electrophile or nucleophile that can form a covalent linkage through exposure to the corresponding functional group that is a nucleophile or electrophile, respectively. Alternatively, the linking group is a photoactivatable group, and becomes chemically reactive only after illumination with light of an appropriate wavelength. Typically, the conjugation reaction between the dye bearing the linking group and the material to be conjugated with the dye results in one or more atoms of the linking group being incorporated into a new linkage attaching the dye to the conjugated material.

As used herein, the term "activated carboxylic acid" includes a group having formula —C(O)M, where M is a good leaving group (e.g. N-succinimidyloxy (—$ONC_4H_4O_2$) N-sulfosuccinimidyloxy (—$ONC_4H_3O_2SO_3H$), -1-oxybenzotriazolyl (—$OC_6H_4N_3$); 4-sulfo-2,3,5,6-tetrafluorophenyl; or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —$OCOR^a$ or $OCNR^aNHR^b$, where $R^a$ and $R^b$, which may be the same or different, are ($C_1$-$C_6$)alkyl, ($C_1$-$C_6$)perfluoroalkyl, or ($C_1$-$C_6$)alkoxy; or cyclohexyl, 3-dimethylaminopropyl, or N-morpholinoethyl).

As used herein, the term "a plurality of" near-infrared dyes includes a quantity of at least three dyes.

As used herein, the term "functional group" includes a group of atoms within a molecule that is responsible for certain properties of the molecule and/or reactions in which it takes part. Non-limiting examples of functional groups include, alkyl, carboxyl, hydroxy, amino, sulfonate, halogen, and the like.

II. Compounds

A. Cyanine Quenching Dyes

In one aspect, the present invention provides for near-IR (NIR) cyanine quenching dyes having formulae I-Id that 1) have absorption wavelengths in the near-infrared region of about 650-900 nm; and 2) are essentially non-fluorescent (ENF).

In one embodiment of the invention, the cyanine dyes of the invention have formula I:

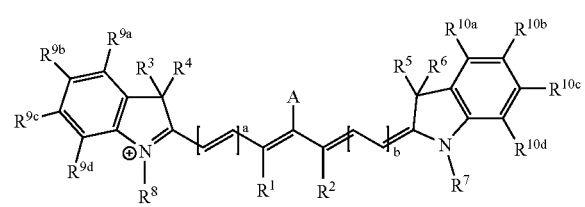

I wherein the substituents in formula one are defined as follows. $R^1$ and $R^2$ are each independently selected from the group consisting of hydrogen and optionally substituted ($C_1$-$C_6$)alkyl. Alternatively, $R^1$ and $R^2$ together with the

group to which they are bonded form a 5- to 7-membered ring, the ring being optionally substituted with 1 to 4 substituents selected from the group consisting of halogen, cyano, sulfonate, ($C_1$-$C_8$)haloalkyl, hydroxy, ($C_1$-$C_6$)alkoxy and ($C_1$-$C_8$)alkyl.

In formula I, $R^3$ and $R^4$ are each an optionally substituted ($C_1$-$C_6$)alkyl, and may optionally join together with the atom to which they are attached to form a 5- to 7-membered carbocyclic ring; or alternatively the substituents $R^3$ and $R^4$ are replaced with the group

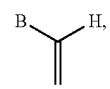

wherein B is ($C_1$-$C_6$)alkyl; or B and $R^{9a}$ together with the carbon atoms to which they are attached join to form a 5- or 6-membered ring optionally having 1 or 2 heteroatoms and optionally having up to 3 double bonds.

The substituents $R^5$ and $R^6$ are each an optionally substituted ($C_1$-$C_6$)alkyl, and may optionally join together with the atom to which they are attached to form a ring.

The substituents $R^7$ and $R^8$ are each independently selected from the group consisting of optionally substituted ($C_1$-$C_6$) alkyl, optionally substituted aryl($C_1$-$C_6$)alkyl, optionally substituted heteroaryl($C_1$-$C_6$)alkyl, —$(CH_2)_cR^{13}$ and —$(CH_2)_dR^{15}$. The integers c and d are each independently an integer from 1-50. $R^{13}$ is a functional group that does not directly react with a carboxyl, hydroxyl, amino or thio group on a biomolecule. $R^{15}$ is a linking group selected from the group consisting of mercapto, amino, haloalkyl, phosphoramidityl, N-hydroxysuccinimidyl ester, sulfo N-hydroxysuccinimidyl ester, isothiocyanato, iodoacetamidyl, maleimidyl and an activated carboxylic acid.

A wide range of non-reactive functional groups are suitable for $R^{13}$. Suitable groups include for example, hydroxyl, thioacetyl, sulfonato, optionally substituted alkyl, optionally substituted aryl, optionally substituted heteroaryl, optionally substituted unactivated carboxyl, optionally substituted cycloalkyl, and optionally substituted heterocyclyl, optionally substituted sulphates, optionally substituted phosphates, and optionally substituted ammonium salts.

The substituents $R^{9a-9d}$ and $R^{10a-10d}$ are each independently selected from the group consisting of hydrogen, optionally substituted ($C_1$-$C_6$)alkyl, —$SO_3Cat^+$, halogen, —$C(O)OR^{11}$, —$C(O)NR^{11}R^{12}$, —$C(O)O(CH_2)_dR^{15}$, —$C(O)NR^{11}(CH_2)_dR^{15}$, —$NR^{12}C(O)O(CH_2)_dR^{15}$, —$NR^{12}C(O)OR^{11}$, —$(CH_2)_dR^{15}$, —$S(O)_2NR^{12}(CH_2)_dR^{15}$, —$R^{15}$ and —$NR^{20}R^{21}$, wherein $Cat^+$ is a cation. The substituents $R^{11}$ and $R^{12}$ are each independently selected from the group consisting of hydrogen and optionally substituted ($C_1$-$C_8$)alkyl; $R^{20}$ and $R^{21}$ are each independently selected from the group consisting of hydrogen, optionally substituted ($C_1$-$C_8$)alkyl, and $CatO_3S(C_1$-$C_{50})$alkylene.

The compounds of the invention have at least one linking group. In other embodiments, the compounds have one or more linking groups such as for example, 1, 2, 3 or more linking groups. In one embodiment, at least one of $R^{9a-9d}$ or $R^{10a-10d}$ has a substituent having the linking group $R^{15}$. In another embodiment, at least one of $R^7$ or $R^8$ has a substituent having a linking group $R^{15}$. In another embodiment, $R^7$ has a substitutent having a linking group $R^{15}$. In certain embodiments, the linking groups are N-hydroxysuccinimidyl ester or maleimidyl. In another embodiment, the linking group is an amino group. In yet another embodiment, the linking group is a phosphoramidite. In still yet another embodiment, $R^7$ is —$(CH_2)_dR^{15}$, wherein d is an integer from 1-10, and wherein $R^{15}$ is a N-hydroxysuccinimidyl ester, a sulfo N-hydroxysuccimidyl ester or a maleimide.

Alternatively, any two substituents of $R^{10a-10d}$ located on adjacent atoms, together with the atoms to which they are attached, join to form a 5- or 6-membered ring optionally having 1 or 2 heteroatoms and optionally having up to 3 double bonds; wherein the ring may be further substituted with 1 to 3 substituents selected from the group consisting of optionally substituted $(C_1-C_6)$alkyl, —$SO_3^-$Cat, halogen, —$C(O)OR^{11}$, —$C(O)NR^{11}R^{12}$, —$C(O)O(CH_2)_dR^{15}$, —$C(O)NR^{11}(CH_2)_dR^{15}$, —$NR^{12}C(O)O(CH_2)_dR^{15}$, —$NR^{12}C(O)OR^{11}$, —$S(O)_2NR^{12}(CH_2)_dR^{15}$, —$R^{15}$ and —$NR^{20}R^{21}$. In one embodiment of the invention, at least one of $R^{9a-9d}$ is —$NR^{20}R^{21}$. In another embodiment, $R^{9b}$ is —$NR^{20}R^{21}$.

In formula I, the variable a is an integer from 0-3 and the variable b is an integer from 0-2. The substituent A, in formula I, is selected from the group consisting of hydrogen, halogen, cyano, optionally substituted $(C_1-C_8)$alkyl, optionally substituted $(C_1-C_6)$dialkylamino, optionally substituted alkylthio, —$(CH_2)_dR^{15}$, —$R^{15}$, optionally substituted $(C_1-C_6)$heteroalkyl, phenoxy and an optionally substituted aryloxy group having the formula

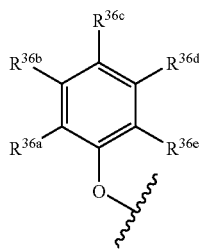

wherein $R^{36a}$-$R^{36e}$ are each independently selected from the group consisting of hydrogen, —$SO_3Cat^+$, —$(CH_2)_dR^{15}$, —$C(O)O(CH_2)_dR^{15}$, —$C(O)NR^{11}(CH_2)_dR^{15}$, —$NR^{12}C(O)O(CH_2)_dR^{15}$, —$S(O)_2NR^{12}(CH_2)_dR^{15}$, —$R^{15}$, $(C_1-C_6)$alkyl, carboxyl and $NR^{20}R^{21}$. In one embodiment, A is halogen. In another embodiment, A is selected from the group consisting of chloro and hydrogen. In another preferred embodiment, A is an optionally substituted aryloxy. In certain aspects of this embodiment, A is an optionally substituted aryloxy comprising at least one —$SO_3Cat^+$ group. In another preferred embodiment, A is a optionally substituted aryloxy, wherein $R^{36a}$, $R^{36b}$, $R^{36d}$ and $R^{36e}$ are each hydrogen and $R^{36c}$ is —$SO_3Cat^+$. In one embodiment of formula I, A is hydrogen; and $R^1$ and $R^2$ are both hydrogen; the variable a is 0 or 1, and the variable b is 0 or 1. In another embodiment of formula I, A is halogen, and $R^1$ and $R^2$ together with the

group to which they are bonded form a 5- to 7-membered ring; and a and b are each 1.

In yet another embodiment of formula I, one or both of the heteroaryl ring systems in the cyanine dye having formula I is benzo[c,d]indolyl or benzo[e]indolyl.

The compounds of the invention have at least one linking group and are essentially non-fluorescent. In one embodiment, the compounds of the invention are essentially non fluorescent in a pH range of about 1 to about 12. In another embodiment, the compounds of the invention are essentially non-fluorescent in a pH range of about 4 to about 8, such as for example, pH values of 4, 5, 6, 7, or 8 or fractional numbers in between.

The compounds of the invention preferably include water solubilizing groups that impart a hydrophilic characteristic to the dye. The solubilizing groups may be attached to any portion of the dye (e.g., to the aromatic ring system of the cyanine dye). Suitable solubilizing groups of the invention include, sulfonate, sulfate, phosphonate, phosphate, quaternary ammonium and hydroxyl. In one embodiment, the compounds having formula I have good water solubility. In another preferred embodiment, the compounds having formula I have at least one sulfonate group, more preferably two or three sulfonate groups attached thereto. In another embodiment, the compounds having formula I do not have a water solubilizing group. Sulfonate groups also are advantageous as they provide increased photostability, and considerable reduction of interaction with surrounding dye molecules, e.g., reduce self-aggregation. The enhanced water solubility provided by sulfonate groups is highly desirable. Biological molecules, such as DNA, RNA, proteins and antibodies are intrinsically water soluble. The hydrophilic nature of these molecules enables them to carry out their respective biological functions inside cells. In contrast, unmodified fluorescent dyes are generally hydrophobic in nature. In order to label a biological molecule with a dye molecule, it is more preferable to synthesize an organic dye that is water soluble as the use of some organic solvents can affect the activity of the biomolecule. The desired hydrophilic character of a compound of the invention will vary depending on its intended application.

Those dyes within the scope of this invention that do not contain at least one sulfonate group and thus are not, or are only slightly, water soluble still can be important in labeling biomolecules provided the organic solvent or co-solvent selected is one which no more than minimally affects the activity of the biomolecule. Such solvents can include, for example, DMF, DMSO and mixtures thereof. Those of skill in the art will know of other solvents useful in the present invention.

In certain embodiments, the compounds of the invention having the formula I-Id have at least one —$NR^{20}R^{21}$ group. In another embodiment, the compounds of the invention have one —$NR^{20}R^{21}$ group. In certain embodiments, the —$NR^{20}R^{21}$ group is located para or ortho to the position of the nitrogen atom of the heteroaryl groups on the dye (e.g., position $R^{9b}$, $R^{9d}$, $R^{10b}$ or $R^{10d}$ in formulae I and Id, position $R^{9b}$, $R^{9d}$, or $R^{10b}$ in formulae Ib and Ic). In other embodiments, the —$NR^{20}R^{21}$ group is located para to the position of the nitrogen atom of the heteroaryl groups on the dye (e.g., position $R^{9b}$ or $R^{10b}$ in formulae I and Id, position $R^{9b}$ in formulae Ib and Ic of the present invention). In one embodiment, at least one of $R^{9a-9d}$ in the compounds of formula I and Ib, or at least one of $R^{9b-9d}$ in the compounds of formula Ic-Id is —$NR^{20}R^{21}$. In another embodiment, $R^{9b}$ in formula I-Id is —$NR^{20}R^{21}$. In a preferred aspect, the compounds of formula I-Id, have at least one —$NR^{20}R^{21}$ group, wherein at least one of $R^{20}$ and $R^{21}$ is not hydrogen. Without being bound by any particular theory, it is believed that the addition of a —NR$^{20}$R$^{21}$, group to a compound of the invention can have the affect of modulating the fluorescence properties of the compound. More particularly, it is believed that, although not required, the presence of a —NR$^{20}$R$^{21}$ group on a compound of the invention can diminish or substantially abolishes the intrinsic fluorescence of the compound, and renders the compound of the invention essentially non-fluorescent.

In preferred aspects, the cyanine dyes of the invention contain at least one linking group. The linking group can be attached directly to the dye or indirectly to a substituent that is attached to the dye. Typically, a linking group is an electrophile or nucleophile that can form a covalent linkage through exposure to the corresponding functional group that is a nucleophile or electrophile, respectively. Preferably, the corresponding functional group is located on a biomolecule. A list of suitable electrophiles and nucleophiles that can react to form a covalent linkage is set for in Table 2 of U.S. Pat. No. 6,399,392, which is incorporated herein by reference in its entirety. Non-limiting examples of linking groups include, an activated carboxylic acid, an acyl halide, an alkyl halide, an anhydride, a carboxylic acid, a carbodiimide, a carbonate, a carbamate, a haloacetamide (e.g., iodoacetamide), an isocyanate, an isothiocyanate, a maleimide, an NHS ester, a phosphoramidite, a platinum complex, a sulfonate ester, a thiocyanate, a boronate, a halotriazine, an azide, diazirinyl, azidoaryl, azidoperfluoroaryl, a psoralen derivative, and the like. Preferably, the linking group is one that forms a covalent bond with the corresponding functional group. In one embodiment, the linking group is an NHS ester or a maleimide.

The choice of the linking group used to attach the quencher dye of the invention to the substrate to be conjugated, e.g., a biomolecule, typically depends in part on the functional group on the substance to be conjugated and the type or length of the covalent linkage desired. The types of functional groups typically present on a substrate to be conjugated include, but are not limited to, amine, thiols, alcohols, phenols, aldehydes, ketones, phosphates, imidazoles, hydrazines, hydroxylamines, disubstituted amines, halides, epoxides, sulfonate esters, purines pyrimidines, carboxylic acids, and the like. Linking groups which react with a carboxyl group, an amine, or a thiol group on a biomolecule are preferred.

Preferably, the dyes of the present invention have a maximum light absorption wavelengths in the near infrared region of between about 650 nm and 900 nm, for example, at approximately 800 nm. The quencher compounds of the invention having formula I are essentially non-fluorescent.

As used herein, a compound that is referred to as "essentially non-fluorescent," or "ENF" indicates that the compound has an intrinsic fluorescence of less than about 10 percent as evaluated according to the method described below and recorded using the spectroscopic instrumentation described herein, i.e., Aerius® Automated Infrared Imaging System, Odyssey® Infrared Imaging System (both from LI-COR® Biosciences); or an equivalent apparatus. In certain embodiments, the compounds of the invention have an intrinsic fluorescence of less than about 5 percent, such as 4%, 3%, 2% and 1%. In other embodiments, the compounds of the invention have an intrinsic fluorescence of about less than about 1 percent. In yet another embodiment, the intrinsic fluorescence is less than about 0.5 percent. In still yet another embodiment, the intrinsic fluorescence is less than about 0.1 percent. In still yet another embodiment, the intrinsic fluorescence is less than about 0.05 percent. The intrinsic fluorescence is measured by comparing the fluorescence emission of a reporter dye (R) to that of a quencher dye of the present invention (Q) at the same concentration when the reporter and quencher dye are each excited at the reporter excitation wavelength (e.g., 780 nm) and the detection of emission is also at the reporter emission wavelength (e.g., 810 nm to 830 nm) (eq. 1).

$$\text{Intrinsic flouresence} = \frac{Q}{R} \times 100 \quad \text{eq. 1}$$

As shown in FIGS. 1A-1D, the intrinsic fluorescence of certain quencher dyes of the invention, i.e., Compounds 5, 9, 13, 19A and 19B as compared to a complementary reporter dye, i.e., NIR Reporter Dye A, is very low, e.g., less than 1 percent. Advantageously, as shown in FIGS. 1A-1D, the essentially non-fluorescent property of the dye quenchers of the invention is substantially pH independent.

Additional particular embodiments of compounds having formula I are set forth below in formulae Ib-Id.

In one embodiment, the compounds of the invention has formula Ib:

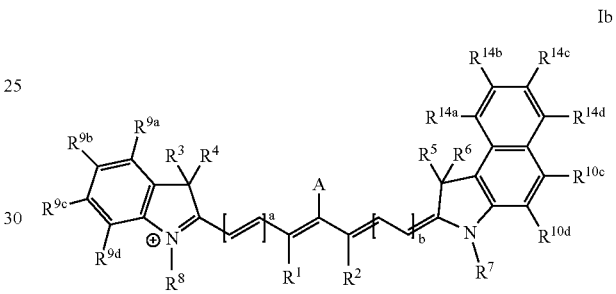

Ib wherein R$^{14a-14d}$ are each independently selected from the group consisting of hydrogen, optionally substituted (C$_1$-C$_6$) alkyl, —SO$_3$Cat$^+$, halogen, —C(O)OR$^{11}$, —C(O)NR$^{11}$R$^{12}$, —C(O)O(CH$_2$)$_d$R$^{15}$, —C(O)NR$^{11}$(CH$_2$)$_d$R$^{15}$, —NR$^{12}$C(O)O(CH$_2$)$_d$R$^{15}$, —NR$^{12}$C(O)OR$^{11}$, —(CH$_2$)$_d$R$^{15}$, —S(O)$_2$NR$^{12}$(CH$_2$)$_d$R$^{15}$, —R$^{15}$ and —NR$^{20}$R$^{21}$. In one embodiment, at least one of R$^{14a}$ to R$^{14d}$ in formula Ib is —SO$_3$Cat$^+$. In one embodiment, at least one of R$^{9a}$ to R$^{9d}$ is NR$^{20}$R$^{21}$. In one embodiment, at least one of R$^{14a}$ to R$^{14d}$ in formula Ib is —SO$_3$Cat$^+$ and at least one of R$^{9a}$ to R$^{9d}$ is NR$^{20}$R$^{21}$.

In another embodiment, the quencher dyes of the invention has formula Ic:

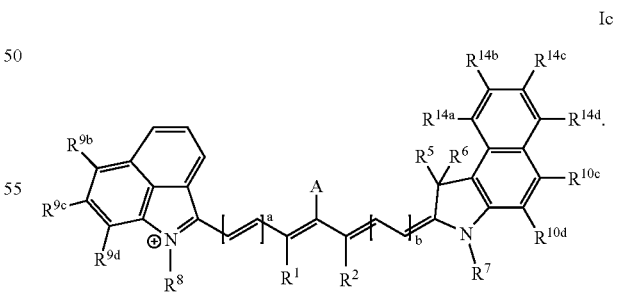

Ic

In one embodiment, at least one of R$^{9b}$ to R$^{9d}$ in formula Ic is a —NR$^{20}$R$^{21}$ group; wherein R$^{20}$ and R$^{21}$ are each independently hydrogen or an optionally substituted (C$_1$-C$_8$)alkyl group. In another embodiment, at least one of R$^{9b}$, R$^{9d}$ and R$^{10d}$ on formula Ic is a —NR$^{20}$R$^{21}$ group. In yet another embodiment the compounds of formula Ic does not have a —NR$^{20}$R$^{21}$ group.

In yet another embodiment, the dyes of the invention have formula Id:

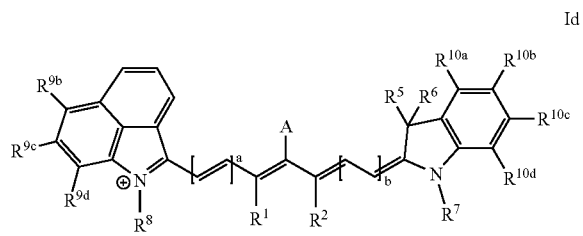

wherein $R^{10a\text{-}10d}$ are each independently selected from the group consisting of hydrogen, optionally substituted ($C_1$-$C_6$) alkyl, —$SO_3^-$Cat, halogen, —C(O)O$R^{11}$, —C(O)N$R^{11}R^{12}$, —C(O)O(CH$_2$)$_d R^{15}$, —C(O)N$R^{11}$(CH$_2$)$_d R^{15}$, —N$R^{12}$C(O)O(CH$_2$)$_d R^{15}$, —N$R^{12}$C(O)O$R^{11}$, —(CH$_2$)$_d R^{15}$, —S(O)$_2$N$R^{12}$(CH$_2$)$_d R^{15}$, —$R^{15}$ and —N$R^{20}R^{21}$. In another embodiment, at least one of $R^{9b}$, $R^{9d}$, $R^{10b}$ and $R^{10d}$ on formula Ic is a —N$R^{20}R^{21}$ group. In yet another embodiment, the compound of formula Id does not have a —N$R^{20}R^{21}$ group.

In yet another embodiment, the quencher dyes having formula I is selected from the group consisting of:

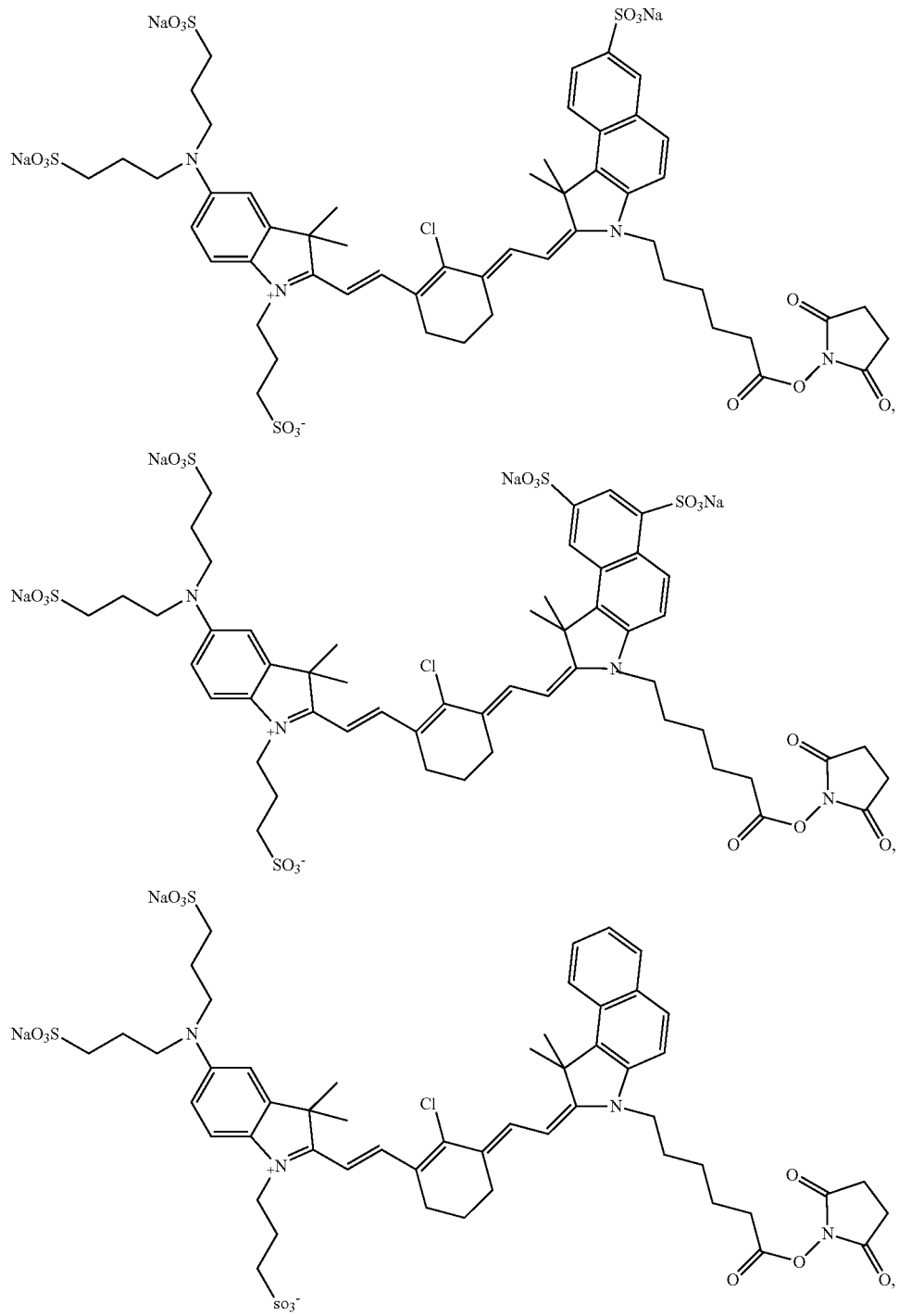

-continued
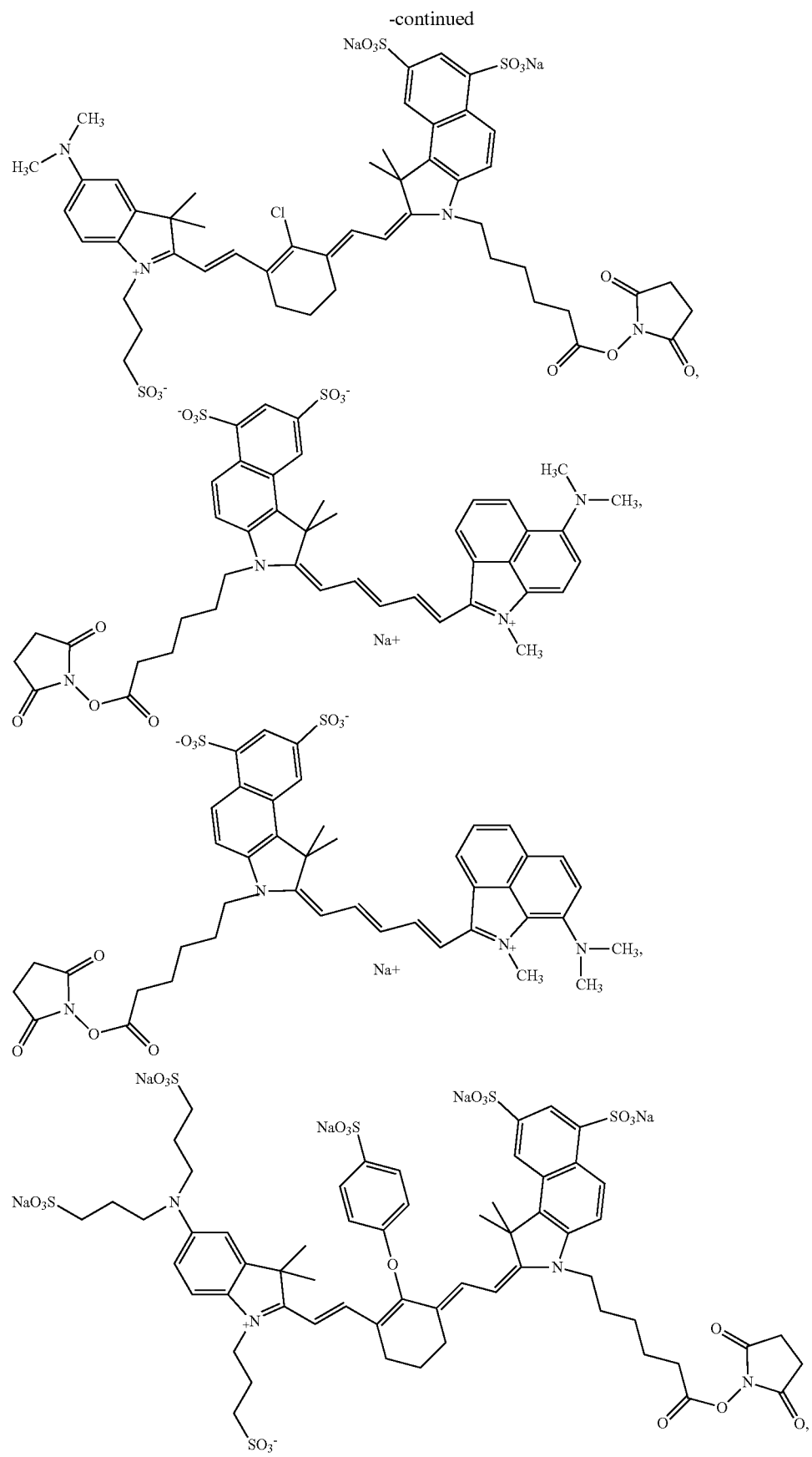

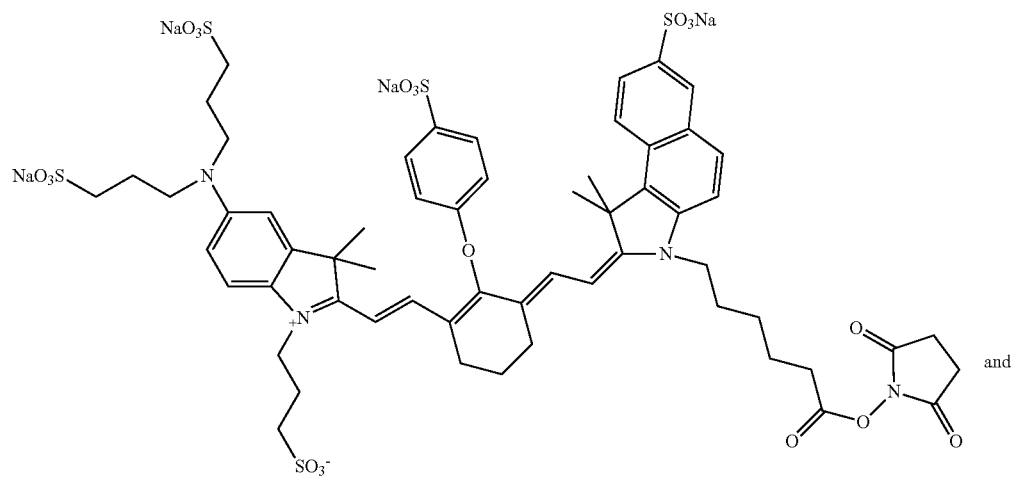
and
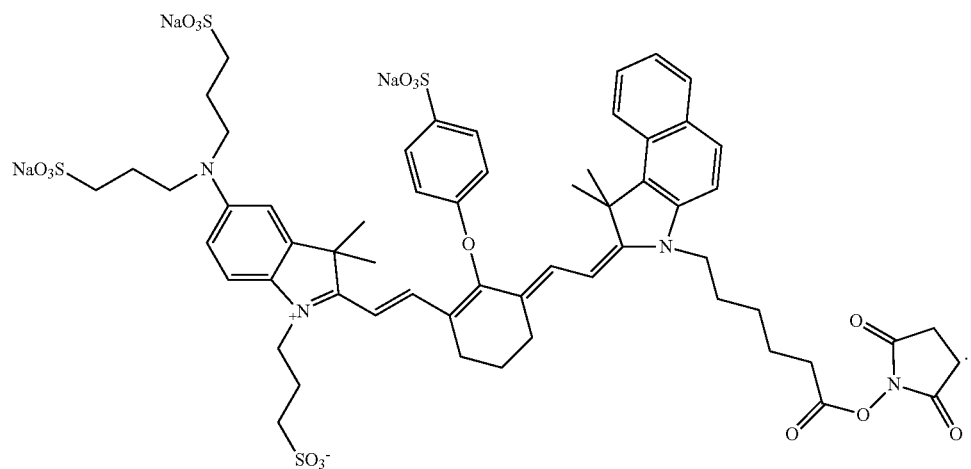
In yet another embodiment, the quencher dyes having formula I is selected from the group consisting of:
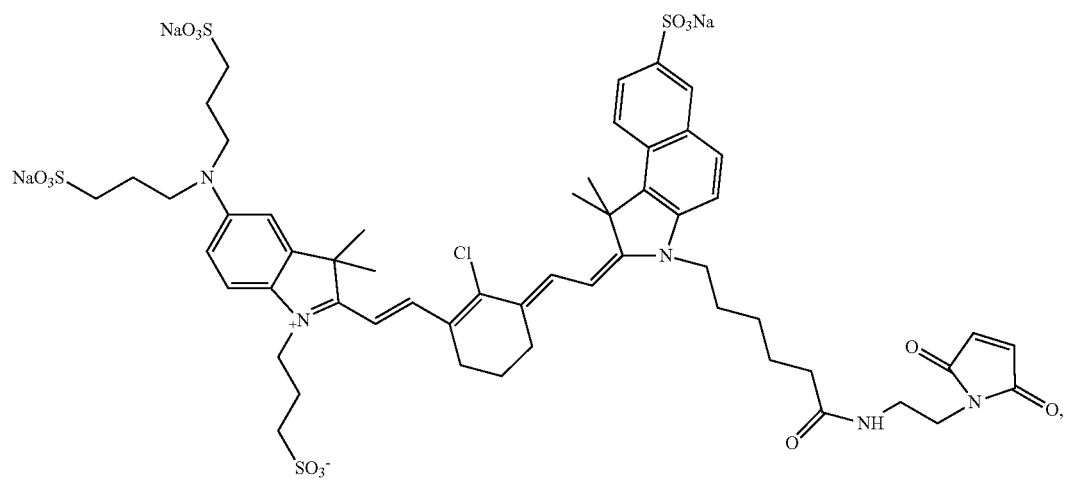

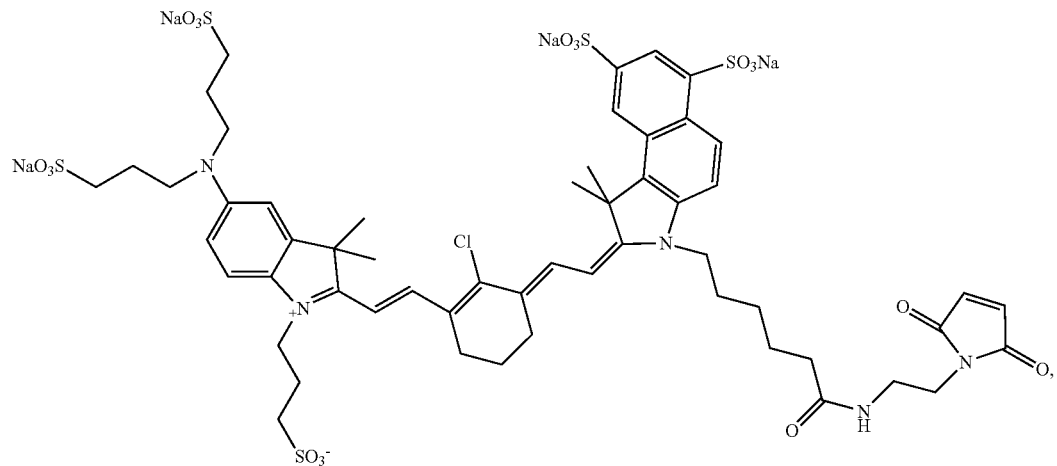
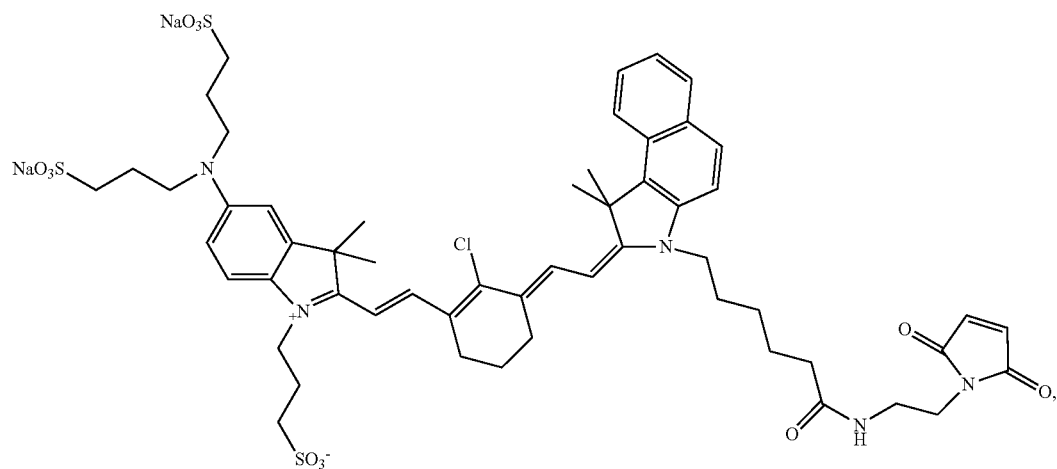
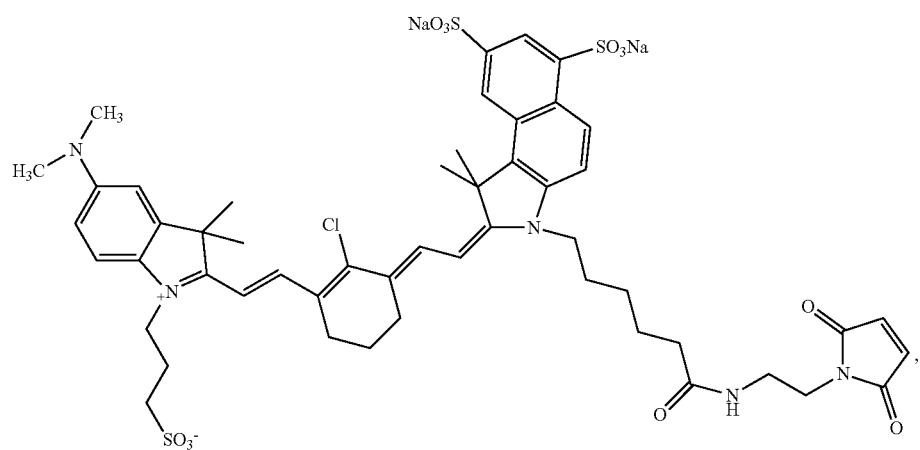

-continued
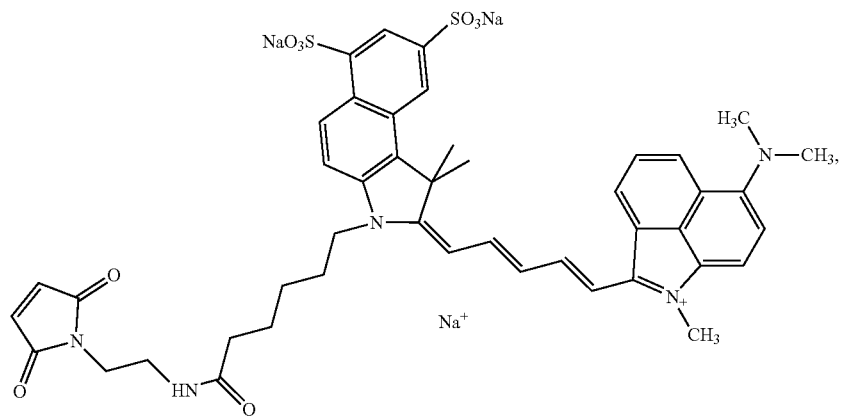
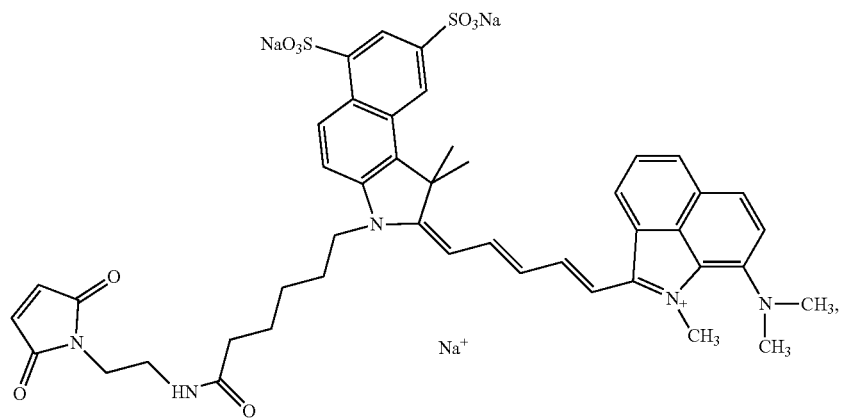
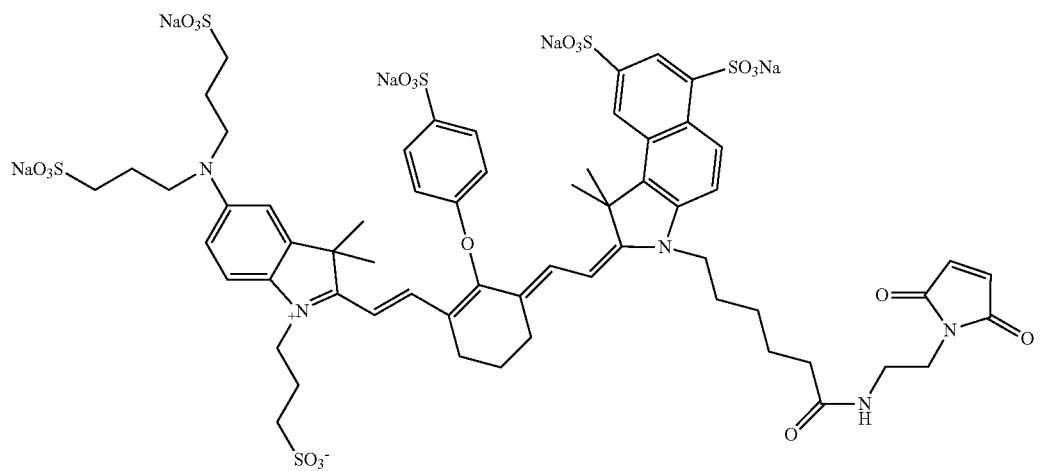

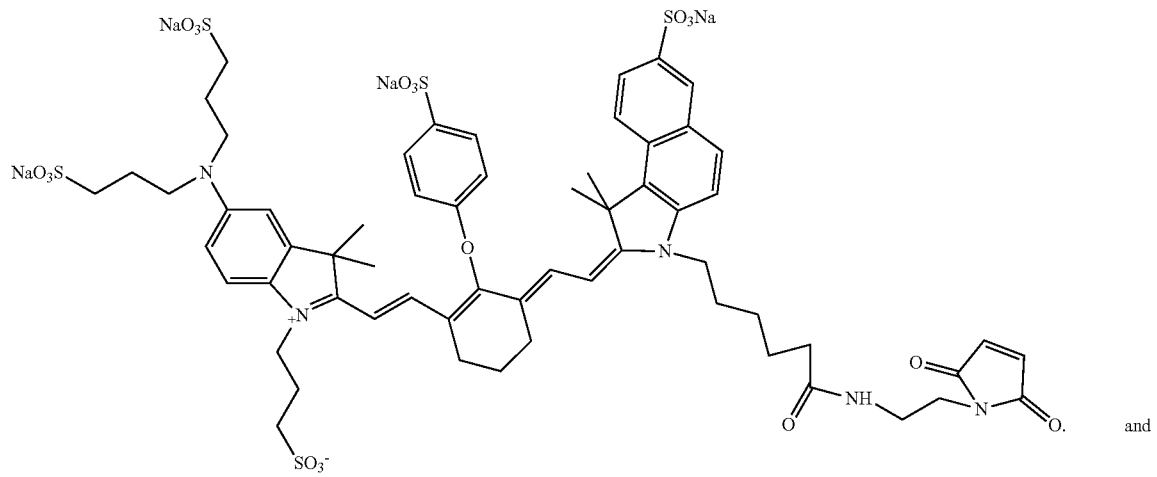

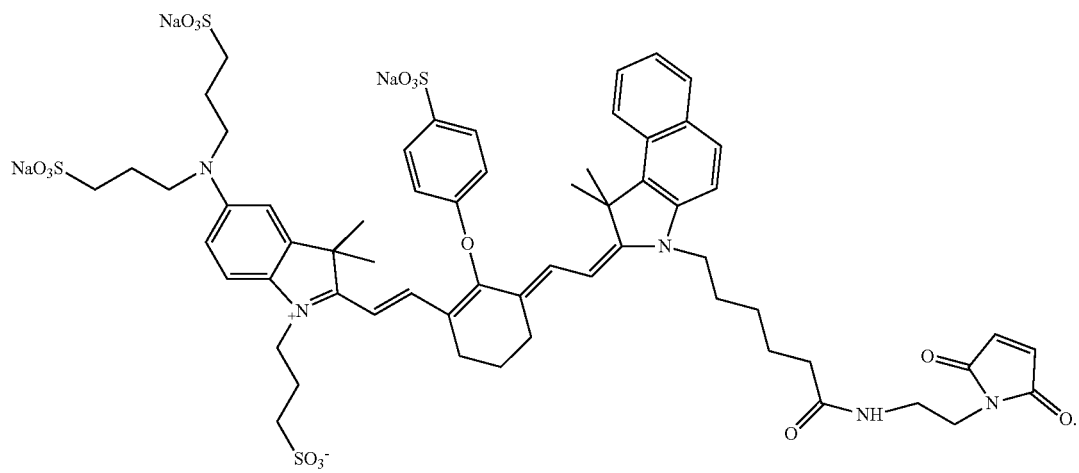

Synthesis of Compounds of the Invention:

The compounds having formula I can be made using conventional methods known in the literature. See for example, G. E. Ficken, *Cyanine Dyes, in Chemistry of Cyanine Dyes*, 211-341 (Venkataraman, ed., 1971); D. M. Sturmer, *Synthesis and Properties of Cyanine and Related Dyes, in The Chemistry of Heterocyclic Compounds*, 441-601 (A. Weissberger and E. C. Taylor, eds, 1977); U.S. Pat. Nos. 4,337,063, 4,404,289, 4,981,988, and 6,048,982 and reference cited therein. For example, the compounds having formulae I-Id can be prepared in accordance to the general scheme outlined in Schemes I and II. In Schemes I and II, the variables R, R', R''' are all non-interfering substituents; and X is a heteroatom or a substituted carbon atom.

In Scheme I, the cyanine dye is prepared by reacting two equivalents of an indolinium salt (i) with one equivalent of bis-imine compound (ii) to yield a cyanine dye (iii).

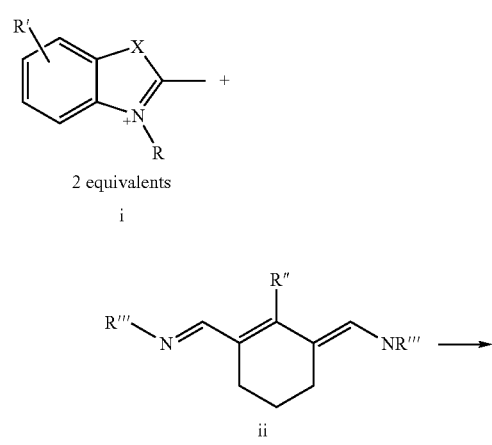

Scheme I

-continued

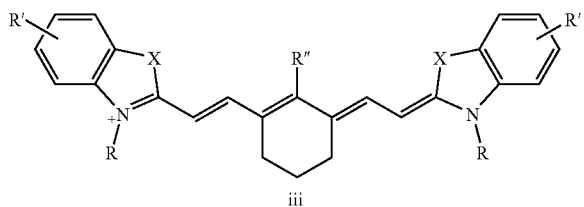

iii

In Scheme II, the cyanine dye is prepared by reacting a benzoindolinium salt (iv) with a N-acetylimine derivative (v) to yield the cyanine dye (vi).

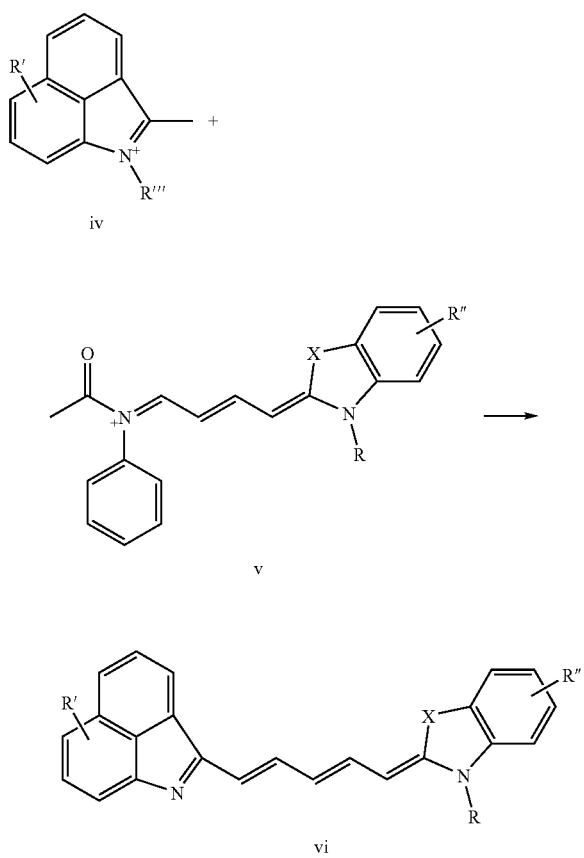

Schemes I and II simply illustrate two synthetic approaches by which the cyanine dyes of the invention can be prepared. It is understood that a skilled artisan practicing the present invention will readily recognized modifications to the above schemes that would provide other compounds having the physical properties that are within the scope of the present invention. For example, while Scheme I illustrates the synthesis of cyanine dyes (iii) of the invention using 2 equivalents of the same indolium salt (i), a skilled artisan will recognize that two different indolium salts having the formula I, can be used to prepare a non-symmetrical cyanine dye of the invention (iii) with different indolium groups. As another example, a skilled artisan would recognize that using the absorption/emission wavelengths of the dye can be modulated by adjusting the length of the polymethine chain and selecting the appropriate aryl or heteroaryl groups (e.g., indole vs. benzindole). As another example, a skilled artisan would recognize that the extinction coefficient and fluorescence intensity of the dye can be varied by adjusting the rigidity of the polymethine chain (e.g., by introducing a ring system into the polymethine chain such as cyclohexene, cyclobutenone, among others). As such, a skilled artisan would be able to modify the synthesis by selecting the appropriate reagents to make dyes having the varied physical properties.

B. Reporter-Quencher Dye Pairs

The essentially non-fluorescent (ENF) quenchers of the present invention when used with a complementary reporter dye can participate in an energy transfer process. More particularly, the ENF quenching dyes of the present invention accept energy from a wide variety of complementary reporter dyes provided that the quenching and the reporter dyes are in proximity for quenching to occur, and that at least some spectral overlap occurs between the emission wavelengths of the reporter dye and the absorption band of the quenching dye. Preferably, the absorption spectra of the quencher dyes of the invention have good overlap with the emission spectra of most near-infrared fluorophores. This overlap may occur with the emission of the reporter group occurring at a lower or even higher wavelength emission maximum than the maximal absorbance wavelength of the quenching compound, provided that sufficient spectral overlap exists.

In another embodiment, the quencher dye of the present invention is used to quench the fluorescence emission of a reporter dye that has an emission wavelength in the near infrared region of about 650 nm to about 900 nm. Examples of suitable reporter dyes that can be used with the quencher dyes of the present invention include, but are not limited to, Alexa Fluor® 647, Alexa Fluor® 660, Alexa Fluor® 680, Alexa Fluor® 700, Alexa Fluor® 750, ATTO 680, ATTO 700, DY-647, DY-650, DY-673, DY-675, DY-676, DY-680, DY-681, DY-682, DY-690, DY-700, DY-701, DY-730, DY-731, DY-732, DY-734, DY-750, DY-751, DY-752, DY-776, DY-781, DY-782, DY-831, La Jolla Blue, Cy5, Cy5.5, Cy7, IRDye® 800CW, IRDye® 38, IRDye® 800RS, IRDye® 700DX, IRDye® 680, among others. "Alexa Fluor" dyes are available from Molecular Probes Inc., Eugene, Oreg., U.S.A. (www.probes.com). "ATTO" dyes are available from ATTO-tec GmbH, Siegen, Germany (www.atto-tec-.com). "DY" dyes are available from Dyomics GmbH, Jena, Germany (www.dyomics.com). La Jolla Blue is available from Hyperion Inc. "Cy" dyes are available from Amersham Biosciences, Piscataway, N.J., U.S.A., (www.amersham-.com). "IRDye® infrared dyes" are available from LI-COR® Bioscience, Inc., Lincoln, Nebr., U.S.A (www.licor.com).

An additional group of near-infrared reporter dyes that can be used with the quencher dye of the present invention are dyes described in U.S. patent application Ser. No. 10/354,812 (incorporated herein by reference, in its entirety, for all purposes), having formula II:

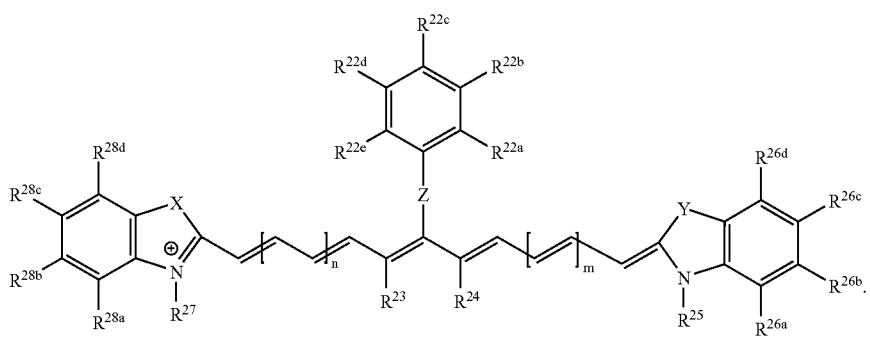

II

In formula II, the symbol Z is O, S, or $NR^{29}$ wherein $R^{29}$ is H or alkyl.

$R^{22a-22e}$ in formula II are each independently H, alkyl, halo, carboxyl, amino, or $SO_3Cat^+$, wherein $Cat^+$ is a cation and at least one of $R^{22a-22e}$ is $—SO_3Cat^+$.

The symbols $R^{23}$ and $R^{24}$ in formula II are each H, alkyl, sulfonato or optionally, together with the

group to which they are bonded, form a ring, the ring being optionally substituted. m and n are each independently an integer from 0 to 5.

X and Y are $CR^{30}R^{31}$, wherein $R^{30}$ and $R^{31}$ are each independently alkyl, or optionally form a 5- to 7-membered carbocyclic ring together with the carbon atom to which they are bonded.

$R^{25}$ and $R^{27}$ are each independently alkyl, $(CH_2)_rR^{32}$ or $(CH_2)_rR^{33}$; wherein at least one of $R^{25}$ and $R^{27}$ is $(CH_2)_rR^{33}$ and wherein r is an integer from 1 to 50, and $R^{32}$ is a functional group that does not directly react with a carboxyl, hydroxyl, amino, or a thiol group on a biomolecule, and $R^{33}$ is a linking group selected from the group consisting of mercapto, amino, haloalkyl, phosphoramidityl, N-hydroxy succinimidyl ester, sulfo N-hydroxy succinimidyl ester, isothiocyanato, iodoacetamidyl, maleimidyl and an activated carboxylic acid.

$R^{26a-26d}$ and $R^{28a-28d}$ are each independently hydrogen, alkyl, halo, amino, sulfonato, $R^{34}COOH$, $R^{34}OR^{35}$, $R^{34}SR^{35}$, or $R^{34}COOR^{35}$ wherein $R^{34}$ is a bond or alkylene and $R^{35}$ is alkyl, or optionally $R^{26c}$ and $R^{26d}$ together with the atoms to which they are bonded form an aromatic ring, or optionally $R^{28c}$ and $R^{28d}$ together with the atoms to which they are bonded form an aromatic ring.

C. Fluorescence Quenching

Fluorescence quenching can occur through Fluorescence Resonance Energy Transfer (FRET) between a donor (reporter) and acceptor (quencher) of the invention. The principle of FRET is described in for example, U.S. Pat. No. 4,996,143 and in WO 99/64519, both of which are incorporated herein by reference. FRET occurs through the mechanism of long-range dipole-dipole interaction of an initially excited reporter to a quencher. The rate of energy transfer depends on many factors that include the extent of spectral overlap of the reporter's emission spectrum and the quencher's absorption spectrum, the quantum yield of the reporter, the extinction coefficient of the quencher, and particularly strongly dependent on the reporter to quencher distance with is optimally between about 10-100 Å.

Any reporter group with sufficient spectral overlap with a quenching dye of the invention is a suitable reporter for any of the applications described in the present invention. The greater the degree of overlap, the greater the overall quenching observed in a given reporter-quencher distance within the FRET range. While fluorescent dyes are preferred for energy transfer applications, any emission that generates light having sufficient spectral overlap with the quenching dyes is also useful, such as chemiluminescence, or phophorescence, whether by FRET or by triplet state to singlet state transfer.

Aside from FRET, any combination of molecular orientation and spectral coincidence that results in quenching of fluorescence is a also a useful mechanism for quenching by the dyes of the invention, as described herein. For example, efficient quenching can occur even in the absence of spectral overlap if the reporter group and the quenching dye are sufficiently close to together to form a ground state complex, e.g., static or contact quenching (see, Tyagi, et al., Nature Biotechnology, 10, 49 (1998)).

Figure 2:
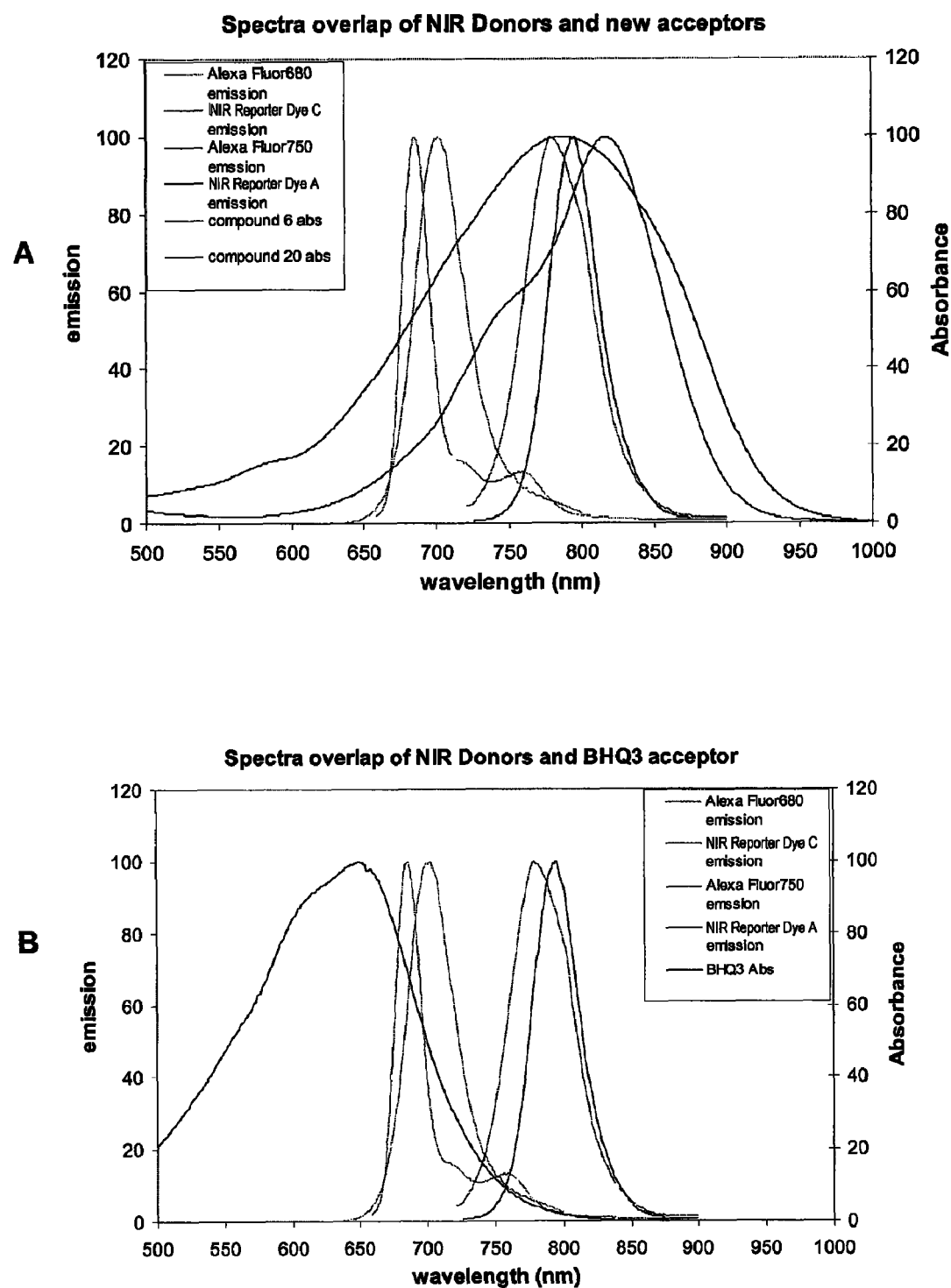
FIG. 2A shows the spectral overlap of the absorbance spectra of quenchers 6 and 20 and the emission spectra of some commonly used near-IR fluorophore reporter dyes.
FIG. 2B shows the spectral overlap of absorbance spectrum of a quencher dye (BHQ-3) and the emission spectra of some commonly used near-IR fluorophore reporter dyes.

As shown in FIG. 2A, the quenching dyes of the invention show extremely good overlap of their absorbance spectra with the emission spectra of commonly used near IR fluorophore reporters such as Alexa Fluor® 680, NIR Reporter Dye C, Alexa Fluor® 750, and NIR Reporter Dye A. FIG. 2B shows the overlap of the absorbance spectra of the quencher dyes of the present invention as compared to another currently commercially available quencher dye that absorbs at near-IR wavelengths, such as BHQ-3 (Black Hole Quencher-3) available from Biosearch Technologies, Novato, Calif., U.S.A. The extremely good spectral overlap of the dyes of the invention can result in high efficiency of quenching of the fluorescence of the reporter dye through FRET mechanism. The quencher dyes of the present invention typically can efficiently quench most all near infrared reporter dyes through FRET because of their broad absorption spectra covering the NIR region (about 650 nm to about 900 nm).

Fluorescence quenching can also occur among fluorescent (reporter) dyes without the presence of any quencher dyes. For example, a flexible peptide conjugated with two identical fluorophores could have sufficient freedom of movement by the peptide structure to allow the dye molecules to dimerize or stack as described in U.S. Pat. Nos. 5,605,809; 5,714,342; 6,037,137; and 6,787,329. Such stacking will substantially reduce the fluorescence of the dye-conjugated peptide by the formation of, for example, molecular exciton (Packard, B. Z. et al. *Proc. Nat; Acad. Sci. USA*, 93, 11640-11645, 1996). Small proteins, such as BSA or casein, when conjugated with a sufficient number of reporter dyes can become substantially non-fluorescent (U.S. Pat. No. 5,719,031; Jones, L. J., *Anal. Biochem.* 251, 144-152, 1997). The homo-FRET process among the proximate reporter dyes on the protein and/or dye aggregation is the primary explanation for the quenching phenomenon.

III. Labeled Substrates

A. Conjugated Substrates

The present invention also provides near-infrared (NIR) dye conjugated substrates. In one aspect, the NIR dye conjugated substrate is a biomolecule comprising an essentially non-fluorescent quencher dye of Formula I and a NIR reporter dye conjugated thereto. In another aspect, the NIR dye conjugated substrate is a biomolecule or ligand comprising only an essentially non-fluorescent dye. In yet another aspect, the NIR dye conjugated substrate is a protein comprising a plurality of NIR reporter dyes to an extent such that fluorescence quenching occurs and is a substantially non-fluorescent substrate.

Near-infrared dye(s) of the present invention can be attached to a biomolecule or a ligand to form a conjugated substrate. Attachment can be for example, by covalent bonding, ionic bonding, and other forms of molecular bonding. For example, useful conjugated substrates of the invention include, but are not limited to, conjugates of antigens, small molecules, steroids, vitamins, drugs, haptens, metabolites, toxins, environmental pollutants, amino acids, peptides, proteins, nucleotides, oligonucleotides, nucleic acids, (nucleic acid polymers) carbohydrates, lipids, ion-complexing moieties, and non-biological polymers. In a preferred embodiment, the conjugated substrate is an amino acid, a peptide, protein, nucleotide, oligonucleotide, nucleic acid polymer or an ion-complexing moiety.

In one embodiment, the conjugated substrate is a natural or synthetic amino acid; a natural or synthetic peptide or protein; or an ion-complexing moiety. Preferred peptides include, but are not limited to, protease substrates, protein kinase substrates, phosphatase substrates, neuropeptides, cytokines and toxins. In certain embodiments, the preferred peptide is a protease substrate. Preferred protein conjugates include enzymes, antibodies, lectins, glycoproteins, histones, alumin, lipoproteins, avidin, streptavidins, protein A, protein G, casein, phycobiliproteins and other fluorescent proteins, hormones, toxins, growth factors and the like.

In yet another embodiment, the conjugated substrate is an ion-complexing moiety. The ion-complexing moiety can either be a paramagnetic or diamagnetic metal ion (e.g., $Ga^{3+}$, $Fe^{3+}$, $Lu^{3+}$, $Sc^{3+}$) that has a chelating group optionally coordinated thereto. The ion-complexing moiety can be an organic cation or anion, such as amino acids, nucleic acids, acrylic acids, carboxylic acids, amines, sulfonic acids, phosphoric acids, a cationic/anionic polymer (e.g., a polylysine, polyacrylic acid polymer) or a quaternary ammonium ion, among others.

In one embodiment, the ion-complexing moiety is a diamagnetic metal ion. The quencher dye of the invention can be attached to the ion-complexing conjugate either directly to the metal ion or through a chelating group coordinated to the metal ion. Ion-complexing conjugates are useful in monitoring biological assay reactions, for example, they can bind to a cationic or anionic functional group on a reporter dye-labeled biomolecule, to bring the quencher dye in proximity to the reporter dye on the biomolecule and quenching its fluorescence, to result in the detection of the biomolecule. Preferably, the ion-complexing moiety itself does not quench the fluorescence of the reporter dye-labeled biomolecule.

In yet another embodiment, the conjugated substrate is a natural or synthetic nucleic acid base, nucleoside, nucleotide or a nucleic acid polymer, including those that are modified to possess an additional linker (see, for example, U.S. Pat. Nos. 5,047,519 and 4,711,955, incorporated herein by reference) for the attachment of the quencher dye compounds of the invention. The conjugated nucleotide is preferably a nucleoside triphosphate, a deoxynucleoside triphosphate, or a dideoxynucleoside triphosphate.

Preferred nucleic acid conjugates are labeled single- or multi-stranded, natural or synthetic DNA or RNA, DNA or RNA oligonucleotides, or DNA/RNA hybrids, or incorporate an unusual linker such as morpholine derivitized phosphates (AntiVirals, Inc., Corvallis, Oreg., U.S.A), or peptide nucleic acids such as N-(2-aminoethyl)glycine units.

In yet another embodiment, the conjugated substrate is a carbohydrate that is a natural or synthetic polysaccharide such as a dextran, FICOLL, heparin, glycogen, amylopectin, mannan, insulin, starch, agarose and cellulose, and the like. Alternatively, the conjugated substrate is a polysaccharide that is a lipopolysaccharide. Preferred polysaccharide conjugates are starch or FICOLL conjugates.

In yet another embodiment, the conjugated substrate is a lipid, preferably a glycolipid, a phospholipid, a sphingolipid, a glyceride, a steroid, and the like. When the lipid is a phospholipid, the compound of the invention is preferably incorporated in the polar head group of the lipid. Alternatively, the conjugated substance is a lipid assembly, such as a liposome or a lipid droplet.

In a preferred embodiment, the conjugated substrate of the invention is selected from the group consisting of nucleotides, nucleosides, proteins, peptides and amino acids.

In certain embodiments, the conjugated substrates of the invention are preferably polypeptides or proteins that are a protease substrate. In one aspect, the conjugated substrate is preferably a polypeptide or protein comprising at least one quencher dye having formula I and at least one complementary near-infrared reporter dye, such that the action of the protease enzyme cleaves the polypeptide or protein, resulting in the restoration of fluorescence.

In one embodiment, the conjugate is a protein or peptide substrate (P) for identifying proteolytic cleavage, wherein the substrate comprises (i) an essentially non-fluorescent quencher group (Q) having an absorption wavelength of about 650-900 nm; and (ii) a fluorescent reporter group (R) having an emission wavelength of about 650-900 nm. In one preferred embodiment, the reporter dye that is used to conjugate to (P) has formula II. In another embodiment, the reporter dye having formula II is selected from the group consisting of:

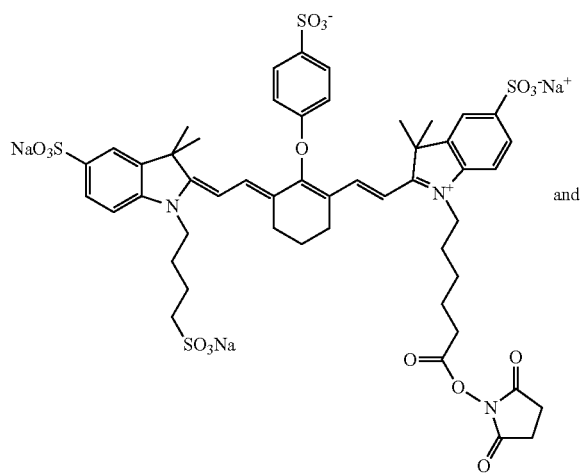

NIR Reporter Dye A and

-continued

NIR Reporter Dye B

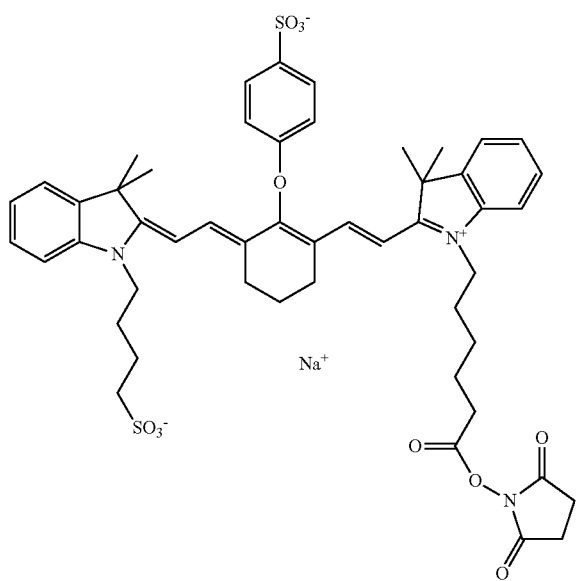

The reporter and the quencher dye can be each independently attached to the peptide or protein substrate (P) through an amino acid side chain, or the N- or C-terminus of the peptide or protein substrate. In certain embodiments, the quenching group is a cyanine dye having a formulae I-Id.

The conjugated peptide or protein substrate can be used with a variety of proteases. Suitable proteases include, but are not limited to, HCV protease, HIV protease, HIV-1 protease, CMV protease, secretase, β-secretase, BACE-1, capase, ADAM protease, matrix metalloprotease, cathepsin, bromolain, chymotrypsin, collagenase, elastase, kallikrein, papain, pepsin, plasmin, renin, streptokinase, substilisin, thermolysin, thrombin, trypsin, urokinase, and the like.

A specific embodiment of a conjugated biomolecule of the invention is the HIV-1 protease substrate having structure III (SEQ ID NO:1):

III
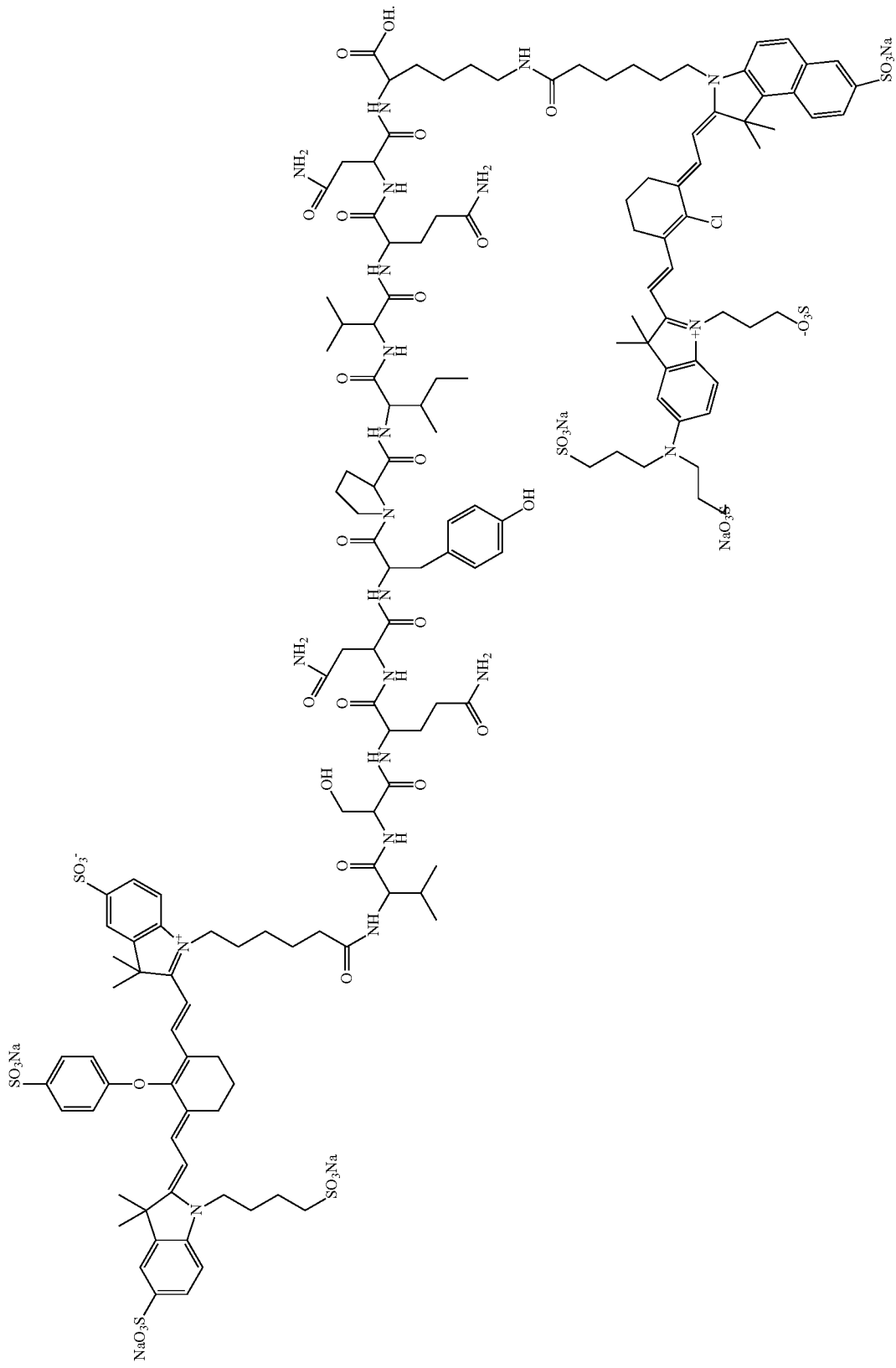

In another embodiment, a conjugated biomolecule is the β-secretase (β-amyloid converting enzyme (BACE-1)) protease substrate having the structure IV (SEQ ID NO:5):

dyes are the reporter dyes having formula II. In another embodiment, the plurality of near-infrared reporter dyes are those that absorb at a wavelength of about 650-900 nm. In one

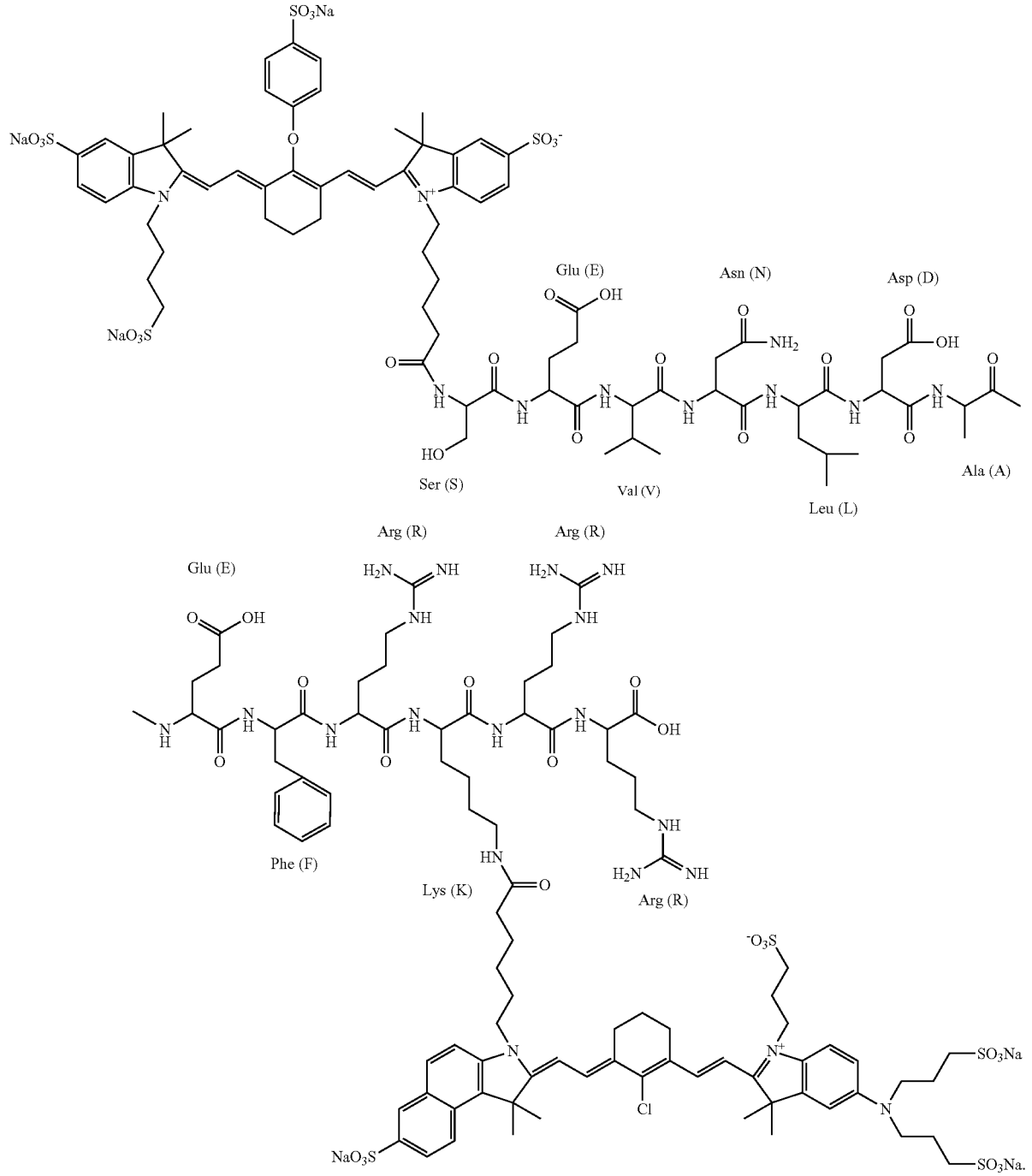

IV

In another aspect, the conjugated substrate is a protein having attached thereto a plurality of near-infrared reporter groups, wherein the dye-conjugated protein is substantially non-fluorescent. Within this aspect, the plurality of reporter groups that are conjugated to the protein are preferably near-infrared dye compounds, which may be the same or different. In one embodiment, the plurality of near-infrared reporter embodiment, the protein is casein or BSA. In another embodiment, the protein is for example, a protein derived product such as gelatin.

In certain embodiments, the dye conjugated protein substrate has a molecular weight of at least 5 kD, and has attached thereto, a plurality of fluorescent near-infrared reporter dyes of formula II, such that the dye conjugate protein is substantially non-fluorescent. As used herein, the term "substantially non-fluorescent" when used to describe a dye conjugated substrate includes when the dye conjugated substrate exhibits fluorescence quenching of at least about 50%-60%, preferably about 60% to about 75%, and more preferably about 75% to about 97%, such as about 80%, 90% and 95% percent fluorescent quenching relative to the dye molecule that is unconjugated.

In certain other embodiments, the dye conjugated protein substrate has a molecular weight of at least 5 kD, and has attached thereto, a plurality of fluorescent near-infrared reporter dyes that absorbs at a wavelength of about 650-900 nm, in which the conjugated dye on the protein substrate exhibits fluorescence quenching greater than or equal to 90 percent relative to the reporter dye that is non-conjugated. In certain aspects, the protein is preferably casein or BSA. In one embodiment, the near infrared reporter dye is preferably a near infrared reporter dye having formula II.

In certain other embodiments, the dye conjugated substrate is preferably a protein substrate for proteolytic cleavage having a molecular weight of between about 19-70 kD and having a plurality of near-infrared reporter dyes of formula II attached thereto, resulting in a dye conjugated protein that is substantially non-fluorescent. Such a substantially non-fluorescent protein conjugate is useful, for example, as a generic protease substrate to detect the activity of a variety of proteases. In one embodiment, the conjugated protein substrate is preferably a NIR fluorescent (reporter) dye-conjugated casein.

In certain aspects, the casein substrate of the invention has attached thereto a plurality of NIR Reporter Dye B (shown below), wherein the wavy line, ～, that intersect the single bond denotes the point of attachment of the that bond of NIR Reporter Dye B to the substrate.

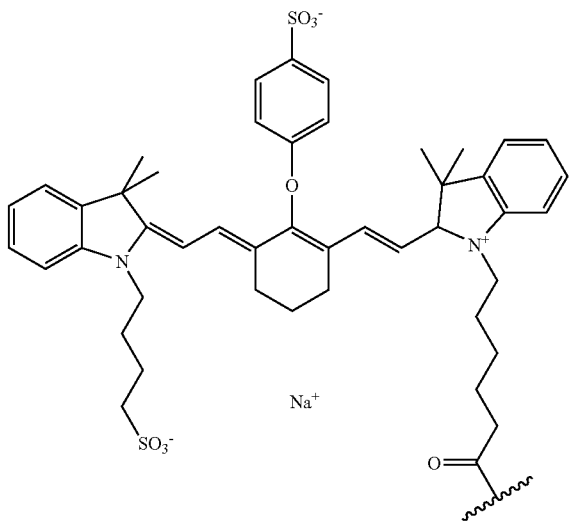

Preparation of Labeled Substrates

Many methods of linking dyes to various types of biomolecules are well known in the art. For a thorough discussion on how various linking groups on the quencher dyes having formulae I-Id (or optionally, reporter dyes having formula II) can be attached to respective complementary functional groups on a biomolecule, see R. Haughland, *The Handbook—A Guide to Fluorescent Probes and Labeling Technologies*, 9th Edition, 2002, Molecular Probes, Inc. and the references cited therein; and Brindley, 1992, *Bioconjugate Chem.* 3:2.

For example, the presence of an electrophilic NHS ester linking group on the quencher or reporter dye enables the dye to react with a nucleophilic group on the biomolecule, e.g., an amino group on a protein or peptide substrate, to form a covalent amide bond. Also, the presence of an electrophilic maleimide linking group on the quencher dye enables the dye to form a covalent bond with a nucleophilic group such as a thiol group on a biomolecule. Typically, the reaction to prepare the labeled substrate is performed by combining the dye and the biomolecule in a suitable solvent (e.g, DMF, DMSO, water), with optional inclusion of additional reagents such as an acid or base catalyst.

Alternatively, the presence of a nucleophilic linker group on the quencher or reporter dye, such as an amino group, enables the dye to react with a biomolecule containing an electrophilic activated carboxylic acid group, resulting in a stable peptide linkage. The nucleophilic amino linking group also can be reacted with an electrophilic carbonyl group on the biomolecule to result in the formation of Schiffs base products.

Moreover, if the quencher dye or reporter dye has a nucleophilic hydroxy linking group, then is may be attached to a biomolecule, such as DNA or RNA, through phosphoramidite chemistry. For examples of nucleotide and oligonucleotide labeling methods, see U.S. Pat. No. 6,027,709, incorporated herein by reference, which discloses many preferred linking groups, linking methods, and biomolecules that can be readily labeled. The use of the phosphoramidite linking group allows labeling of the DNA or RNA during the synthesis process. The protected nucleotide is labeled while attached to a solid phase support. The free 5'-OH group is reacted with the quencher dye containing a phosphoramidite linker and a tetrazole activator to form a phosphite linkage which subsequently is oxidized to a phosphate linkage. The labeled DNA or RNA is then cleaved from the solid phase using ammonia or other standardized procedure.

Additionally, the quencher dye or reporter dye of the invention may also be covalently attached to DNA or RNA via one or more purine or pyrimidine bases through an amide, ester, ether or thioether bond; or is attached to the phosphate or carbohydrate by a bond that is an ester, thioester, amide, ether or thioether. Alternatively, the quencher dye of the invention may be bound to the nucleic acid by chemical post-modification, such as with platinum reagents, or using a photoactivatable molecule such as a conjugated psoralen.

The quencher dyes or reporter dyes of the invention can also be attached, for example, to analogs of nucleotide triphosphates (dNTPs and ddNTPs) to provide a reagent for enzymatic labeling of various DNA molecules and for facilitating their detection with an automated DNA sequencing and analysis system. DNA sequencing reaction products can be labeled internally by performing limited polymerization utilizing the labeled dNTP as the sole source of a particular deoxynucleotide prior to a dideoxy-specific termination reaction. PCR products also can be labeled fluorescently by the addition of limited quantities of the labeled dNTP to the amplification reaction.

Additional methods of labeling oligonucleotides are described in U.S. Pat. No. 6,750,024, incorporated herein by reference. Also, for a thorough review of oligonucleotide labeling procedures, see R. Haughland in *Excited States of Biopolymers*, Steiner ed., Plenum Press (1983), *Fluorogenic Probe Design and Synthesis: A Technical Guide*, PE Applied Biosystems (1996), and G. T. Herman, *Bioconjugate Techniques*, Academic Press (1996).

The preferred methods of labeling a biomolecule are those in which a linking group on a quencher dye or reporter dye of the invention reacts with a thiol, a hydroxyl, a carboxyl, or an amino group on a biomolecule, resulting in the formation of a covalent attachment between the compounds of formula I or formula II and the biomolecule. This reaction is preferably carried out in aqueous buffer having an optional co-solvent, such as DMSO or DMF at pH 8 to 9.

In one embodiment, the reporter and quencher dyes may be linked to a peptide or protein, for example, by conjugating the quencher dye through the linking group to the side chain of the amino acid or the C- or N-terminus of a protein or peptide.

Biomolecules can be labeled according to the present invention using a kit. In a preferred embodiment, the kit comprises a dye of formula I, and a buffer. Preferably, the kit contains a coupling buffer such as $KH_2PO_4/K_2HPO_4$ buffer (pH~7.0). Preferably, the buffer has a qualified low fluorescence background. In one embodiment, the kit further comprises a reporter dye having formula II. In yet another embodiment, the kit comprises only a reporter dye of formula II.

Optionally, the kit can contain a purification sub-kit. After labeling a biomolecule with one of the preferred dyes, the labeled biomolecule may be separated from any side reaction products and any free hydrolyzed product resulting from normal hydrolysis. For biomolecules containing 13 or fewer amino acids, preparative thin layer chromatography (TLC) can remove impurities.

For larger biomolecules such as larger peptides or proteins, a Sephadex G-15 or G-25 resin may remove unwanted derivatives. Panvera supplies a gel filtration of proteins kit, which is designed to separate dye-labeled peptides and proteins from free dye. The dye-labeled biomolecules that remain after desalting can often be used successfully without further purification. In some cases, it may be necessary to resolve and assess the activity of the different dye products using HPLC or conventional chromatography.

IV. Methods of Use

The present invention provides methods of using NIR quencher dyes and NIR-labeled biomolecules or ligands as biological probes in biological assays.

In one aspect of the invention, the quencher dyes of formula I are useful in any application where energy transfer from a fluorescent reporter group to a non-fluorescent quencher has been previously described, preferably when some spectral overlap exists between the emission of the reporter dye and the absorbance of the quencher dye of the invention. Typically, the quencher compounds are used in combination with a reporter dye in a biological assay that detects a change in separation distance between the reporter dye and the quencher compound.

The quencher compounds of the invention are highly efficient at quenching the fluorescence of a complementary reporter dye. In one embodiment, when a reporter-quencher dye pair of the invention is separated beyond the distance where energy transfer from the reporter to the quencher can occur, the fluorescence of a reporter dye is increased at least 5-fold. In another embodiment, the fluorescence of the complementary reporter dye is increased at least 15-fold. In still yet another embodiment, the fluorescence of the complementary reporter dye is increased at least 25-fold. In yet another embodiment, the fluorescence of the complementary dye is increased at least 30-fold.

A. Applications in Biological Assays

As stated above, the NIR quencher dyes and NIR reporter dyes can be conjugated to a substrate to form NIR-labeled biomolecules or ligands of the invention, which can be used as probes in bioassays.

For example, an assay that relies upon the measurement of the proximity of a fluorescent reporter dye and a quencher compound in a system can be carried out using quencher and reporter compounds as described herein. Assays of this type can be used to detect and/or quantify an increase/decrease in the separation distance between a fluorogenic reporter dye and a quenching compound.

In one embodiment, an assay can be used to detect molecular or structural assembly. In yet another embodiment, an assay can be used to detect a conformational or a chemical change in a molecule, macromolecule or structure.

For instance, the fluorescence of a reporter dye can be quenched upon being placed in proximity to a quencher compound as described herein. This approach is particularly useful in kinase assays. In a kinase assay, a reporter dye-conjugated molecule, that is, the phosphorylated product which is produced from the phosphorylation of a tyrosine, serine, or threonine containing biosubstrate by a kinase, can bind to a phosphate-specific ion-complexing group having a quencher dye of formula I conjugated thereto, or to a phospho-specific antibody such as p-Tyr-100 (Cell Signaling Technology) having a quencher dye of formula I conjugated thereto; to bring the reporter and quencher dye molecules in proximity, and results in the observed quenching of the reporter dye's fluorescence. Other exemplary systems which can be analyzed include: protein subunit assembly; enzyme-mediated protein assembly; molecular dimensions of proteins; membrane-protein interactions; protein-protein interactions; protein-protein-nucleic acid complex assembly; receptor/ligand interactions; immunoassays; nucleic acid hybridizations; quantitative detection of specific DNA sequence amplification; detection of DNA duplex winding; nucleic acid-protein interactions; nucleic acid-drug interactions; primer extension assays for mutation detection; reverse transcriptase assay; strand exchange in DNA recombination reactions; membrane fusion assays; transmembrane potential sensing; and ligation assays.

In one embodiment, specific binding pair members labeled with a quenching compound can be used as probes for the complementary member of that specific binding pair. The complementary member is typically labeled with a fluorescent reporter dye and association of the two members of the specific binding pair results in quenching of fluorescence. This assay is particularly useful in nucleic acid hybridization assays, evaluation of protein-nucleic acid interaction, and in immunoassays.

In another embodiment, a loss of fluorescence indicates the association of an enzyme with an enzyme substrate, agonist or antagonist, such that the fluorophore on one member of the interacting pair is brought into proximity to a quenching compound on the other. Exemplary specific binding pair members include proteins that bind non-covalently to low molecular weight ligands (including biotin), oligonucleotides, and drug-haptens. Representative specific binding pairs include: antigen/antibody; biotin/avidin, streptavidin, anti-biotin; folate/folate-binding protein; IgG/protein A or protein G; drug/drug receptor; toxin/toxin receptor; carbohydrate/lectin or carbohydrate receptor; peptide/peptide receptor; protein/protein receptor; peptide nucleic acid/complementary strand; enzyme/substrate; DNA or RNA/cDNA or cRNA; hormone/hormone receptor; and ion/chelator.

Alternatively, a monomer, labeled with a quenching compound can be incorporated into a polymer labeled with a reporter dye, resulting in quenching of fluorescence. For example, a nucleotide conjugated to a quencher can be incorporated via the polymerase chain reaction into a double stranded DNA molecular that is labeled with a reporter dye.

In a preferred embodiment, the initially quenched fluorescence of a reporter dye (e.g. compound having formula II) associated becomes dequenched upon being released from the constraint of being in proximity to a quenching compound (e.g., compound of formula I). The quenching compound is optionally associated with the same molecular structure as the reporter dye, or the reporter and quencher are associated with adjacent, but distinct subunits of the structure. The following systems, among others, can be analyzed using dye pairs to detect and/or quantify structural disassembly: detection of protease activity using fluorogenic substrates (e.g., HIV protease assays); detection of enzyme-mediated protein modification (e.g., cleavage of carbohydrates/fatty acids, phosphates, prosthetic groups); immunoassays (via displacement/competitive assays); detection of DNA duplex unwinding (e.g. helicase/topoisomerase/gyrase assays); nucleic acid strand displacement; ds DNA melting; nuclease activity; lipid distribution and transport; and TaqMan® assays.

Structural disassembly is typically detected by observing the partial or complete restoration of fluorescence, as a conjugated substance is exposed to a degradation conditions of interest for a period of time sufficient for degradation to occur. A restoration of fluorescence indicates an increase in separation distance between the dye pair, e.g., reporter dye and quenching compound, or between two reporter dyes, and therefore a degradation of the conjugated substance. If the detectable difference in fluorescence is detected as the degradation proceeds, the assay is a continuous assay. Since most enzymes show some selectivity among substrates, and as that selectivity can be demonstrated by determining the kinetic differences in their hydrolytic rates, rapid testing for the presence and activity of the target enzyme is provided by the enhancement of fluorescence of the labeled substrate following separation from the quenching compound.

In another embodiment, a single-stranded oligonucleotide signal primer is labeled with both a quenching compound and a fluorescent reporter dye, and incorporates a restriction endonuclease recognition site located between the reporter dye and the quenching compound. The single-stranded oligonucleotide is not cleavable by a restriction endonuclease enzyme, but upon binding to a complementary (target) nucleic acid, the resulting double stranded nucleic acid is cleaved by the enzyme and the decreased quenching is used to detect the presence of the complementary nucleic acid (See, for example, U.S. Pat. No. 5,846,726).

A single nucleotide polymorphism (SNP) can also be detected through the use of sequence specific primers, by detection of melt temperatures of the double stranded nucleic acid. In this aspect, the complementary or substantially complementary strands are labeled with a dark quenching compound and a fluorescent reporter dye, respectively, and dissociation of the two strands (melting) is detected by the restoration of fluorescence of the reporter.

In yet another example, the rupture of a vesicle containing a highly concentrated solution of fluorophores and quenching compounds is readily detected by the restoration of fluorescence after the vesicle contents have been diluted sufficiently to minimize quenching.

The quenching compound and the fluorescent reporter can be present on the same or different substances, and a change in the three-dimensional structural conformation of one or more components of the assay can result in either fluorescence quenching or restoration of fluorescence, typically by substantially decreasing or increasing the separation distance between the quenching compound and a reporter fluorophore. The following systems, among others, can be analyzed using energy transfer pairs to detect and/or quantify conformation changes: protein conformational changes; protein folding; structure and conformation of nucleic acids; drug delivery; antisense oligonucleotides; and cell-cell fusion (e.g. via the diffusion apart of an initial reporter-quenching compound pair). By conformation change is meant, for example, a change in conformation for an oligonucleotide upon binding to a complementary nucleic acid strand. In one assay, labeled oligonucleotides are substantially quenched when in solution, but upon binding to a complementary strand of nucleic acid become highly fluorescent (see, for example, European Patent Application EP 0 745 690). The change in conformation can occur when an oligonucleotide that has been labeled at its ends with a quenching compound and a fluorophore, respectively, loses its G-quartet conformation upon hybridization to a complementary sequence resulting in decreased fluorescence quenching (see, for example, U.S. Pat. No. 5,691,145). Alternatively, the binding of an enzyme substrate within the active site of a labeled enzyme may result in a change in tertiary or quaternary structure of the enzyme, with restoration or quenching of fluorescence.

In a preferred embodiment, the ENF quencher dyes of the invention are useful in monitoring oligonucleotide hybridization reactions. Suitable hybridization assay formats are described U.S. Pat. No. 6,750,024, incorporated herein by reference in its entirety, for all purposes.

In yet another aspect, assays that rely on the measurement of the proximity of a plurality of reporter dyes in a biomolecule may be carried out using the reporter compounds, preferably the reporter compounds having formula II, as described herein. Such assays can be used in, for example, a generic protease assay, to detect the presence of a variety of proteases.

Within certain aspects, the reporter dye on a protein that has a plurality of fluorescent (reporter) dyes conjugated thereto is initially quenched, but becomes dequenched upon proteolytic digestion of the conjugated biomolecule, which results in the release of the reporter dyes from proximity. In one embodiment, the conjugated protein is preferably a NIR fluorescent (reporter) dye-conjugated casein or BSA. In a specific embodiment, the conjugated substrate is casein having conjugated thereto a plurality of fluorescent (reporter) dyes having formula II.

B. Detecting Enzyme Activity

In another embodiment, the ENF quencher dyes of the invention are useful in monitoring the activity of an enzyme. The assay method comprises:

a) providing a substrate with at least one member of a reporter-quencher pair, wherein the quencher is essentially non-fluorescent and absorbs at a wavelength of about 650-900 nm;

b) incubating the substrate with the enzyme to generate a product; and c) detecting the product by monitoring fluorescence at a wavelength of between about 650-900 nm, to detect the activity of the enzyme.

In one embodiment, the reporter dye preferably has an emission wavelength in the NIR region. In one embodiment, the reporter dye used in a method of the present invention is a cyanine dye. The quencher dye used in a method of the invention is an ENF cyanine dye. In one embodiment, the ENF quencher dye used in the method of the invention is a dye having formula I-Id.

Non-limiting examples of enzymes that can be monitored using the assay method outlined above include protease, kinases and phosphatases, and the like.

In one particular aspect, the enzyme is a specific protease. The protease may be selected from the group consisting of HCV protease, HIV protease, HIV-1 protease, CMV protease, secretase, β-secretase, BACE-1 capase, ADAM protease, matrix metalloprotease, cathepsin, bromolain, chymotrypsin, collangenase, elastase, kallikrein, papain, pepsin, plasmin, renin, streptokinase, subtilisin, thermolysin, thrombin, trypsin, urokinase, and the like.

In one embodiment, when the enzyme is a specific protease, the substrate further comprises the second member of a reporter-quencher pair. The reporter-quencher pair is preferably located on opposite sides of the protease cleavage site in the enzyme substrate.

When the biological assay is used to detect proteolytic enzyme activity of a specific protease, the assay may be configured as follows. A reaction mixture is prepared by combining a protease enzyme and an enzyme substrate comprising a near-IR reporter dye and an essentially non-fluorescent near-IR dye attached to opposite sides of the proteolytic cleavage site located on the substrate. Typically, the reaction is performed in a buffer. Optionally, the protease assay medium may comprise putative agonists or antagonists of the protease being studied as to determine the effects of the agonists or antagonist on the activity of the protease (e.g., to determine the $EC_{50}$ or $IC_{50}$ value). The progress of the reaction may be monitored by observing the steady state increase in fluorescence emission at a wavelength of about 650-900 nm due to the fluorescent reporter dye, which is recorded using a spectrofluorimeter or a fluorescent microplate reader.

In one aspect, the increase in fluorescence signal after proteolytic cleavage of the protein or peptide substrate is at least 5-fold. In another embodiment, the increase in fluorescence signal after proteolytic cleavage is at least 15-fold. In still another embodiment, the increase in fluorescence signal after proteolytic cleavage is at least 25-fold. In still yet another embodiment, the increase in fluorescence signal after proteolytic cleavage is at least 30-fold.

In one embodiment, the methods are useful for the detection of HIV protease activity. In a certain aspects, the assay methods are useful for detecting the cleavage of the peptide sequence, VSQNYPIVQNK (SEQ ID NO:4), by HIV-1 protease. The peptide sequence, VSQNYPIVQNK (SEQ ID NO:4), for HIV-1 protease is derived from the natural cleavage site at the junction of the matrix protein (MA) and the capsid protein (CA) on the HIV-1 gag polyprotein (Hazebrouck, S.; Machtelinckx-delmas, V.; Kupiec, J.-J.; Sonigo, P. Biochem J. 358, 505-510, 2001; Beck, Z. Q.; Morris, G. M.; Elder, J. H. Curr. Drug Targets-Infectious Disorders, 2, 37-50, 2002; Matayoshi, E. D.; Wang, G. T.; Krafft, G. A.; Erickson, J. Science, 247(4945), 954-958, 1990). This peptide sequence can be converted to a protease substrate for detection by conjugating with a near-infrared (NIR) fluorescent donor, such as NIR Reporter Dye A, and an essentially non-fluorescent dark quencher, such as Compound 6, through the N-terminal amine group and the lysine amine group (FIG. 16).

Figure 16:
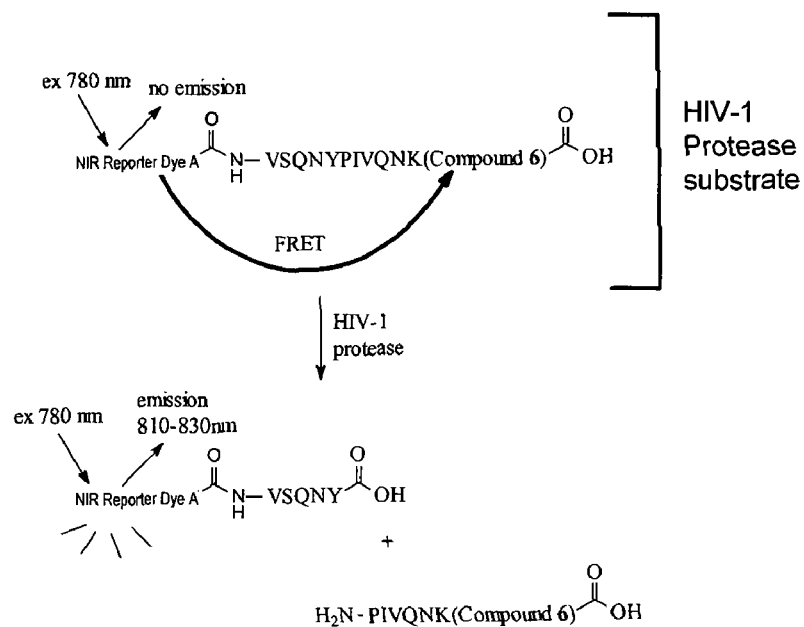
FIG. 16 shows a schematic illustration that outlines a HIV-1 protease assay of the invention (SEQ ID NOS:1-3).

As shown in FIG. 16, the fluorescent reporter dye, i.e., NIR Reporter Dye A, has maximum absorption at 774 nm and maximum fluorescence at 789 nm in a phosphate buffered saline solution. This dye has good aqueous solubility and overall brightness, and its fluorescence is insensitive to the pH and salt concentration. The quenching efficiency of an essentially non-fluorescent quencher dye of the invention, i.e., Compound 6, is high. The detection of protease activity in the near-infrared range (NIR) virtually eliminates background fluorescence, because few molecules have intrinsic fluorescence in this very long wavelength region. Moreover, the background from scattering light in the NIR is dramatically reduced as compared to the use of visible fluorophores.

The reporter-quencher conjugated HIV-1 protease substrate, i.e., (NIR Reporter Dye A)-VSQNYPIVQNK-(Compound 6)-OH (SEQ ID NO:1), shown in FIG. 16 has low fluorescence emission when detected at 820±10 nm with 780 nm excitation due to the efficient quenching of reporter group by the proximate essentially non-fluorescent quencher through, for example, a FRET mechanism. Cleavage of the reporter-quencher HIV-1 protease substrate by HIV-1 protease separates the reporter-quencher pair and restores the fluorescence signal from the reporter dye. The signal generated linearly reflects the degree of substrate conversion.

Figure 17:
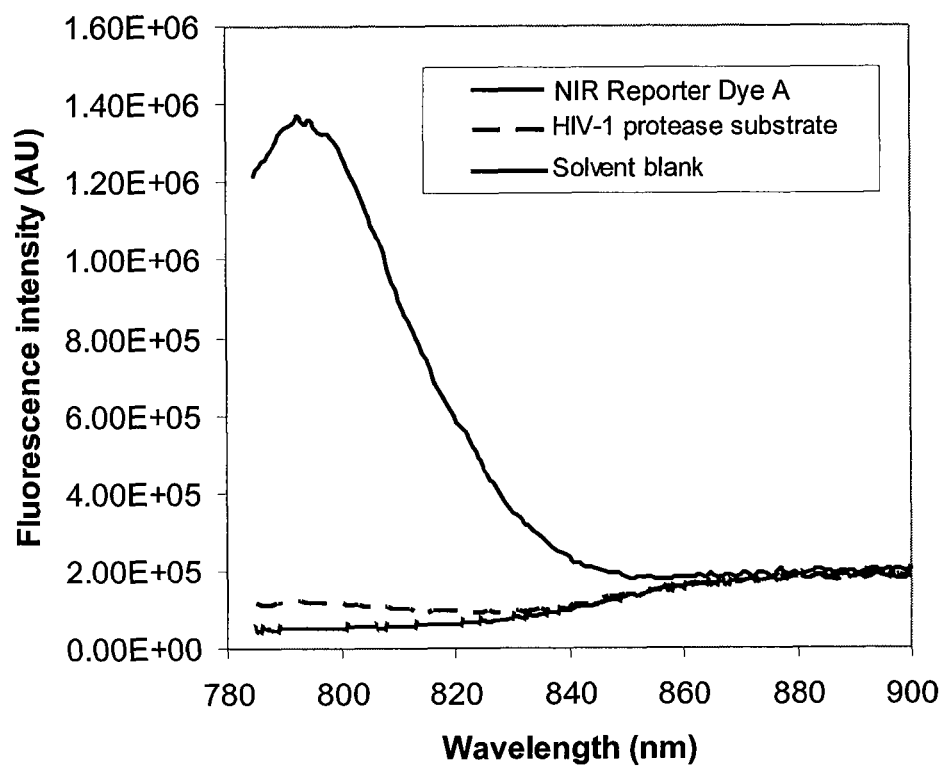
FIG. 17 illustrates the efficiency of a quencher group to quench the fluorescence of a NIR Reporter Dye A, when both are attached to a HIV-1 protease substrate (VSQNYPIV-QNK; SEQ ID NO:4).

The quenching efficiency of NIR Reporter Dye A on a HIV-1 protease substrate (VSQNYPIVQNK; SEQ ID NO:4) is shown in FIG. 17. The fluorescence spectra of 100 nM of a HIV-1 protease conjugated substrate (i.e., (NIR Reporter Dye A)-VSQNY*PIVQNK-(Compound 6)-OH; SEQ ID NO:1) in phosphate buffer (1× PBS) containing 10% DMSO, and 100 nM of un-conjugated donor dye (NIR Reporter Dye A) in phosphate buffer (1× PBS) containing 10% DMSO, and a 1× phosphate buffer blank were measured on the PTI Photo Technology International fluorescent master system (NJ). As shown in FIG. 17, the fluorescence intensity of the HIV-1 protease conjugated substrate is ~5% of that of the unconjugated donor dye after subtraction of the background fluorescence of the buffer blank, which indicates that the reporter group's fluorescence is approximately ~95% quenched in the HIV-1 protease conjugated substrate in phosphate buffer.

In another embodiment, the methods herein are useful for the detection of β-secretase (i.e., BACE-1) protease activity. In certain aspects, the methods are useful for detecting the cleavage of the peptide sequence, SEVNLDAEFRKRR-COOH (SEQ ID NO:12), by the β-secretase enzyme. β-secretase (BACE-1) has been identified as a key enzyme that mediates a critical step in the formation of β-amyloid ($A\beta_{40/42}$) by acting upon the β-amyloid precursor protein (β-APP) (Vassar, R. et. al. "β-Secretase cleavage of Alzheimer's Amyloid Precursor Protein by the Transmembrane Aspartic Protease BACE" Science, 286(22), 735-741, 1999). The progressive of brain accumulation of β-amyloid ($A\beta_{40/42}$) into amyloid plaques is responsible for the Alzhemimer's disease (AD).

Figure 18:
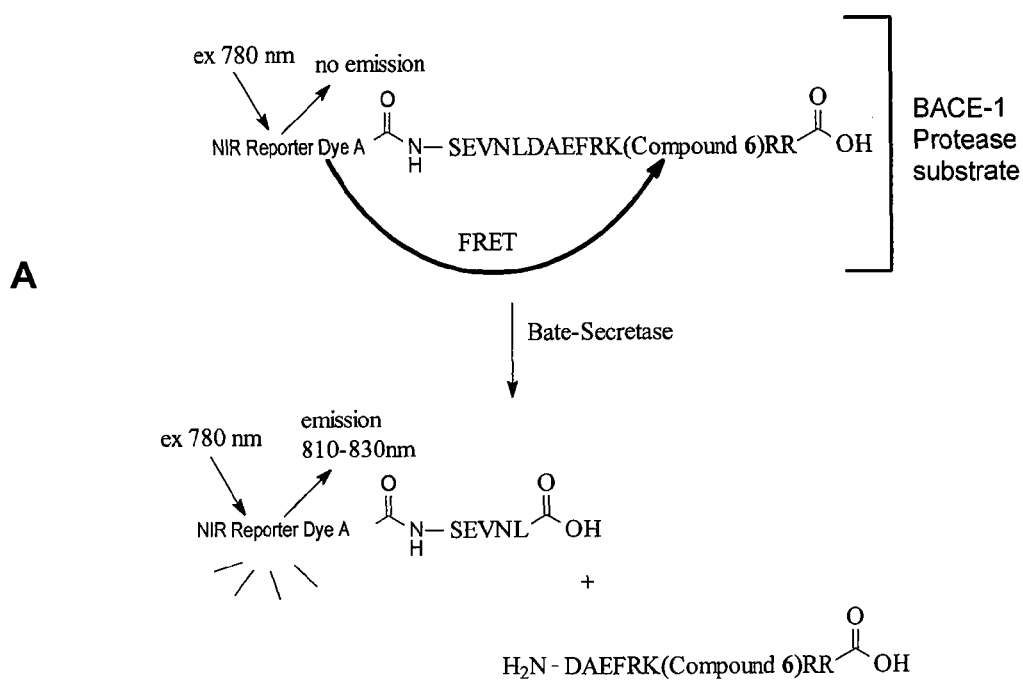
FIG. 18A shows a scheme that outlines a BACE-1 protease assay of the invention (SEQ ID NOS:5-7).
FIG. 18B illustrates the efficiency of a quencher group to quench the fluorescence of a reporter dye's fluorescence when both are conjugated to a BACE-1 protease substrate.
Figure 18:
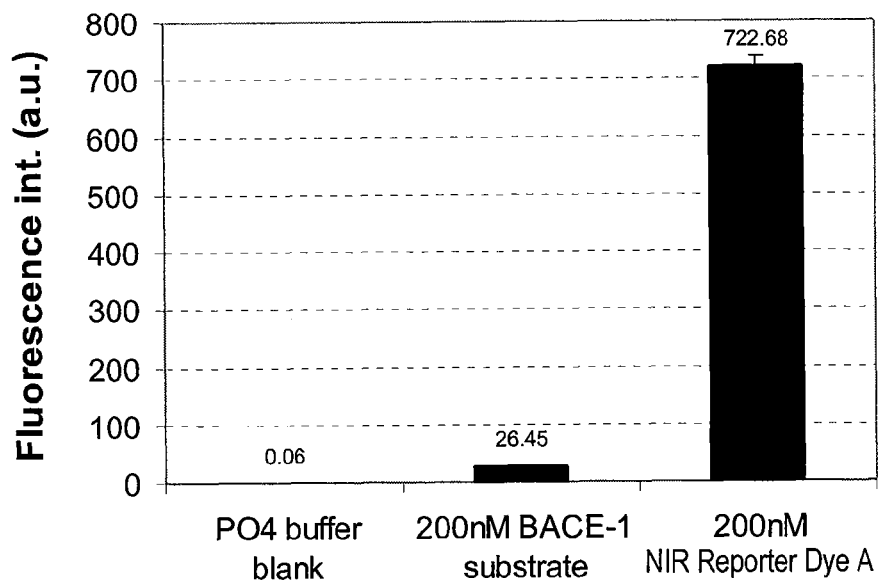

In one embodiment, the detection of β-secretase (BACE-1) activity is outlined in FIG. 18A. The peptide, SEVNLDAE-FRKRR-COOH (SEQ ID NO:12), is covalently conjugated to a NIR Reporter Dye A and the ENF quencher, compound 6, through the N-terminal amine group and the lysine amine group, respectively. In the presence of BACE-1, the reporter-quencher conjugated peptide substrate, (NIR Reporter Dye)-SEVNL*DAEFRK(Compound 6)RR-OH (SEQ ID NO:5), is cleaved (* denotes cleavage site) and thus, the reporter is separated from the quencher and its fluorescence is restored. The fluorescent signal generated linearly reflects the degree of substrate cleavage.

The quenching efficiency of the reporter dye's fluorescence on BACE-1 substrate is shown in FIG. 18B. The fluorescence intensities of 200 nM of dye-labeled BACE-1 substrate (i.e., (NIR Reporter Dye A)-SEVNLDAEFRK (Compound 6)RR-OH; SEQ ID NO:5) in 100 mM phosphate buffer (pH 7.8); and 200 nM of unconjugated NIR Reporter Dye A in 100 mM phosphate buffer (pH 7.8); and phosphate buffer blank were measured on Aerius® infrared imaging system. FIG. 18B shows that the fluorescence intensity of BACE-1 substrate is ~4% of that for an unconjugated donor dye, which indicates a ~96% quenching of the donor fluorescence in this buffer system.

Figure 3:
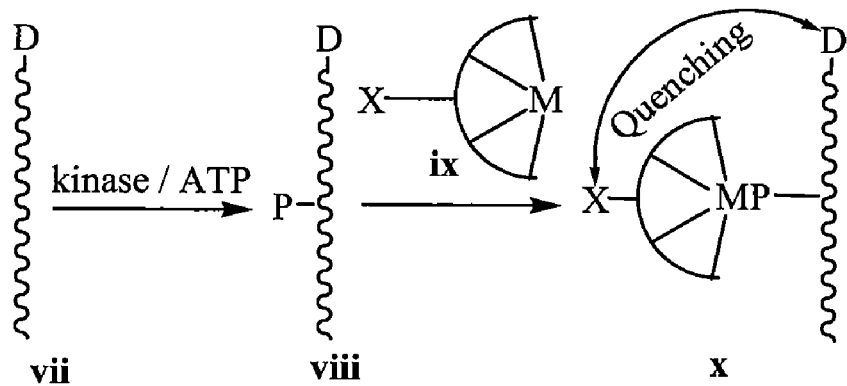
FIG. 3 shows a schematic illustrating a kinase assay of the present invention.

In another aspect, the methods of the present invention detect the activity of a kinase. As shown in FIG. 3, when the assay method is used to monitor the activity of a kinase, the assay may be configured as follows. A reporter dye conjugated enzyme substrate (vii) is phosphorylated in an incubation mixture that includes as constituents, the fluorescent reporter dye conjugated substrate, the protein kinase of interest (e.g., serine/threonine kinases or tyrosine kinases), and a source of high energy phosphate group such as ATP. The incubation mixture may include other additives such as enzyme cofactors (e.g., $Ca^{2+}$ and $Mg^{2+}$) for enhancing activity, activators for the enzyme (e.g., phosphatidyl-L-serine for conventional protein kinase C (PKC) isoforms and cyclic AMP or PKA). The mixture can be further supplemented with common enzyme stabilizing agents, such as a reducing agent (i.e., dithiothreitol) or a detergent (i.e., Triton X-100). In many assays, particularly for drug screening, putative agonists or antagonists of the protein kinase being studied may also be present.

A kinase mixture is incubated for a select period of time, to produce a reaction mixture that contains phosphorylated product (viii) and possibly remaining non-phosphorylated substrate. To the reaction mixture is added an essentially non-fluorescent quencher dye conjugated to an ion-complexing moiety (ix), which binds to the phosphate group on the phosphorylated product, to form a complex (x). In (x) the quencher dye is now in proximity to the reporter dye on the phosphorylated product, to result in the diminishing of the reporter dye's fluorescence. The progress of the reaction may be monitored by detecting, at a wavelength of about 650-900 nm, the decrease in fluorescence emission of the reaction mixture due to the quenching of the reporter dye. In one embodiment, the ion-complexing moiety (ix) in FIG. 3 is replaced with a phospho-specific antibody having a quencher group attached thereto. In certain aspects, the phospho-specific antibody, is preferably a p-Tyr-100 antibody, available from Cell Signaling Technology.

In yet another aspect, the methods are used to detect the activity of a phosphatase. In this embodiment, the conditions outlined above for the kinase enzyme activity can be employed taking into consideration the modifications that are required to evaluate a phosphatase enzyme (e.g., ATP can be omitted). In contrast to the observed decrease fluorescence observed for the kinase assay, an increase in fluorescence will be observed in the case of a phosphatase enzyme. The phosphatase assay will require the use of a phosphorylated substrate having a fluorescent reporter dye and an ion-complexing moiety attached thereto.

In yet another aspect, the present invention provides an assay method for detecting the activity of an enzyme by detecting the degradation of a protein substrate having a molecular weight of at least of about 5 kD, the method comprising:
a) providing a protein substrate having conjugated thereto a plurality of near-infrared reporter dyes, wherein the dye conjugated substrate is substantially non-fluorescent, wherein each reporter dye absorbs at a wavelength of about 650-900 nm;
b) incubating the protein substrate with the enzyme to generate a product; and
c) detecting the product by monitoring fluorescence at wavelength of between about 650-900 nm, to detect the activity of the enzyme.

In yet another aspect, the present invention provides an assay method for detecting the presence or absence of at least one protease by detecting the degradation of a protein substrate having a molecular weight of at least about 5 kD, the method comprising:
a) providing a protein substrate having conjugated thereto a plurality of near-infrared reporter dyes, wherein the dye conjugated substrate is substantially non-fluorescent, wherein each reporter dye absorbs at a wavelength of about 650-900 nm;
b) incubating the protein substrate in a biological assay medium; and
c) detecting the presence or absence of the protease by detecting the formation of a product by monitoring fluorescence at wavelength of between about 650-900 nm, to detect the presence of at least one protease.

Generally, the activity of the enzyme is detected by monitoring an increase in the fluorescence. These assay methods are particularly beneficial as a "general protease assay" to detect the presence of at least one or more types of proteases. Typically, the protein substrate has a molecular weight of between 19 and 70 kD, preferably between 19-25 kD. Within certain embodiments, the protein substrate is preferably casein or BSA. In other embodiments, the protein substrate is for example, a protein product such as gelatin. Within certain embodiments, the protein substrate is preferably casein. Additionally, in assay method B or C, the NIR reporter dye is preferably a dye having formula II above, wherein the variables, X, Y, Z and $R^{22a}$-$R^{28d}$ are as described above. Alternatively, the NIR dye is a cyanine dye. In one preferred embodiment, the cyanine dye is NIR Reporter Dye B which has the structure prior to attachment to the substrate:

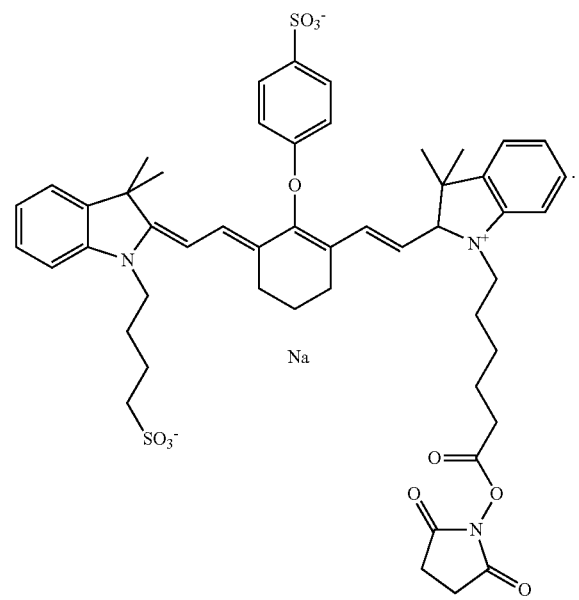

In one embodiment, the enzyme is a preferably a protease. The protease may be selected from the group consisting of cathepsin, chymotrypsin, elastase, papain, pepsin, protease XIV, protease K, thermolysin, trypsin, ADAM protease, matrix metalloprotease, bromolain, collagenase, kallikrein, plasmin, renin, streptokinase, subtilisin, thermolysin, thrombin and urokinase, or a combination thereof, and the like.

Figure 9:
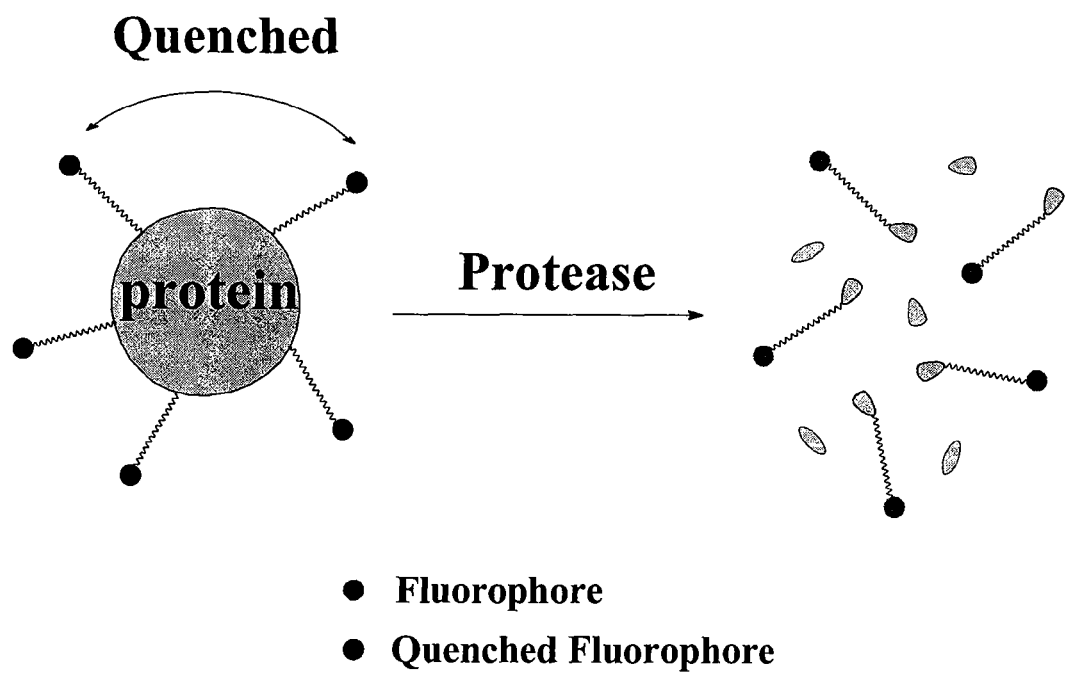
FIG. 9 shows a schematic of a fluorescence quenching based protease assay using the protein casein.
Figure 11:
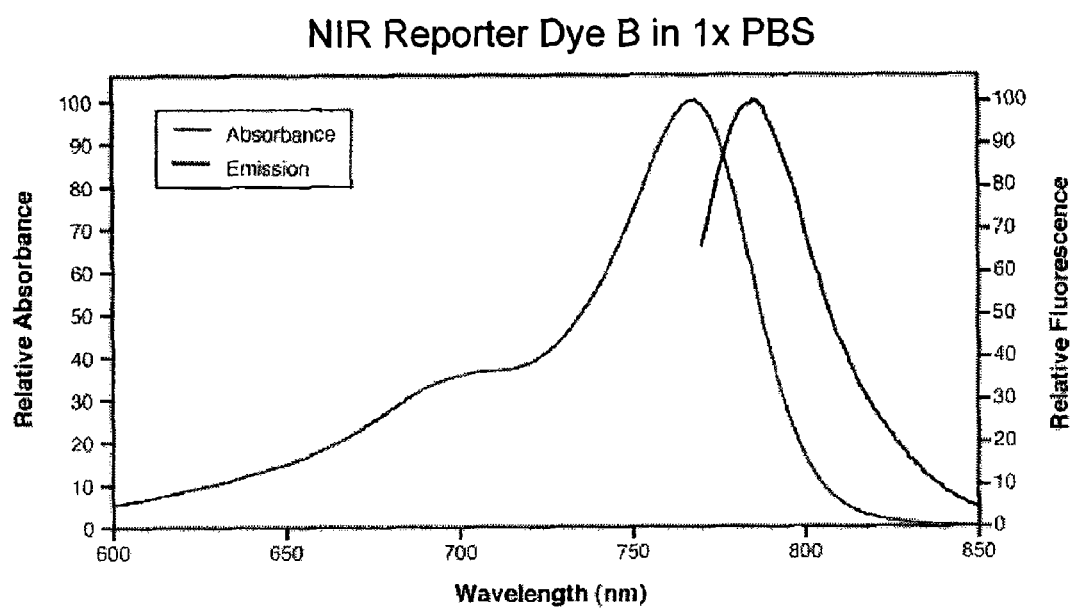
FIG. 11 shows the absorbance and emission spectra of NIR Reporter Dye B.

In certain aspects, an assay used to detect general protease (proteolytic) enzyme activity can also be configured as shown in FIG. 9. In this example, a protein substrate is highly conjugated with fluorescent dyes, and the resulting protein has very low fluorescence intensity (is substantially non-fluorescent) because the proximity of the dye molecules on a single protein substrate leads to quenching. However, in the presence of at least proteolytic enzyme, the dye-conjugated substrate is digested and fragmented into many small dye-conjugated peptides. This process separates the fluorescent dye molecules, and thus these fluorescent dyes are detectable upon excitation. As such, the protease activity can be measured with the fluorescence intensity change.

The following examples set forth certain embodiments of the invention, and are intended to be purely exemplary of the invention and not in any way to limit its scope.

V. EXAMPLES

Example 1

Preparation of Cyanine Dyes 5, 6 and 7:

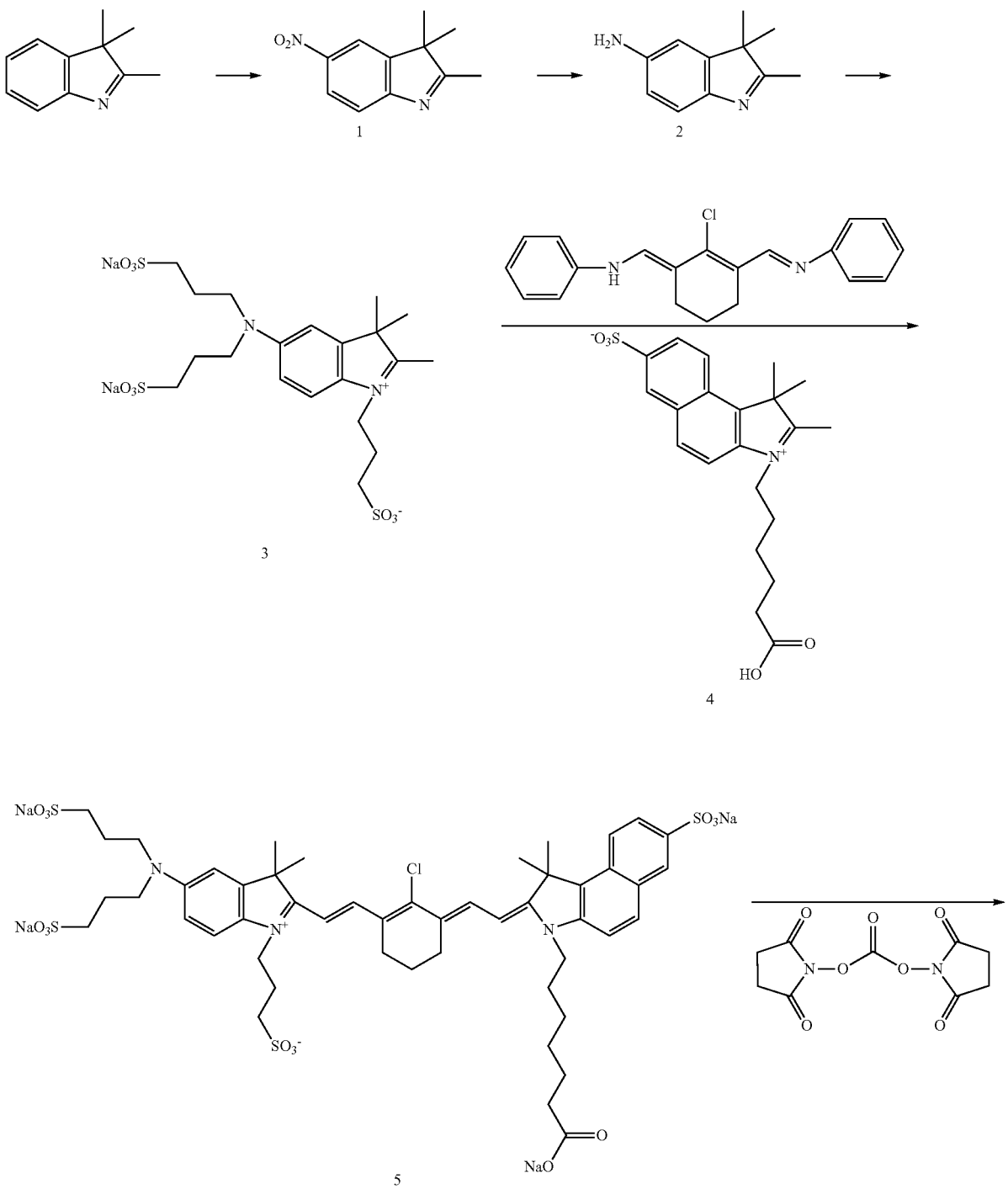

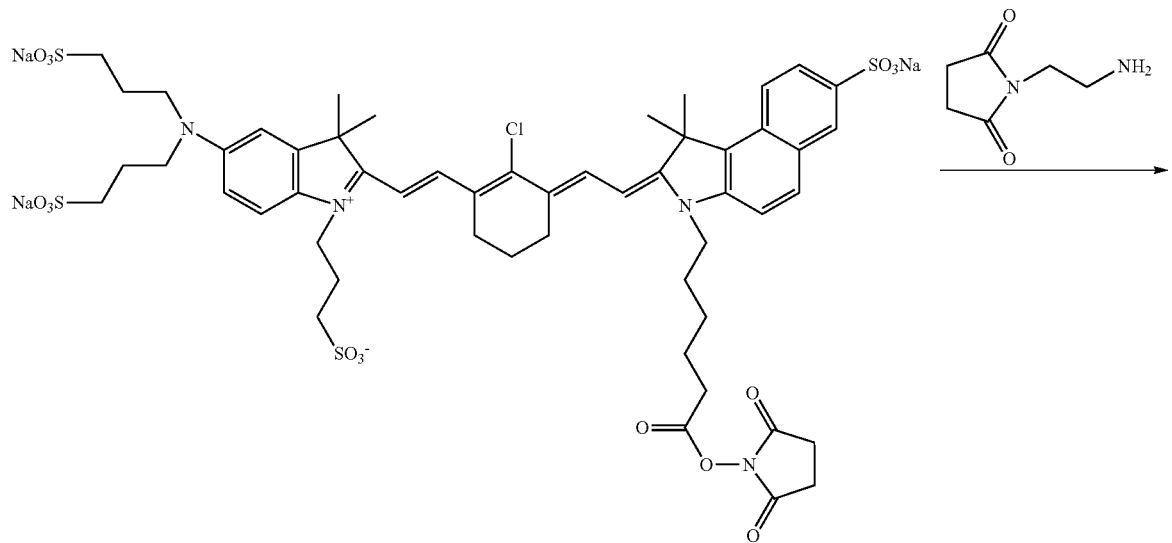

6

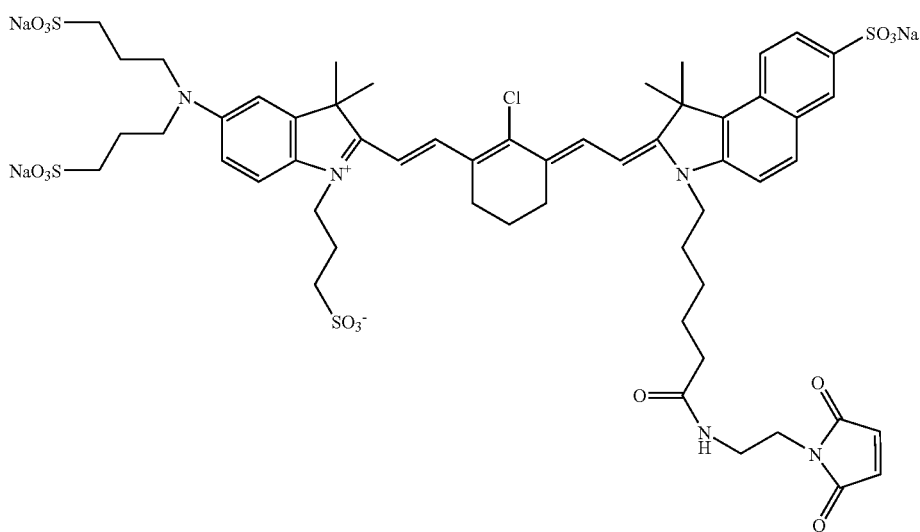

7

Preparation of 5-nitro-2,3,3-trimethylindole (1). 5-nitro-2,3,3-trimethylindole (1) was synthesized according to a modified literature procedure (see, Noland, W. E., et al., *J. Org. Chem.* 3457-3469, 1965). To a solution of 2,3,3-trimethylindole (10.6 g) in concentrated sulfuric acid cooled to 0° C. using an ice/brine bath was added dropwise fuming nitric acid (5.6 mL). The resultant solution was stirred at 0° C. for 1.5 hours; then poured into crushed ice; filtered; and washed with water. The combined filtrate was neutralized to a pH greater than 7. The product precipitated from the neutralized solution and was collected by filtration, washed with water, and dried to provide the desired product 1 (10.1 g, 74% yield): ESI-MS, calculated $[M+H]^+$ 205.1, found 205.0.

Preparation of 5-amino-2,3,3-trimethylindole (2). To the solution of 5-nitro-2,3,3-trimethylindole (1) (10 g) in EtOH (50 mL), hydrazine (35% in water, 6.72 g) was slowly added. The mixture was allowed to stir at room temperature for 10 min followed by the addition of palladium on carbon (Pd/C) (20% Pd/C, 1.30 g). The resultant suspension was heated at 70° C. for 2 hours, filtered, and concentrated to provide the desired product 2 (8.52 g, 100% yield): ESI-MS, Calculated $[M+H]^+$ 175.1, Found 175.1.

Preparation of 1-(γ-Sulfonatopropyl)-5-(N,N-di-(γ-sulfonatopropyl)amino)-2,3,3-trimethyl-indolium tri sodium salt (3). 5-amino-2,3,3-trimethylindole (2) (100 mg, 0.57 mmol), $K_2CO_3$ (156 mg, 1.14 mmol) and 1.3-propanesultone (315 mg, 2.58 mmol) were combined in 50 ml of methoxyethanol and heated at 100° C. for 4 hours. The reaction mixture was cooled and crude product 3 was precipitated out with the addition of ethyl ether. The crude product 3 is collected, dried and used without further purification (452 mg): ESI-MS, Calculated $[M+H]^+$ 541.1, Found 541.1.

Preparation of compound 5. Compound 3 (112 mg), Compound 4 (72 mg), and N-[(3-(anilinomethylene)-2-chloro-1- cyclohexen-1-yl)methylene]aniline monohydrochloride (61 mg) were combined in methoxyethanol (30 ml) and triethylamine (94 μL) and heated at 70° C. overnight. The reaction mixture was concentrated by rotary evaporation, purified by reversed phase chromatography, and ion-exchange column (sodium form ion-exchange resin), and concentrated to provide the desired product 5 (24 mg): UV-Vis, $\lambda_{max}$ (MeOH) 793 nm; ESI-MS, Calculated $[M-4Na^++5H]^+$ 1080.3, Found 1080.3.

Preparation of compound 6. Compound 5 (26 mg) and N,N'-disuccinimidyl carbonate (57 mg) were dissolved in N,N-dimethylformide (anhydrous, amine-free) and dimethylsulfoxide (anhydrous). The resultant solution was stirred at room temperature for 2 hours under argon atmosphere. The product precipitated upon dilution of the reaction solution with ethyl ether. The precipitated product was isolated by centrifuge and the product 6 was washed with ethyl ether and dried to provide the desired product 6 (27 mg, 99%).

Preparation of compound 7. Compound 7 is synthesized by reacting compound 6 with 1-(2-Amino-ethyl)-pyrrole-2,5-dione.

Example 2

Preparation of Cyanine Dyes 9 and 10:

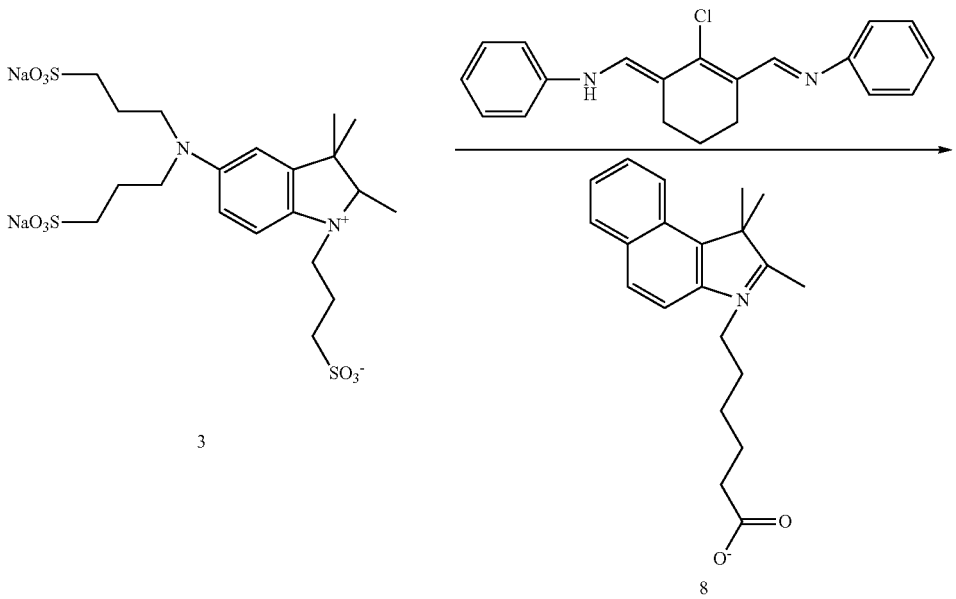

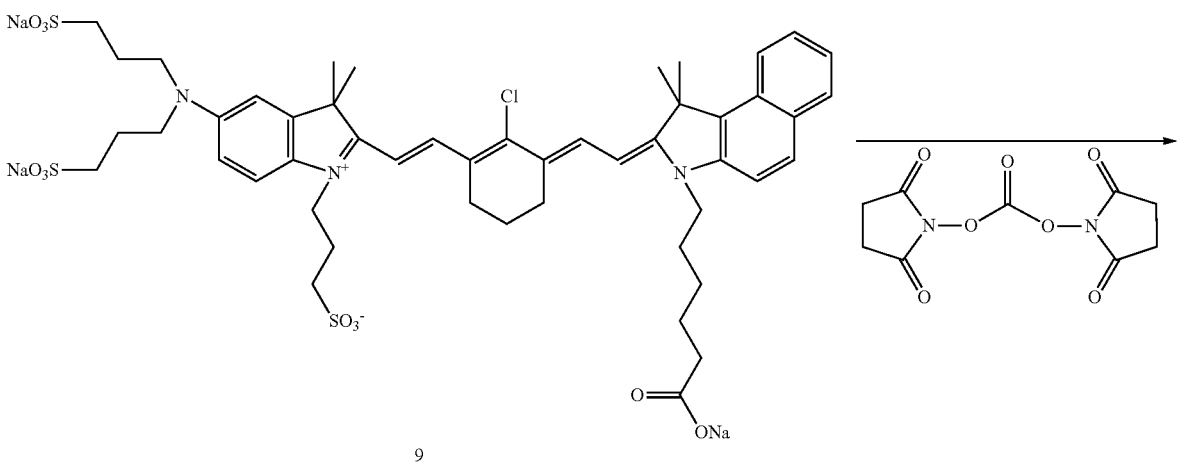

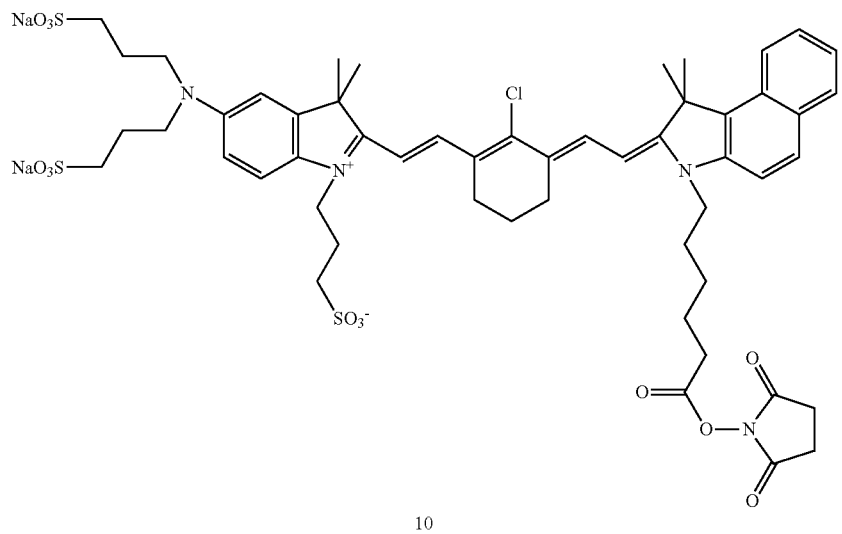

Preparation of compound 9. Compound 3 (810 mg), N-(ε-carboxypentenyl)-1,1,2-trimethylbenzo[e]indolium 8 (487 mg) and N-[(3-(anilinomethylene)-2-chloro-1-cyclohexen-1-yl)methylene]aniline monohydrochloride (539 mg) were dissolved in methoxyethanol (10 mL) and triethylamine (1.5 mL) and stirred at 70° C. under nitrogen for 16 hours. The reaction mixture was concentrated by rotary evaporation, purified by reverse phase-high pressure liquid chromatography (RP-HPLC) and further purified by preparative HPLC. The product was ion-exchanged (sodium form ion-exchange resin) and dried to provide the desired product 9 (18 mg): UV-Vis, $\lambda_{max}$ (MeOH) 793 nm; ESI-MS (m/z), calculated [M-2Na$^+$+3H]$^+$ 1000.3, found 1000.6.

Preparation of compound 10. Compound 9 and N,N'-disuccinimidyl carbonate is dissolved in N,N-dimethylformamide (anhydrous, amine-free) and dimethylsulfoxide (anhydrous) and is stirred at room temperature for 2 hours under argon atmosphere. The product precipitates upon dilution of the reaction solution with ethyl ether. The precipitated product is isolated by centrifuge. The crude product is washed with ethyl ether and dried to provide the desired product 10.

Example 3

Preparation of Cyanine Dyes 12 and 13:

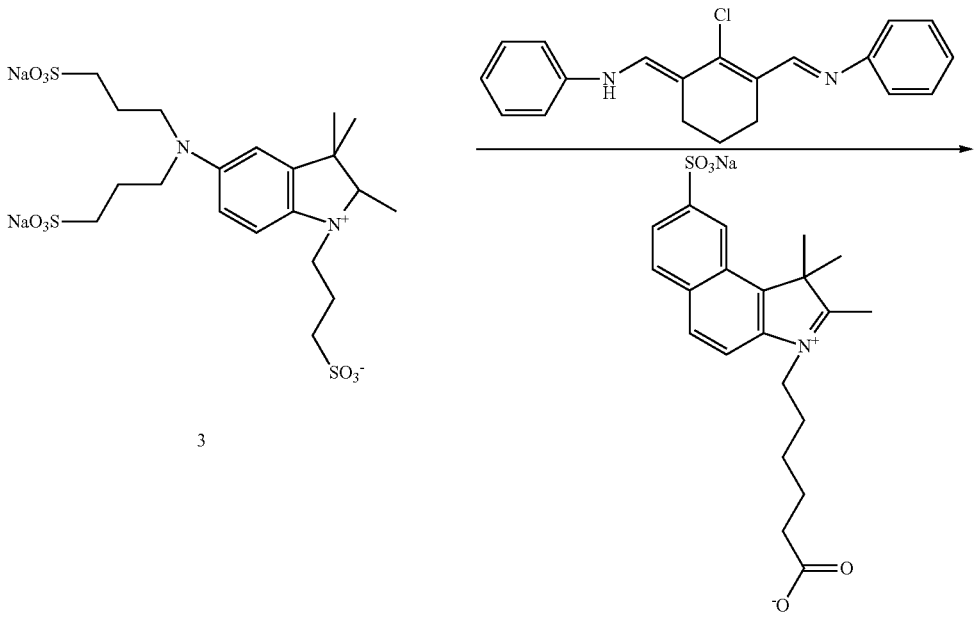

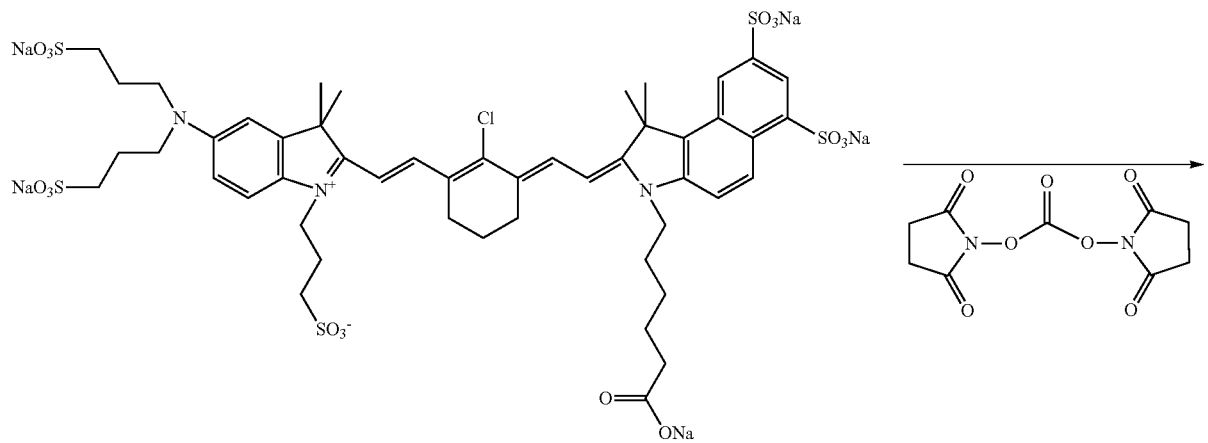

12

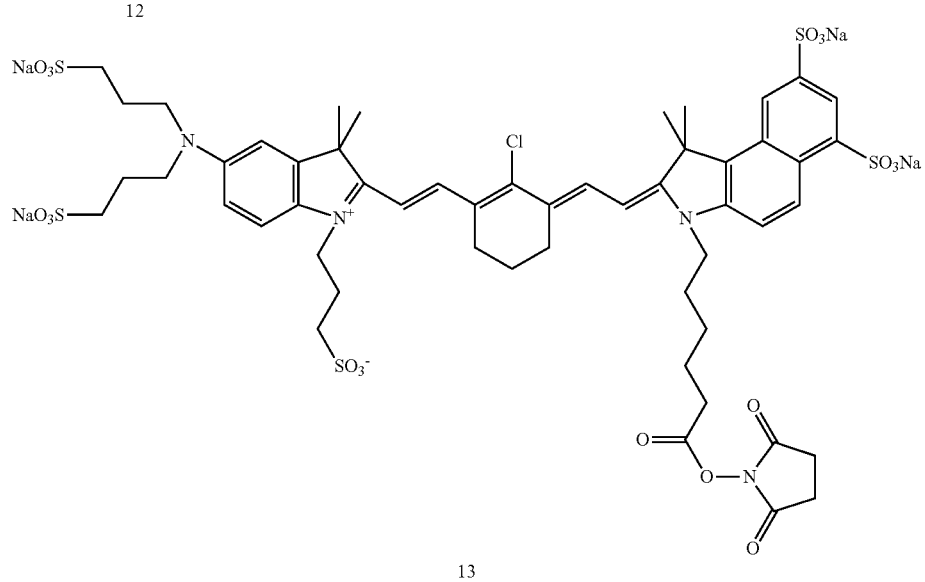

13

Preparation of compound 12. Compound 3 (29 mg), N-(ε-carboxypentenyl)-1,1,2-trimethyl-6,8-di-(sulfonato)-benzo[e]indolium-bis sodium salt (11) (28 mg) and N-[(3-(anilinomethylene)-2-chloro-1-cyclohexen-1-yl)methylene]aniline monohydrochloride (19 mg), was dissolved in methoxyethanol (1 mL) and triethylamine (50 μL) and stirred at 70° C. under nitrogen atmosphere for 16 hours. The product is collected by ethyl ether precipitation and purified on RP-HPLC and concentrated to provide the desired product 12 (2 mg): UV-Vis, $\lambda_{max}$ (MeOH) 790 nm; ESI-MS (m/z) calculated [M-5Na$^+$+6H$^+$]$^+$ 1160.2, found 1160.3.

Preparation of compound 13. Compound 12 and N,N'-disuccinimidyl carbonate are diluted in N,N-dimethylformide (anhydrous, amine-free) and dimethylsulfoxide (anhydrous) and the resultant solution is stirred at room temperature under argon atmosphere for 2 hours. The precipitated product is isolated by centrifuge and the product 13 is washed with ethyl ether and dried to provide the desired product.

Example 4A

Preparation of Cyanine Dye 19A, 19B and 20:

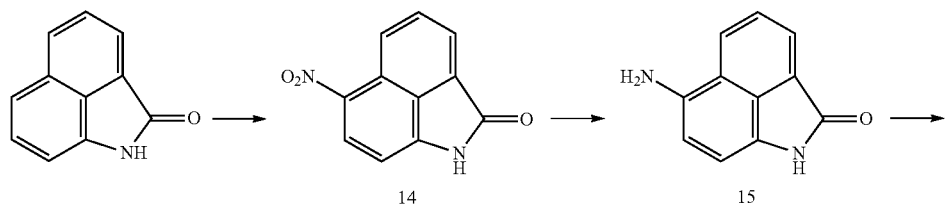

-continued
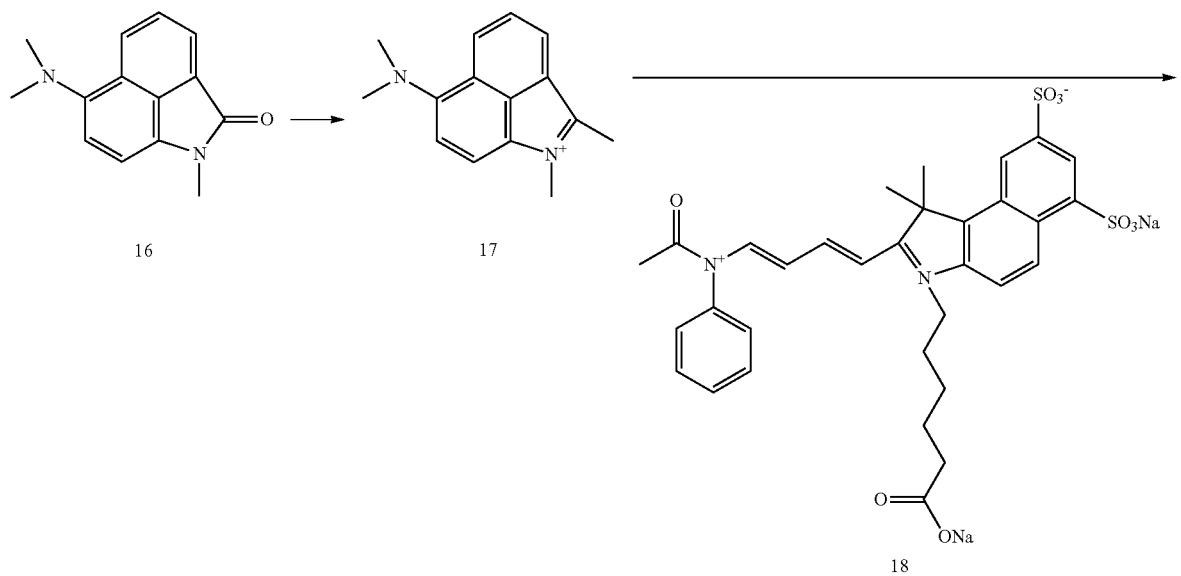
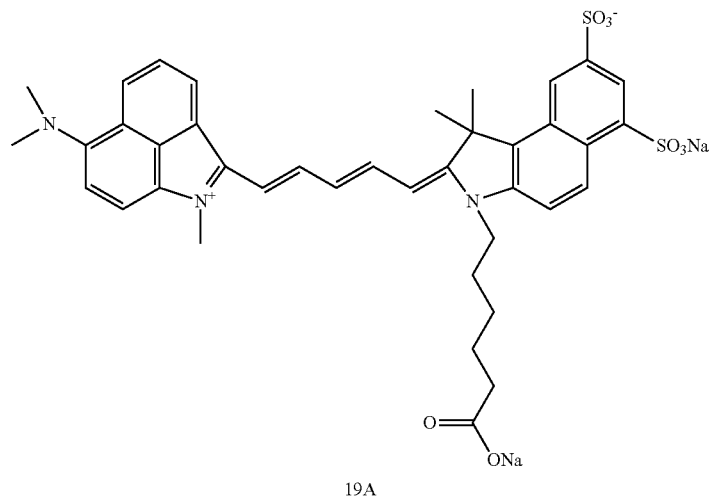
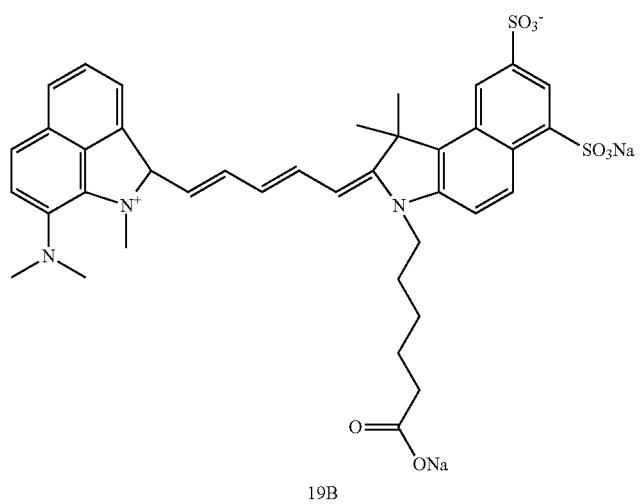

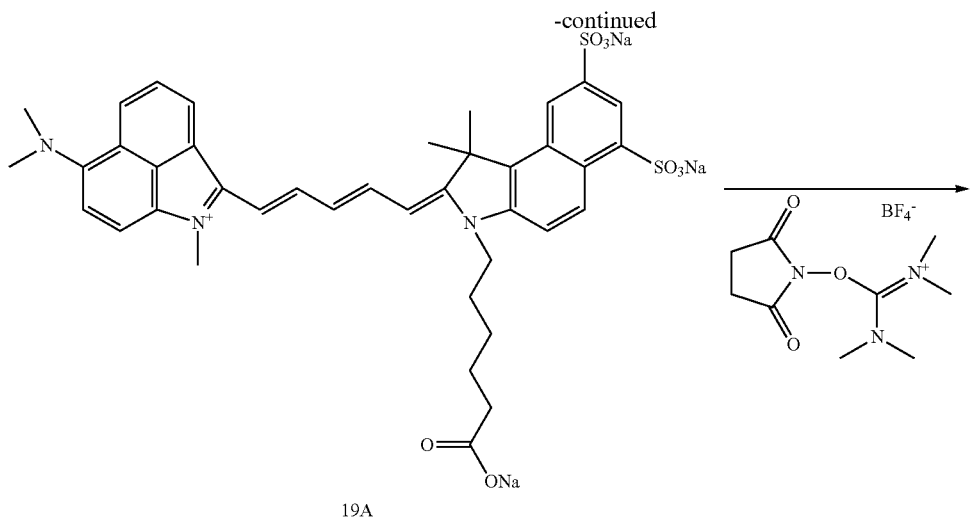

19A

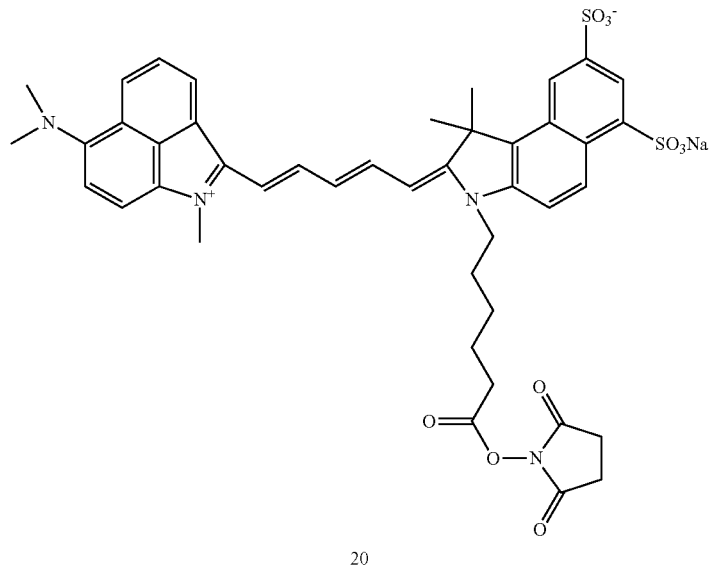

20

Preparation of 6-Nitro-1-H-benzo[cd]indol-2-one (14). Fuming nitric acid (1 mL) is added dropwise to a solution of benz(c,d)indol-2(1H)-one (0.92 g, 5.46 mmol) in concentrated sulfuric acid (2.3 mL) while the solution is maintained at 0° C. by ice/brine bath. The resultant solution was stirred at 50° C. for 0.5 hour. The reaction mixture was poured into crush ice and the crude product precipitated out of solution. The crude product was isolated by filtration and washed with water and dried to provide the desired product 14 (1.10 g, 92% yield): UV-Vis, $\lambda_{max}$ (MeOH), 248, 299, 393 nm; ESI-MS, Calculated [M+H]$^+$ 215.2, Found 215.2.

Preparation of 6-amino-1H-benzo[cd]indol-2-one (15). Compound 15 was prepared as a yellow solid according to the similar procedure outlined in Example 1 for compound 2.

Preparation of 6-(N-N-dimethyl)amino-1methyl-benzo[cd]indol-2-one (16). Compound 14 (10 g, 54 mmol), iodomethane (23 g, 162 mmol), sodium hydroxide (2.16 g, 54 mmol) and potassium carbonate (14 g, 108 mmol) were diluted in ethoxyethanol (100 ml) and stirred at room temperature for 2 hours. The reaction mixture was then heated to 70° C. overnight. The reaction mixture was filtered and concentrated to provide the desired product 16 (11.52 g): UV-Vis, $\lambda_{max}$ (MeOH) 284, 405 nm; ESI-MS Calculated [M+H]$^+$ 227.2, Found 227.2.

Preparation of 6-(N,N-dimethyl)amino-1,2-dimethyl-benzo[cd]indolium (17). To the solution of Compound 16 (1.2 g, 5.6 mmol) in tetrahydrofuran (anhydrous, 40 mL) was added CH$_3$MgBr (3M in THF, 7 ml, 22.4 mol). The resultant mixture was stirred at 60° C. for 30 minutes, then poured into ice-water, concentrated by rotary evaporation, and purified by reverse phase chromatography to provide the desired product 17 (1.1 g, yield 87%): UV-Vis, $\lambda_{max}$ (MeOH) 568 nm; ESI-MS Calculated [M+H]$^+$ 226.1, Found 226.1.

Preparation of Compounds 19A and 19B. 6-[2-(4-N-acetyl-N-phenylimino-but-2-enylidene)-1,1-dimethyl-7,9-disulfonato-1,2-dihydrobenzo[e]indol-3-yl]-hexanoic acid (18) was synthesized similar to the procedure outlined in Bioconjugate Chem. 1996, 7, 356-362 and Bioconjugate Chem. 1993, 4, 105-111. Compound 18 and compound 17 (45 mg, 0.14 mmol) were dissolved in pyridine (anhydrous, 20 ml) and the reaction mixture was allowed to stir at room temperature overnight. The crude product was precipitated by the addition of ethyl ether (60 mL). The precipitate was collected and separated by preparative HPLC. Two isomer dyes (compound 19A and 19B) were obtained. Evidently, nitration reaction to produce compound 14 produced an additional nitrated product, i.e, 8-nitro-1H-benzo[cd]indol-2-one, which reacted to produce 19B: Compound 19A, UV-Vis, $\lambda_{max}$ (MeOH): 811 nm; Compound 19B, UV-Vis, $\lambda_{max}$ (MeOH) 803 nm; ESI-MS, Calculated [M+H]$^+$ 743.2, Found 744.3.

Preparation of Compound 20. Compound 20 is synthesized by reacting compound 19A with O-(N-succinimidyl)-N,N, N',N'-tetramethyluronium tetrafluoroborate in pyridine (anhydrous, 6 mL) and DMF (anhydrous, 10 mL). The reaction mixture is stirred at room temperature for 3 hours. The product is precipitated out of solution by diluting the reaction mixture with ethyl ether, and centrifuged to provide the crude product. The crude product is washed with acetonitrile, and dried under vacuum to provide the desired product 20.

Example 4B

Preparation of Cyanine Dyes 21, 22.

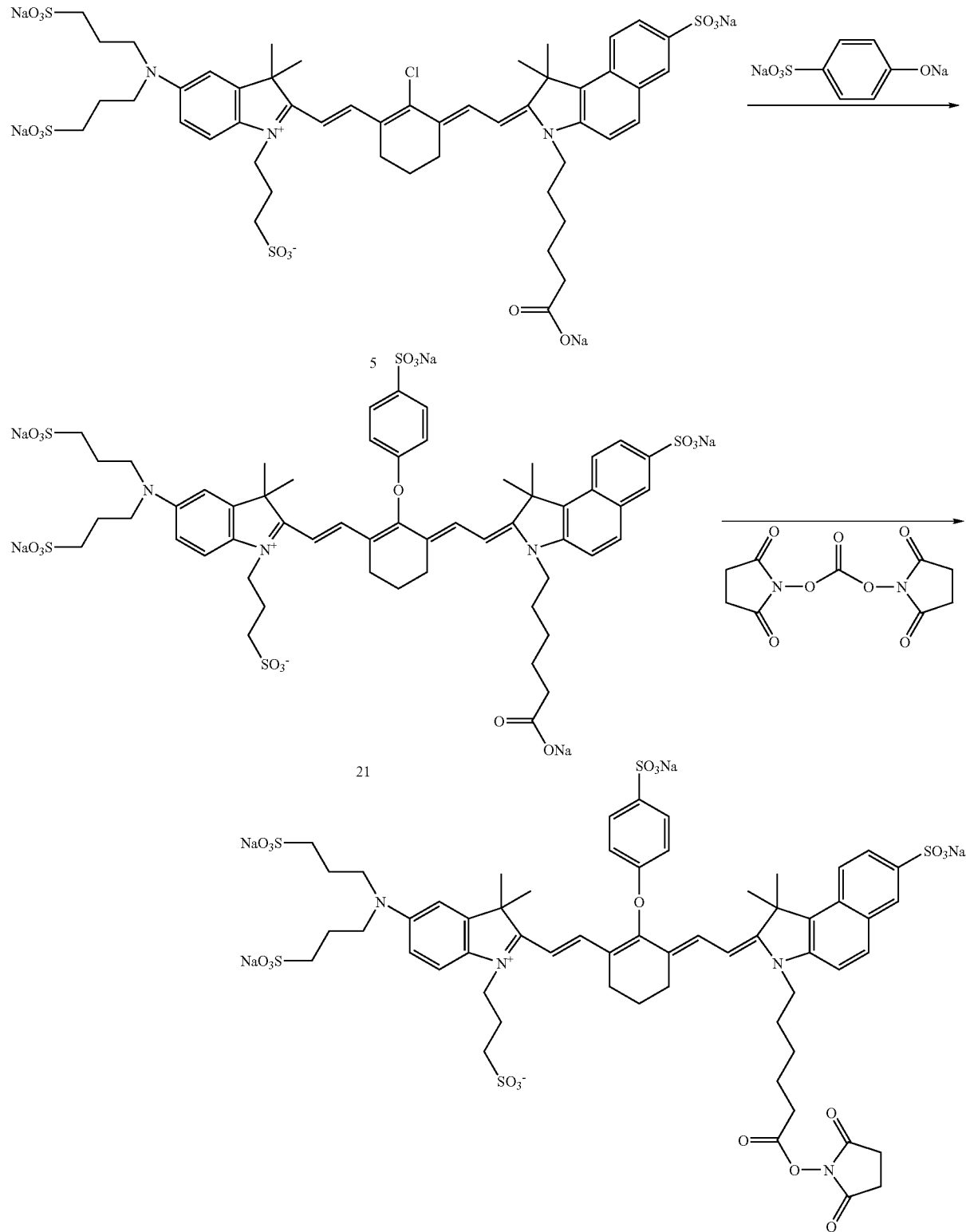

Preparation of Compound 21. Compound 5 (74 mg), 4-sulfonatophenoxide disodium salt (300 mg) in water was heated at 60° C. overnight. The reaction mixture was concentrated by rotary evaporation, and purified by reversed phase chromatography and ion-exchange column (sodium form ion-exchange resin), and concentrated to provide the product 21: UV-Vis, $\lambda_{max}$ (MeOH) 780 nm; ESI-MS, Calculated $[M-5Na^++6H]^+$ 1218.3, Found 1218.2.

Preparation of Compound 22. Compound 21 and N,N'-disuccinimidyl carbonate is dissolved in N,N-dimethylformamide (anhydrous, amine-free) and dimethylsulfoxide (anhydrous) and is stirred at room temperature for 2 hours under argon atmosphere. The product precipitates upon dilution of the reaction solution with ethyl ether. The precipitated product is isolated by centrifuge. The crude product is washed with ethyl ether and dried to provide the desired product 22.

Example 5A

Synthesis of a Labeled HIV Protease Substrate (Structure III):

The 11-mer peptide VSQNY*PIVQNK (SEQ ID NO:4) (* indicates the cleavage site) was synthesized by Bio-peptide LLC in the form that its N-terminal is deprotected and the peptide is still attached on the resin with all other residues being protected. NIR Reporter Dye A NHS-ester (LI-COR® BioSciences) is covalently conjugated to the N-terminal of the peptide by incubating on a rotor at room temperature for overnight in dimethylformamide (DMF) in the presence of triethylamine. The resulting NIR Reporter Dye A conjugated peptide tethered resin was washed with DMF then water and dried. The resin was then treated with a solution containing phenol (0.75 g), thioanisole (0.5 mL), water (0.5 mL) and trifluoroacetic acid (TFA) to remove all the protecting groups on the side chains of the peptide and to cleave the peptide from the resin at the same time. The product is purified by filtration and ethyl ether precipitation. Further washing by ethyl ether and drying under vacuum provided the desired product, (NIR Reporter Dye A)-VSQNY*PIVQNK (SEQ ID NO:13) (* indicates the cleavage site). ESI-MS: calculated $[M-3Na^++5H]^{2+}$ 1137.4, found 1137.1.

(NIR Reporter Dye A)-VSQNY*PIVQNK (SEQ ID NO:13) was then reacted with compound 6 NHS-ester in phosphate buffer saline (pH~7) at room temperature for 2 hours 30 minutes. The reporter-quencher-labeled peptide product was purified by reverse-phase HPLC. The product was ion-exchanged (sodium form ion-exchange resin) and dried to provide the desired product (NIR Reporter Dye A)-VSQNY*PIVQNK-(Compound 6) (SEQ ID NO:1) (* indicates the cleavage site). ESI-MS: calculated $[M-Na^++4H]^{3+}$ 1149.02, found 1149.06.

Example 5B

Synthesis of a Labeled β-Secretase (BACE-1) Protease Substrate (Structure IV).

Figure 19:
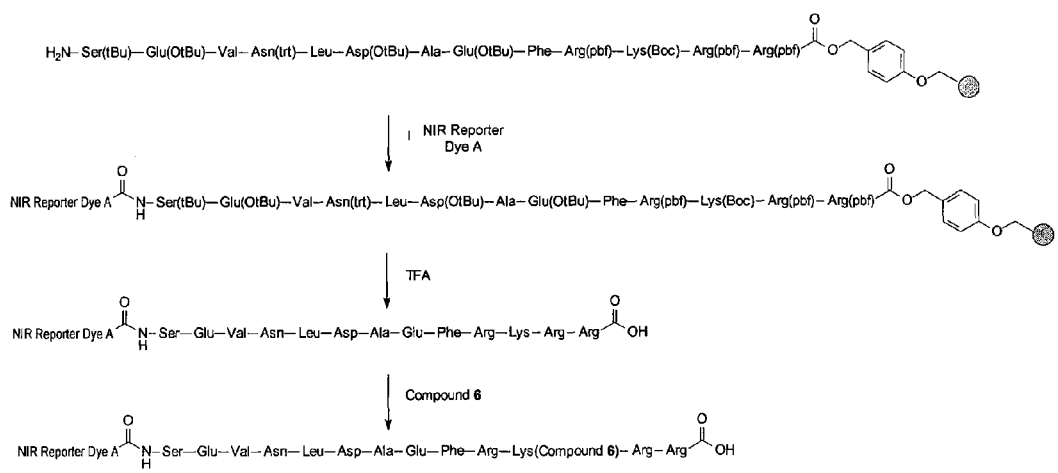
FIGS. 19A-B pertains to the synthesis and purity analysis of a BACE-1 protease substrate.
Figure 19:
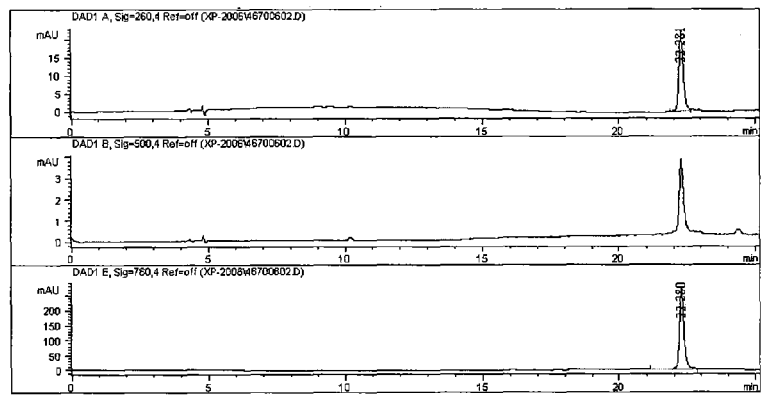

The synthesis of BACE-1 protease substrate is summarized in FIG. 19A. A peptide sequence for a BACE-1 protease substrate is: SEVNL*DAEFRKRR-OH (SEQ ID NO:12) (*indicates the cleavage site). The peptide was synthesized by Bio-peptide LLC (San Diego, Calif., USA) with its N-terminal deprotected and the peptide is still attached on the resin with all other residues being protected (i.e., the BACE-1 peptide sequence is: H₂N{Ser(tBu)} {Glu(OtBu)} {Val} {Asn(Trt)} {Leu} {Asp(OtBu)} {Ala} {Glu(OtBu)} {Phe} {Arg(Pbf)} {Lys(Boc)} {Arg(Pbf)} {Arg(Pbf)} (TGA resin) (SEQ ID NO:8). NIR Reporter Dye A-NHS-ester dye (LI-COR® BioSciences) was covalently conjugated to the N-terminal of the resin-tethered peptide by incubating on a rotor at room temperature for overnight in dimethylformamide (DMF) in the presence of diisopropylethylamine (DIPEA). The resultant NIR Reporter Dye A dye-conjugated peptide was washed with dimethylformamide (DMF) followed by methanol. The resultant green-colored resin was then dried in vacuum oven at room temperature for 1 hour. Global deprotection of the peptide side chains, and cleavage of the peptide from the resin was accomplished by stirring the dye-conjugated peptide in a solution containing 95% TFA, 2.5% H₂O and 2.5% TIS. The deprotected peptide product was initially purified by filtration, followed by ethyl ether precipitation, and washing. The precipitated product was dried under vacuum at room temperature for 1 hour. Final purification was performed on prep HPLC using reverse-phase C18 column to provide the desired pure donor dye labeled peptide, (NIR Reporter Dye A)-SEVNLDAEFRKRR-OH (SEQ ID NO:10).

(NIR Reporter Dye A)-SEVNLDAEFRKRR-OH (SEQ ID NO:10) was then combined with Compound 6 NHS-ester in 0.8 M phosphate buffer (pH 7.8) at room temperature and stirred for 3 hours to provide the Compound 6 conjugated product. The resultant NIR Reporter Dye A-Compound 6-labeled peptide was purified by reverse-phase HPLC to provide the desired product, i.e., NIR Reporter Dye A-SEVNLDAEFRK(Compound 6)RR-OH (SEQ ID NO:5) (Structure IV). HPLC analysis of the product is shown in FIG. 19B, which confirms the desired purity of the compound.

Example 6

HIV-1 Protease Assay Configuration:

Recombinant HIV-1 protease (in 10 mM sodium phosphate pH 6.5, 1 mM EDTA, 10% glycerol, 0.05% BME, 50-100 mM NaCl) was purchase from BACHEM Biosciences (King of Prussia, PA, U.S.A.). The protease is initially thawed on ice, aliquoted into working portions and immediately frozen to −80° C. A working portion of the HIV-1 protease is removed from the −80° C. and thawed on ice right before use.

The HIV-1 protease assay buffer consists of 0.1 M sodium acetate, 1.0 M sodium chloride, 1.0 mM ethylenediaminetetraacetic acid (EDTA), 1 mg/mL bovine serum albumin (BSA) and the pH is adjusted to 4.7. The assay buffer also contains 10% DMSO unless otherwise specified. The stop buffer is a 0.8 M sodium phosphate buffer (pH 7.8). The inhibitor for HIV-1 protease, acetyl-pepstatin, is purchased from Sigma. The 96-well clear and flat bottom, black-wall microtiter plates are purchased from BD Biosciences. The Aerius® Automated Infrared Imaging System (LI-COR® Biosciences) is a two-color multiplexing detection system and is useful for reading microplates.

Example 7

Figure 4:
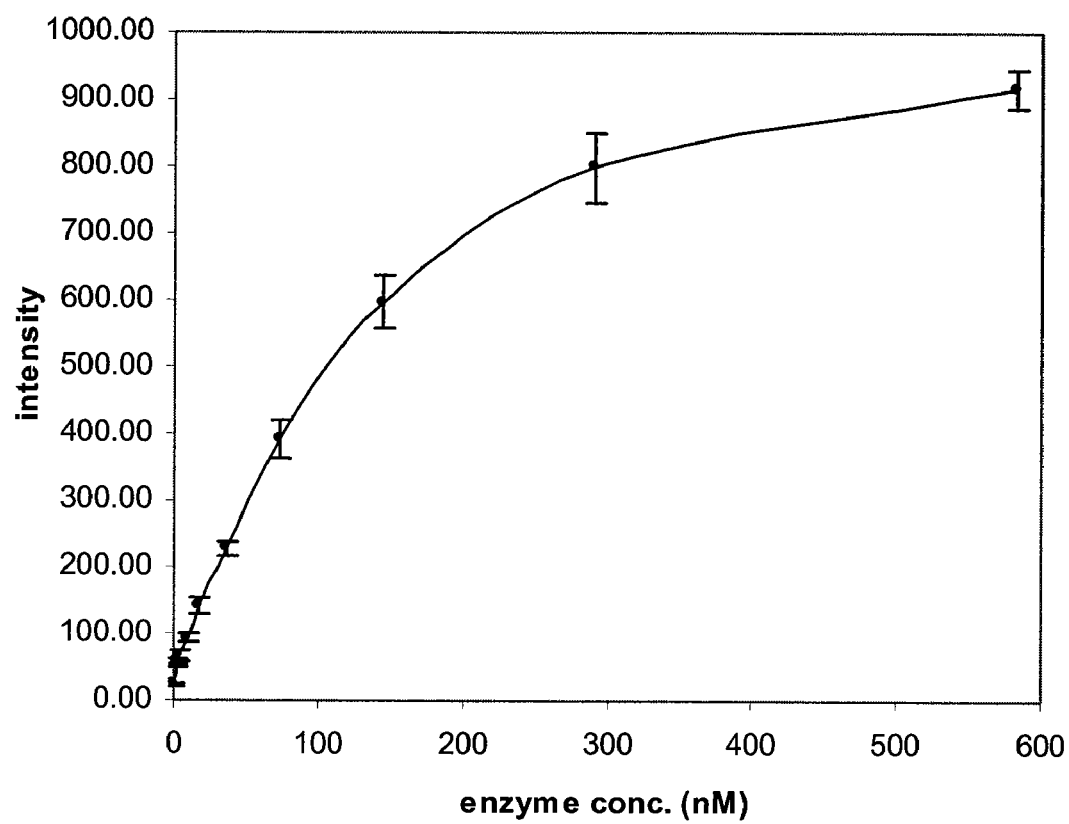
FIG. 4 shows the results of a protease activity assay of the present invention.

HIV-1 Protease Assay Activity:

In the HIV-1 protease activity assay, the substrate as prepared in Example 5A (250 nM) was incubated with enzyme in various concentrations (from 0 nM to 580 nM) at 37° C. for 1 hour. Then, the enzymatic reaction was stopped and the assay solution was diluted by 0.8 M sodium phosphate stop buffer (pH 7.8). The plate was then scanned on the Aerius® System (LI-COR® Biosciences). The result is shown in FIG. 4.

The HIV-1 protease activity demonstrates a very large dynamic window in this assay. A 35-fold intensity increase is achieved after proteolytic cleavage of the peptide substrate by monitoring the fluorescence change at 810 to 830 nm range (with 780 nm excitation). Previously reported near-infrared protease assays based on reporter/dye pair conjugated on peptide substrate only give a 10-fold increase in fluorescence signal after proteolytic cleavage for the Cy5 reporter-Cy7Q quencher pair by monitoring 650 nm fluorescence (see, EP 1,086,179) and a 7-fold increase in fluorescence signal after proteolytic cleavage for the Cy5.5 reporter-NIRQ820 quencher pair by monitoring 700 nm fluorescence (see, Pham, W., et al., *Bioconjugate Chem.*, 2004, 15, 1403-1407). Compared to the previously reported near-infrared protease assays, this new assay has the advantages of larger dynamic window and longer detect wavelength. A longer detect wavelength is beneficial in terms of minimizing background fluorescence interference.

Example 8

HIV-1 Protease Inhibition Assay:

The inhibition assay for determining the $IC_{50}$ value of a known HIV-1 protease inhibitor like Pepstatin A is used to validate the accuracy of this new HIV-1 protease assay. The inhibition assay to generate $IC_{50}$ value of Pepstatin A is performed in triplicate in a 96-well plate contains 20 nM enzyme, 1 µM substrate, and a serially diluted inhibitor solutions ranging from 9 µM to 0 nM concentration. The substrate concentration in this inhibition assay is at 1 µM which is ~100-fold below the reported $K_m$ (103 µM). The $IC_{50}$ value measured under this substrate concentration is expected to be the same as the $K_i$ since the substrate concentration is much less than the $K_m$ and Pepstatin A is a competitive inhibitor that has been determined in the literature. The inhibitor was mixed with the HIV-1 protease shortly before the addition of protease substrate. The plate was then incubated in a humidity controlled incubator for 2 hours. After completion, the assay solutions were stopped by 0.8 M sodium phosphate stop buffer (pH 7.8) and then scanned on the Aerius® Automated Infrared Imaging System (LI-COR® Biosciences).

Figure 5:
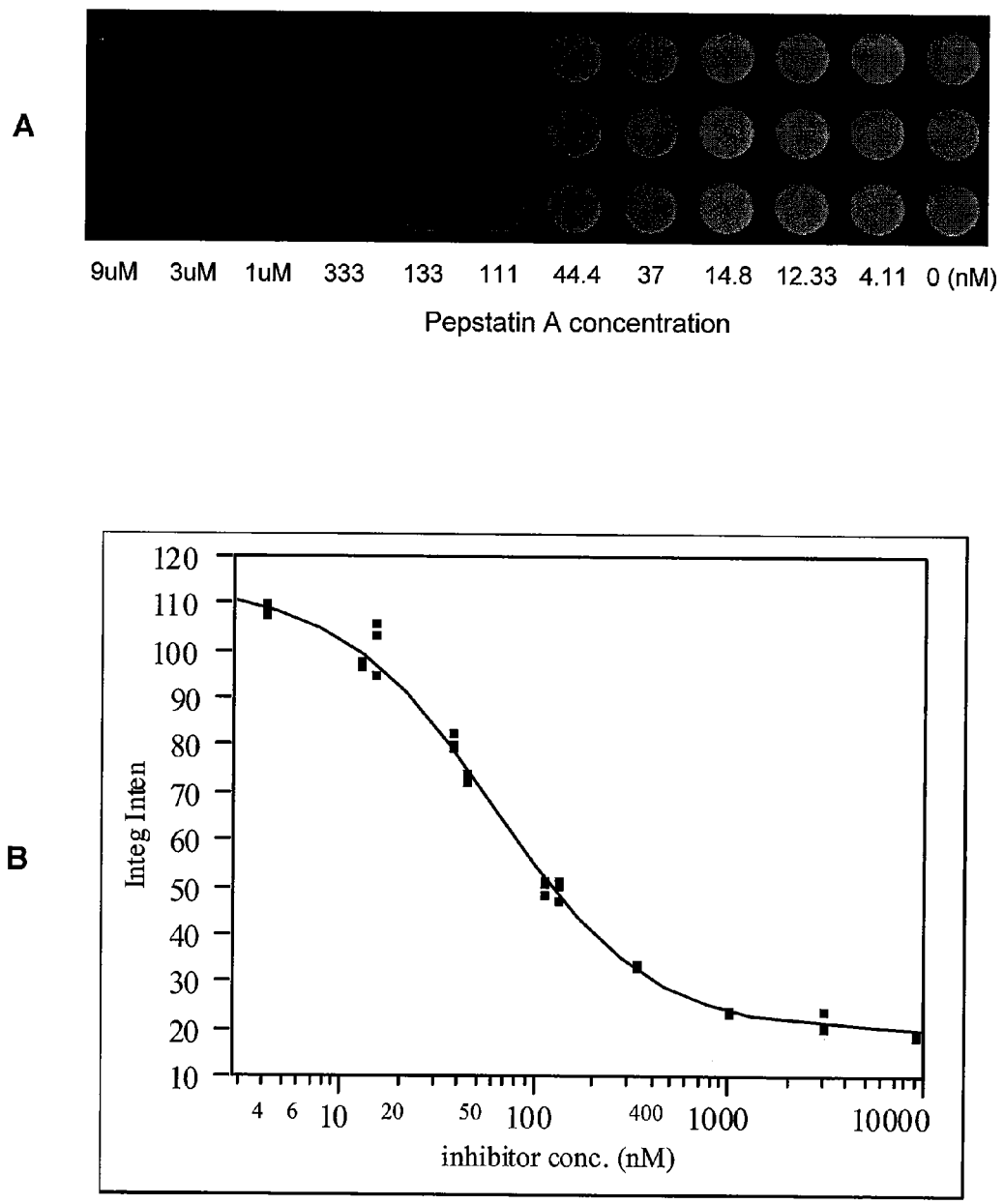
FIGS. 5A and 5B pertain to the inhibition of HIV-1 protease by pepstatin A.

The results shown in FIGS. 5A and 5B clearly show that the protease activity is substantially suppressed by the Pepstatin A at high inhibitor concentration. The substrate conversion in this assay is around 14%. At this level of substrate conversion, the measured apparent $IC_{50}$ is very close the real $IC_{50}$ (*J. of Biomolecular Screening*, 2003, 8(6), 694-700).

Using the Rodbard model for the data fitting:

$$f(x) = \frac{a-d}{\left[1+\left(\frac{x}{c}\right)^b\right]} + d$$

where f(x) is the measured response, x is the inhibitor concentration (nM), a and d is the response at zero and infinite inhibitor concentration respectively, and c is the $IC_{50}$ value, the concentration gives 50% inhibition. The fitting results are plotted against the original data and also summarized in the calculated four parameters table (see, Table 1). The $IC_{50}$ value of Pepstatin A inhibitor measured by this assay is determined to be 62 nM with very small fitting error. This $IC_{50}$ value is close to the literature reported values of 17 nM (*Science*, 1990, 247(4945), 954-958).

Table 1

Rodbard Model Fitting Results

| Parameter | Estimate | Approx. Std. Error | Lower CL | Upper CL |
|---|---|---|---|---|
| a | 113.817941 | 2.36633476 | 109.457325 | 119.140799 |
| b | 1.08930019 | 0.07118506 | 0.94924121 | 1.24235905 |
| c | 62.1247371 | 4.04760748 | 54.0701049 | 70.451653 |
| d | 19.5038477 | 1.16504927 | 16.9917716 | 21.8397036 |

Example 9

Figure 6:
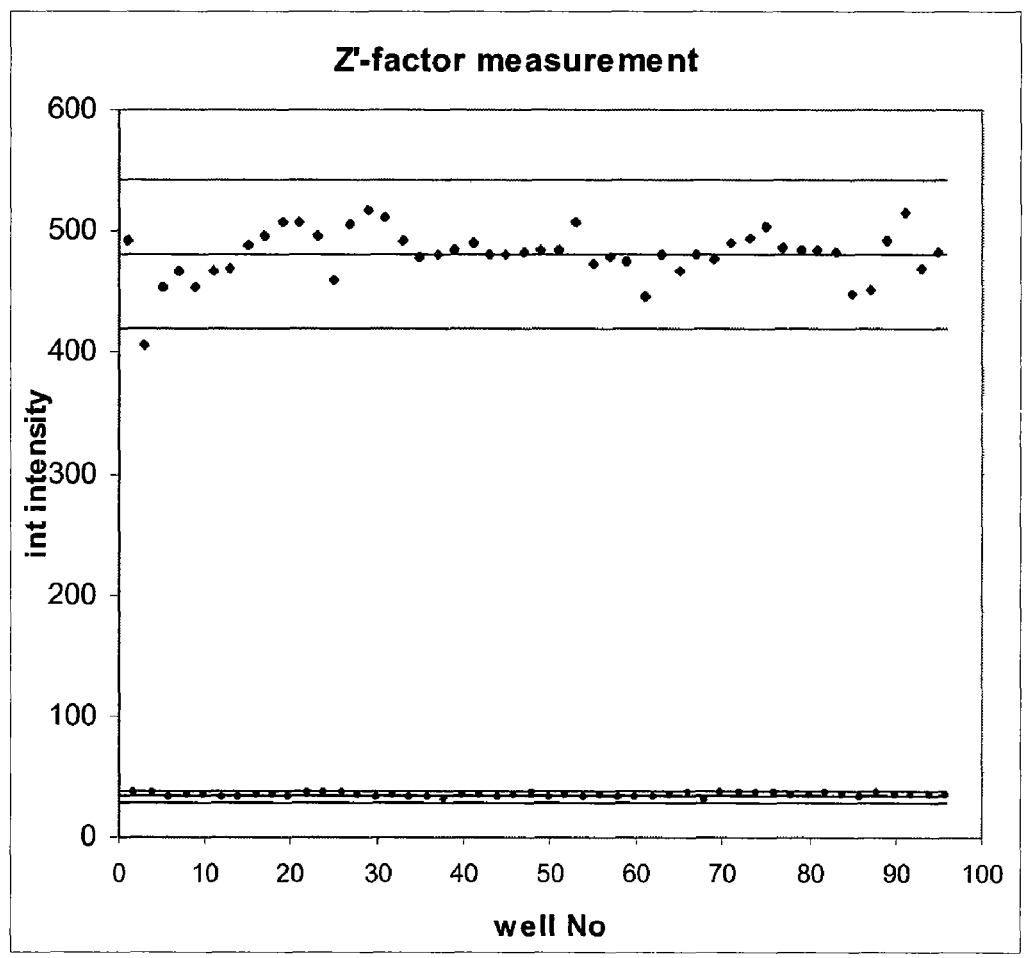
FIG. 6 shows the Z' factor analysis of a HIV-1 protease assay of the invention.

Z'-factor of the HIV-1 Protease Assay:

The Z'-factor of the assay is determined according to Zhang et al. (Zhang, J.-H., et al., *J. Biomol. Screening*, 1999, 4(2), 67-73), and is used to evaluate the quality of the HIV-1 protease assay for suitability for high-throughput screening (HTS). The peptide substrate (1 uM) was incubated with 80 nM HIV-1 protease in 48 replicates at 37° C. for 1.5 hours to serve as the positive controls and the peptide substrate (1 µM) was incubated with blank assay buffer (i.e., without HIV-1 protease) in 48 replicates at 37° C. for 1.5 hours to serve as the negative controls. The plate was then stopped and diluted by stop buffer for scanning (Aerius® Automated Infrared Imaging System). The result is shown in FIG. 6.

Z'-factor was defined by Zhang et al. as follows:

$$Z' = 1 - \frac{(3\sigma_{c+} + 3\sigma_{c-})}{|\mu_{c+} - \mu_{c-}|}$$

where $\mu_{c+}$ is the mean of positive controls; $\mu_{c-}$ is the mean of negative controls; $\sigma_{c+}$ is the standard deviation of positive controls; $\sigma_{c-}$ is the standard deviation of negative controls. The Z'-factor calculated from this experiment is determined to be 0.85. According to the Zhang et al., an assay with Z'-factor ranged from 0.5 to 1 is categorized as an excellent assay.

Example 10

Figure 7:
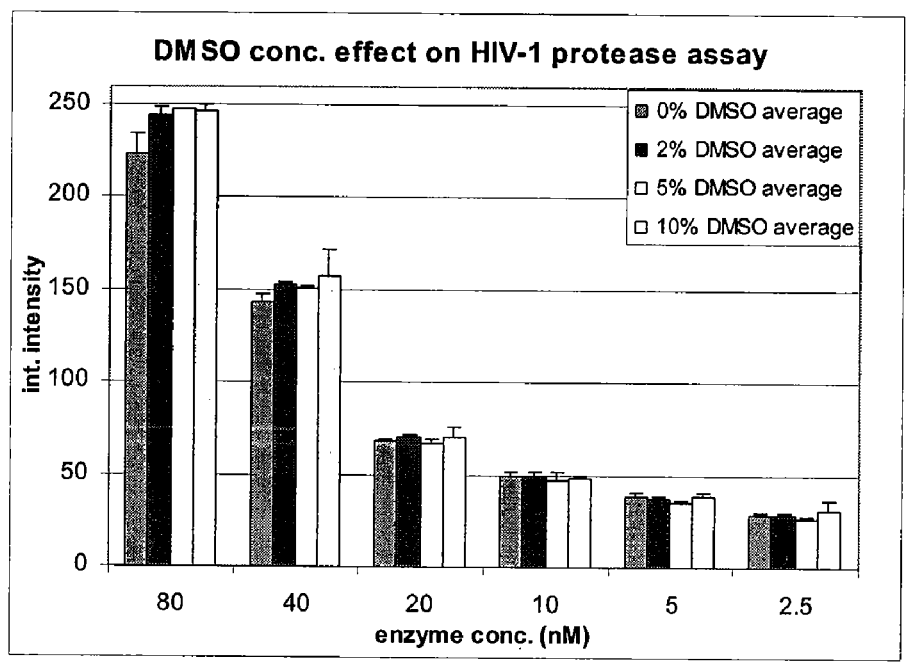
FIG. 7 shows the effect of DMSO on a HIV-1 protease assay of the invention.

Effect of DMSO on the HIV-1 Protease Assay:

To measure the tolerance of the HIV-1 protease assay to the presence of dimethyl sulfoxide (DMSO), 1 µM of substrate was incubated with 80 nM, 40 nM, 20 nM, 10 nM, 5 nM and 2.5 nM of HIV-1 protease in an assay buffer containing 10%, 5%, 2.5% or 0% DMSO. After incubation at 37° C. for 1.5 hours, the plate was treated with 0.8 M sodium phosphate stop buffer and then scanned on Aerius® System (LI-COR® Biosciences). The results are shown in FIG. 7.

The results indicate that DMSO concentrations of 0%, 2.5%, 5% and 10% have no significant effect on the cleavage of peptide substrate at any given protease concentration. In another words, the protease assay will have identical performance when operating at any DMSO concentration. This is a superior feature of this assay as compared to the other commercially available HIV-1 protease assay. Many of the commercially available HIV-1 protease assays require a DMSO concentration of 10% due to the poor solubility of enzyme substrate.

Example 11

Effect of Compound Interferences on the HIV-1 Protease Assay:

The robustness of the protease assay was evaluated against fluorescent, color quenching and light scattering interferences, which are the three major sources of compound interferences in high-throughput fluorescent assay screening. In these experiments, protease activity of the HIV-protease assay of the invention was measured in the presence of various amounts of the interference source and compared to that in the absence of the interference.

Figure 8:
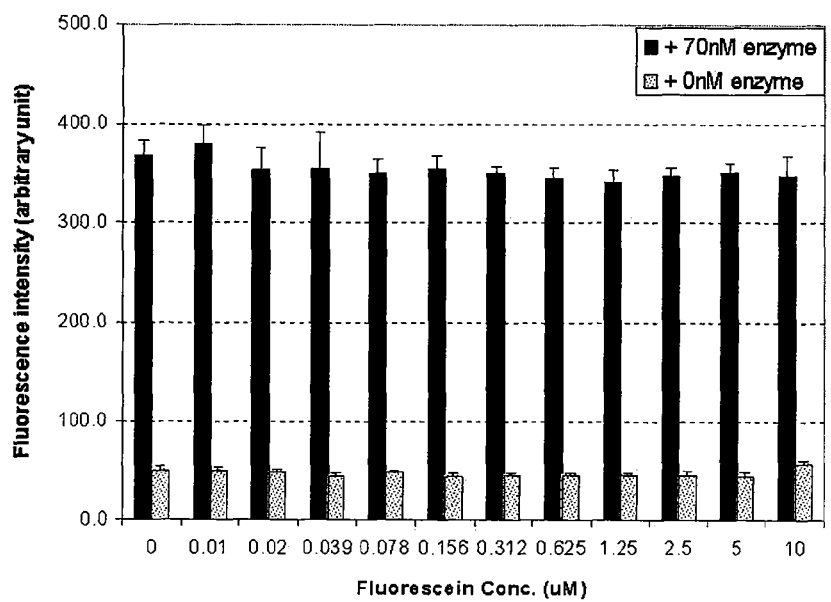
FIGS. 8A-8C show the HIV-1 protease assay of the invention performed in the presence of various components that can interfere with the sensitivity of the assay.
Figure 8:
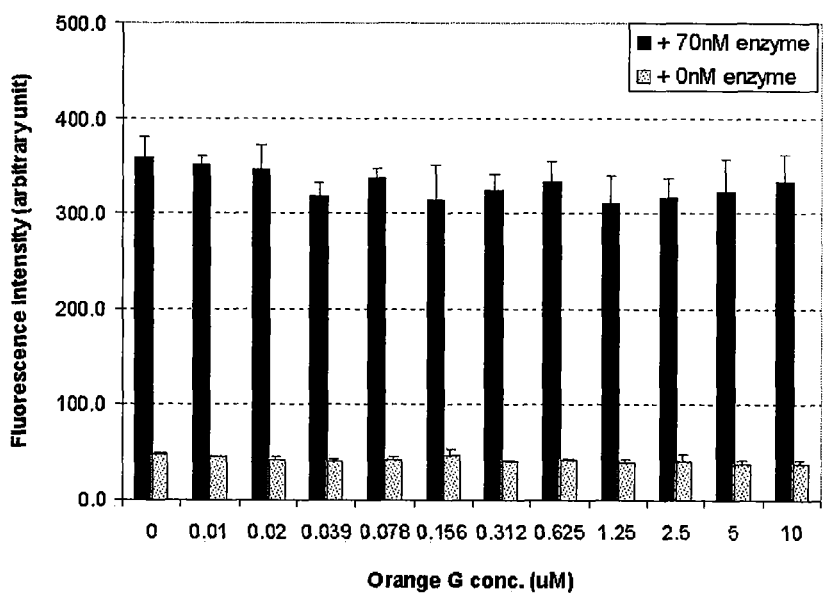
Figure 8:
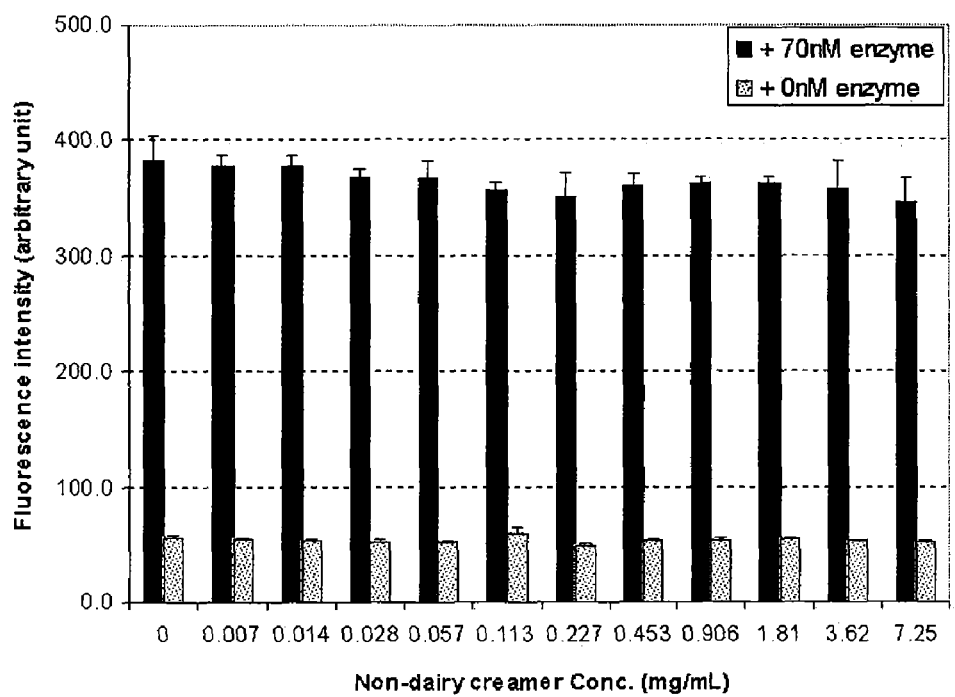

Fluorescein, a highly fluorescent compound, was chosen as the model fluorescent compound interference source. A series of fluorescein concentrations were mixed with the HIV-1 peptide substrate in the assay buffer system. These wells were then treated either with the enzyme (positive wells) or without the enzyme (negative wells) and incubated at 37° C. for 1 hour. The effect of fluorescein concentration on the near-IR fluorescent signal is summarized in FIG. 8A. FIG. 8A clearly shows that the presence of fluorescein, a highly-fluorescent material, into the system does not affect the signal in the negative or positive wells up to 10 µM fluorescein. FIG. 8A also shows that the presence of a high concentration of fluorescein did not have any inhibitory effect on enzyme activity, since the positive control wells all give almost equal substrate conversions.

Color quencher compounds, also referred to as non-fluorescent light absorbers, are another important interference source in high throughput screening assays through the attenuation of the excitation light. Orange G was used as the model color quencher compound and evaluated in the HIV-1 protease assay of the invention. As shown in FIG. 8B, the positive wells (70 nM enzyme) and negative (no enzyme) wells both exhibit good signal consistency regardless of the concentration of Orange G. This indicates that the assay is not subject to interference from color quencher compounds through attenuation of the excitation light even at very high color quencher concentration (10 µM).

Interference from scattered light was tested using non-dairy creamer as the light scattering source. The assay signal prior to completion of the enzymatic reaction was examined before adding non-dairy creamer. The protease substrate (1 µM) was dissolved in the assay solution with the enzyme (70 nM) or without the enzyme and then incubated at 37° C. for 1 hour. Next, various amounts of non-dairy creamer were added to the stopped enzymatic reaction wells (from 0.007 to 7.25 mg/mL). The results shown in FIG. 8C confirm that light scattering interference is not significant for the HIV-1 protease assay system.

The insensitivity of the HIV-1 protease assay of the invention to common sources of interference allow the protease assay to provide reduced measurement variability and much higher Z-factors in screening of compound libraries.

Example 12

Described below is a general method based on the over labeling of casein, with a near-infrared dye, i.e., NIR Reporter Dye B (a NIR-dye labeled casein substrate), for a protease activity microplate assay. The model protease assay uses the labeled casein as the substrate with trypsin as the enzyme, and the fluorescence emission is measured on a LI-COR® Biosciences' Aerius® microplate reader. NIR Reporter Dye B emits at 786 nm, yet it is still a very bright dye (see, FIG. 10).

The proteolytic reactions are carried out in 96-well plates with 50 mM TRIS buffer pH 7.8. For each reaction well, NIR-casein substrate concentration is at 20 nM, and the trypsin concentration is from 5 µg/mL down to 20 ng/mL. (The reagent NIR Reporter Dye A and its protein labeling and purification protocols are from LI-COR® Biosciences. Casein, trypsin, and aprotinin are all purchased from Sigma-Aldrich. Protein molecular weight markers labeled with a 700 nm fluorescence dye are from LI-COR® Biosciences.) The reactants are incubated at 37° C. for one hour and then stopped by adding aprotinin to 10 µg/mL final concentration. Then, after being spun, the plates are read on an the LI-COR® microplate reader Aerius®.

Figure 12:
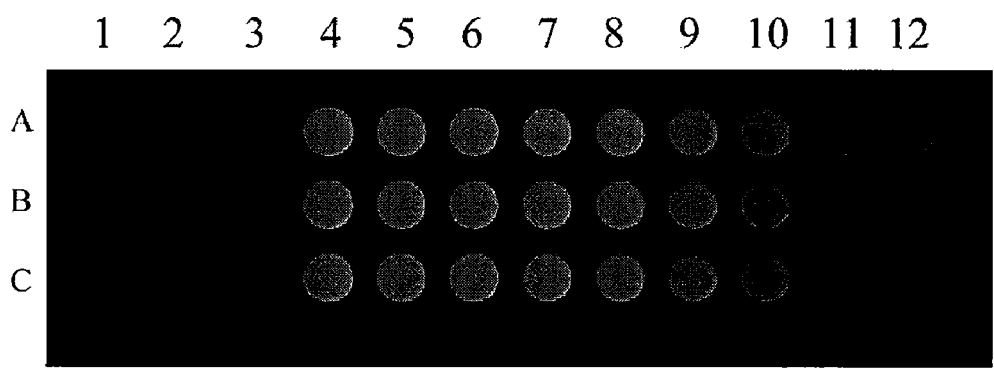
FIG. 12 shows the results of a protease assay of the invention using NIR Reporter Dye B labeled casein as the substrate and trypsin as the enzyme. Rows A, B, and C are three replicates. Column 1 contains buffer only; column 2 contains trypsin only; and column 3 contains substrate only (casein labeled with NIR Reporter Dye B). Columns 4 to 12 contain NIR Reporter Dye B labeled casein and trypsin (in a dilution series): 5 µg/mL, 2.5 µg/mL, 1.25 µg/mL, 0.625 µg/mL, 0.313 µg/mL, 0.157 µg/mL, 78.5 ng/mL, 39.3 ng/mL, and 19.7 ng/mL, with constant substrate concentration of 20 nM in 50 mM Tris Buffer pH 7.8. The intensity of column 3 in FIG. 12 is set to one.

As shown in FIG. 12, after the conjugated casein substrate is digested by trypsin, fluorescence intensity is significantly increased and this enhancement factor is correlated to the enzyme amount. Quantitatively, the NIR dye fluorescence intensity is plotted against the trypsin concentration (see, FIG. 13), and the detection dynamic window from no enzyme to 5 µg/mL is consistently up to 20-fold as compared with only 5-fold enhancement from other commercial assays. This NIR based assay only requires 1/10th the labeled substrate amount and offers a 100-fold lower trypsin detection limit than typical fluorescence-based protease assays.

To test the protease assay's robustness in rejecting background fluorescence, the above describe protease assay is performed with the addition of 100 nM fluorescein to the reaction well. The result is almost identical to that obtained in the absence of fluorescein. The NIR-dye fluorescence intensity of the wells in the presence and absence of fluorescein are plotted together in FIG. 13. The combination of the ultra-sensitivity and robustness of this NIR based protease assay clearly is clearly superior to existing visible dye based protease assays.

Figure 14:
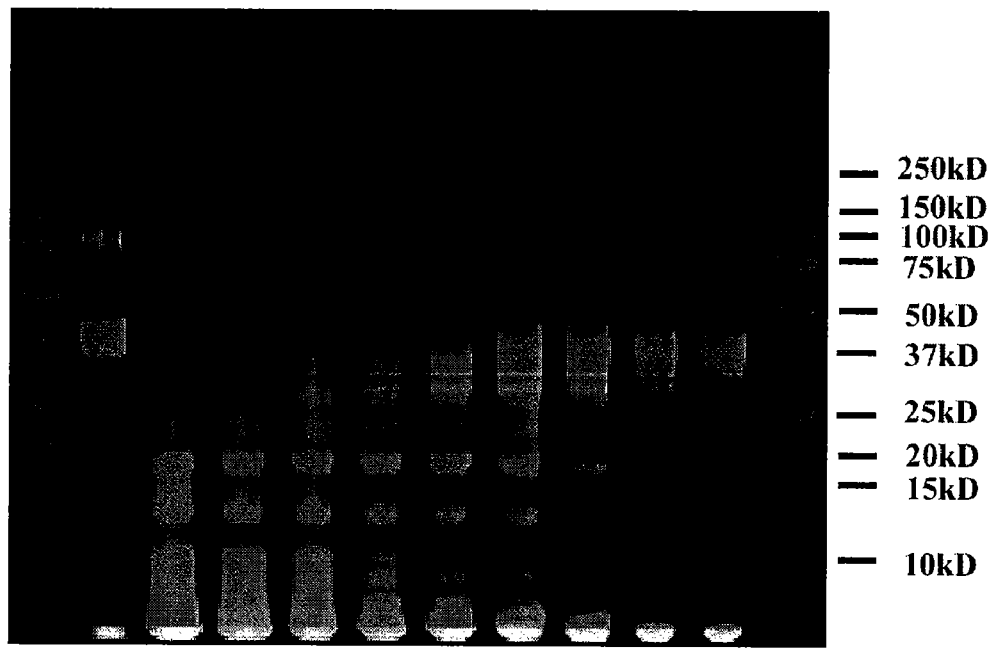
FIG. 14 shows a 10% polyacrylamide gel performed on casein labeled with NIR Reporter Dye B/trypsin digestion. Lane 1 shows casein labeled with a NIR Reporter Dye B as reference; lane 2 to lane 10: shows the dilution series in FIG. 12 from column 3 to column 12 with decreasing trypsin amounts. The image was obtained on Odyssey® scanner.

In order to demonstrate that NIR-dye fluorescence enhancement after digestion is indeed from the fragmentation of NIR-labeled casein, a polyacrylamide gel of the proteolytic reaction products was performed. The gel image is shown as FIG. 14. As the image shows, higher trypsin amount leads to higher amount of smaller (faster moving) bands on the gel. These results confirm the direct correlation between higher fluorescence intensity and higher amounts of small NIR-dye tethered fragments, hence intensity enhancement is, indeed, a result of proteolytic activity.

Figure 15:
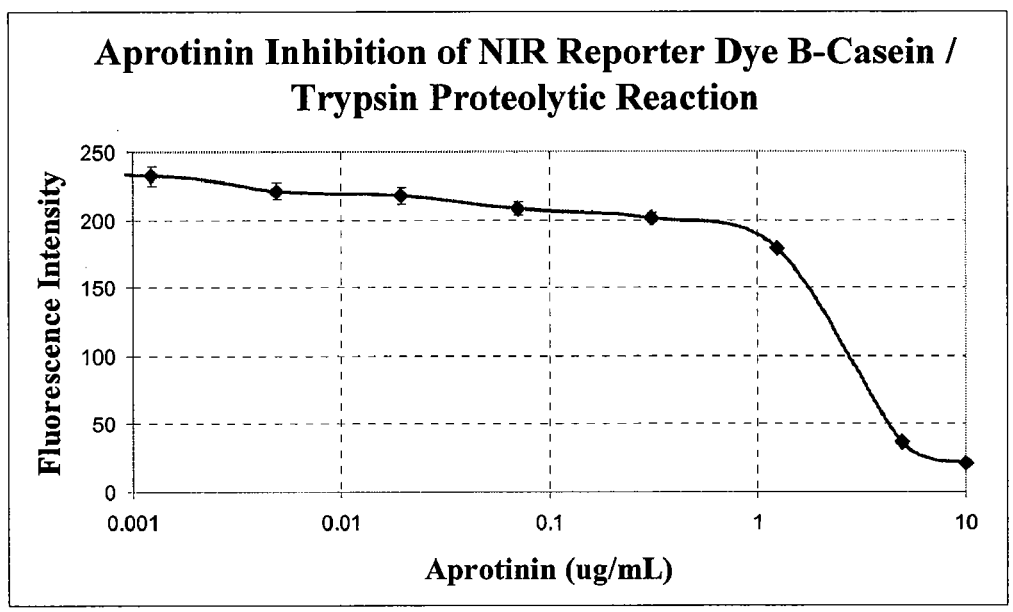
FIG. 15 shows the inhibition of casein-NIR Reporter Dye B conjugate digestion with trypsin using varying concentrations of aprotinin. Casein-NIR Reporter Dye B concentration is 20 nM, trypsin concentration is 5 µg/mL, and aprotinin concentration varies from 10 µg/mL, 5 µg/mL, 1.25 µg/mL, 0.31 µg/mL, 78 ng/mL, 19.5 ng/mL, 4.9 ng/mL, to 1.2 ng/mL. Trypsin was pre-incubated with the inhibitors for 1 hour at 37° C.

To show that the NIR-casein protease assay can also be used in studying protease inhibition and inhibitor screening, a model trypsin inhibition study using aprotinin, a known trypsin inhibitor was performed. The fluorescence intensity change between total trypsin activity suppression (at 10 µg/mL aprotinin concentration) and no inhibition is more than 20-fold (see, FIG. 15). In contrast, only a 2-fold inhibition dynamic window is observed when BODIPY FL is used in a similar assay. Due to minimal background fluorescence interference in the NIR range, this NIR-based assay produces much tighter fluorescence measurement data, which, in turn, allows for the detection of low inhibitory activities from potential protease inhibitors, which otherwise would not be possible using visible probes.

Example 13

Figure 13:
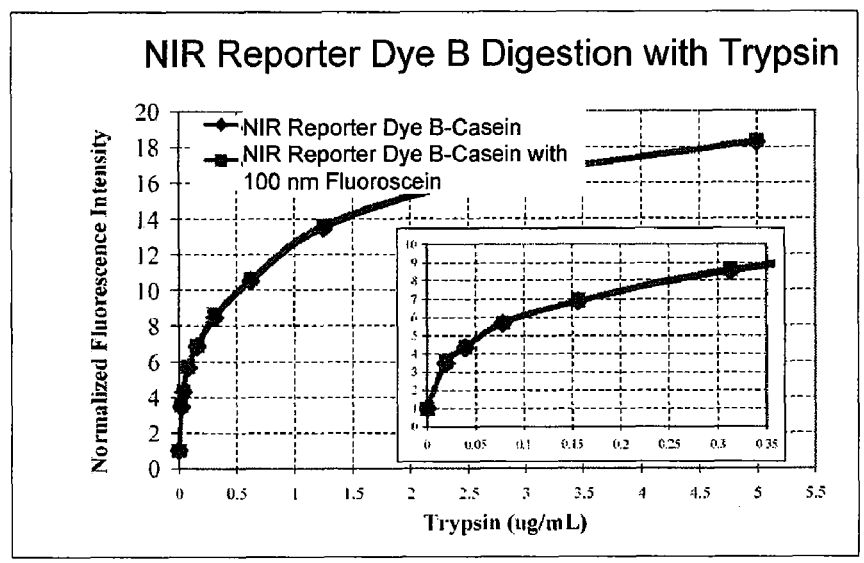
FIG. 13 shows the normalized fluorescence intensity of NIR Reporter Dye B reading on Aerius® of the microplates in the presence and absence of fluorescein.

A Comparative Study:

A enzyme assay was performed using casein having attached thereto a plurality of near-infrared dyes of formula II as the conjugated substrate and trypsin as the enzyme. The increase in fluorescence intensity of the dyes upon degradation of conjugated casein by trypsin is monitored and the result is shown in FIG. 13. For comparison, a similar enzyme assay using casein labeled with borapolyaza-s-indacene fluorescent dyes is described in FIG. 2 and Example 4 of U.S. Pat. No. 5,719,031, incorporated herein by reference, in its entirety. The inventive casein substrate and assay is more sensitive and superior to that disclosed in the '031 patent.

Example 14

BACE-1 Protease Assay Configuration:

Purified human recombinant β-secretase (BACE-1) is purchased from Calbiochem (CA). The batch size of 50 μg is supplied as a mixture of the ~68-70 KDa proenzyme and the ~65-67 KDa mature enzyme in lyophilized form from sterile-filtered 150 mM NaCl, 50 mM Tris-HCl, pH 7.5. The product is then re-constituted with 100 μL sterile water immediately prior to use.

The BACE-1 assay buffer consists of 50 mM sodium acetate, 10 mM Tris-HCl, 10 mM NaCl, 0.002% Triton X-100, pH adjusted to 4.5. The BACE-1 stop buffer is a 0.8 M sodium phosphate buffer with 0.25 mg/mL BSA (pH 7.8). A characterized BACE-1 inhibitor, β-secretase inhibitor III, is purchased from Calbiochem (CA) (Cat # 565780). The 96-well clear- and flat-bottom, black-wall microtiter plates are purchased either from BD Bioscience (BD falcon™ microtest 96-well assay plate, Optilux™, cat #: 353948) or from Corning Costar (96-well black clear-bottom plate, Corning cat # 3603), and the 384-well clear- and flat-bottom, black-wall microtiter plates are purchased from Nunc (Cat # 242764) to ensure the best performance of the assay. The Aerius® Automated Infrared Imaging System (LI-COR® Biosciences) is a two-color multiplexing detection system with user-adjustable resolution from 20 to 500 um. Two solid-state diode lasers at 680 nm and 780 nm are used as the excitation light sources and their corresponding fluorescence detection is accomplished by two silicon avalanche photo-diodes at 710±10 nm and 810±10 nm. The system is fully automated and integrated with Bio-Tek® Bio-Stack™ Automated Microplate Stacking System. The plate is scanned on Aerius® Automated Infrared Imaging System using the following instrumentation setting: Scan resolution, 200 μm; Focus offset, 3.8 mm; intensity setting: 700 nm channel off, 800 nm channel set as 1.

Example 15

Figure 20:
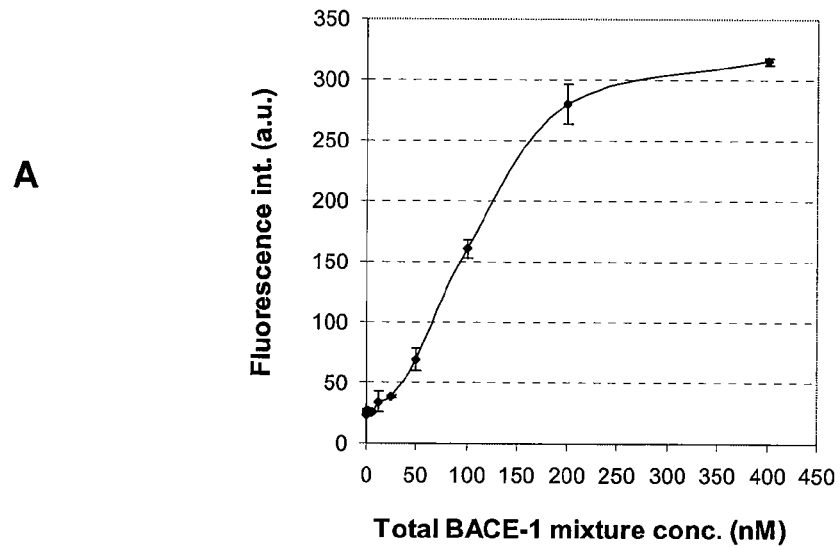
FIGS. 20A-C pertains to an BACE-1 enzyme activity assay of the invention.
Figure 20:
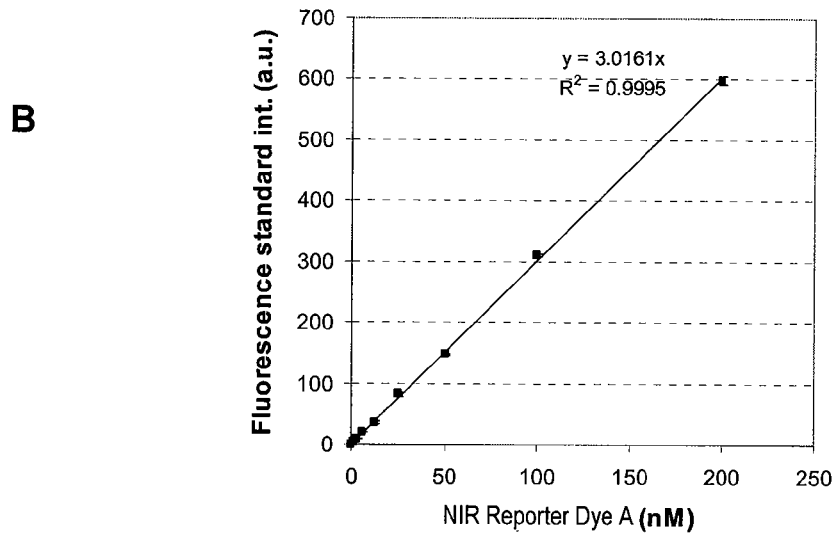
Figure 20:
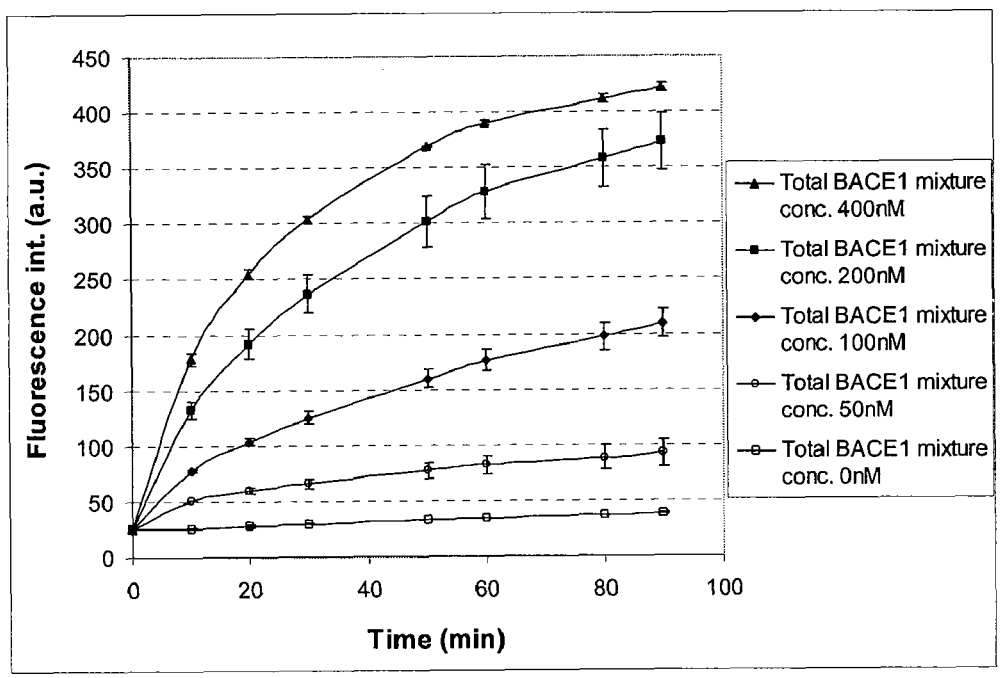

BACE-1 Enzyme Activity Assay:

The effect of enzyme concentration on proteolytic activity of the β-secretase (β-site amyloid precursor protein cleaving enzyme 1; BACE-1), is shown in FIGS. 20A-C. The BACE-1 protease substrate, (Structure IV) (in a concentration 200 nM) was incubated with BACE-1 enzyme (total enzyme mixture from 0.39 nM to 400 nM) in a BACE-1 assay buffer at room temperature for 100 minutes. The enzymatic reaction was stopped by addition of BACE-1 stop buffer and the fluorescence was recorded by Aerius® infrared imaging system. The fluorescence intensity of the protease substrate treated with the BACE-1 enzyme increased 12-fold in 100 minutes over the fluorescence intensity of protease substrate not treated by BACE-1 enzyme, due to proteolytic cleavage by BACE-1 enzyme resulting in the restoration of fluorescence of the reporter group (total BACE-1 mixture concentration 400 nM) (FIG. 20A). Based on the fluorescence standard curve obtained (FIG. 20B), the degree of hydrolysis of BACE-1 peptide was determined as 53%. With increased amount of hydrolysis, higher fluorescence increase is expected.

The results of time course experiments using various amounts of BACE-1 enzyme (50 nM, 100 nM, 200 nM, 400 nM), or without BACE-1 enzyme together with 200 nM the BACE-1 protease substrate at room temperature are shown in FIG. 20C. In the absence of BACE-1 protease enzyme, the fluorescence of BACE-1 protease substrate (Structure IV) remains low and unchanged throughout the incubation time (90 minutes). The fluorescence of the substrate in the presence of BACE-1 enzyme increased according to the amount of BACE-1 concentration and the incubation time. The continuous capability of this assay method is very useful for the enzyme kinetic measurement.

Example 16

Figure 21:
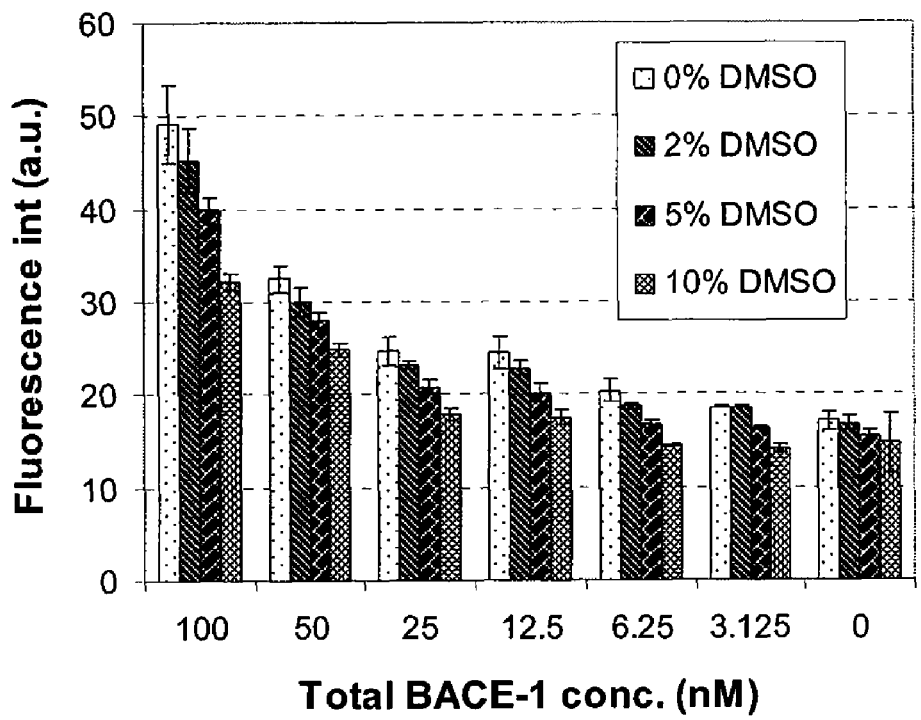
FIG. 21 illustrates the effect of DMSO concentration on BACE-1 enzymatic activity.

Effect of DMSO Concentration on the BACE-1 Enzyme Activity:

The effect of DMSO concentration on the BACE-1 enzyme activity is shown in FIG. 21. In this experiment, the BACE-1 protease substrate having Structure IV (200 nM), was incubated with various amounts of BACE-1 protease enzyme (0 to 100 nM) and DMSO concentrations (e.g., 0, 2, 5 or 10%) at room temperature for 1 hour. The enzymatic reactions were then terminated upon the addition of stop buffer and the fluorescence intensities were measured on an Aerius® imaging system. The addition of stop buffer further diluted the DMSO concentrations in the reaction solution from 0, 2, 5, 10% DMSO to 0, 0.5, 1.25, 2.5%, respectively. The change in fluorescence intensity observed for the different DMSO concentrations is a reflection of the interference of DMSO on the BACE-1 enzyme activity. As shown in FIG. 21, DMSO concentration at 2% has slight reduction (within 10%) of the BACE-1 protease enzyme activity throughout the enzyme concentration range compared with the BACE-1 protease activity at the absence of DMSO. DMSO concentration increase to 5% and 10%, the BACE-1 enzyme activity decreased 20% and 35% respectively of the original enzyme activity at the absence of DMSO throughout the enzyme concentration range.

Example 17

Figure 22:
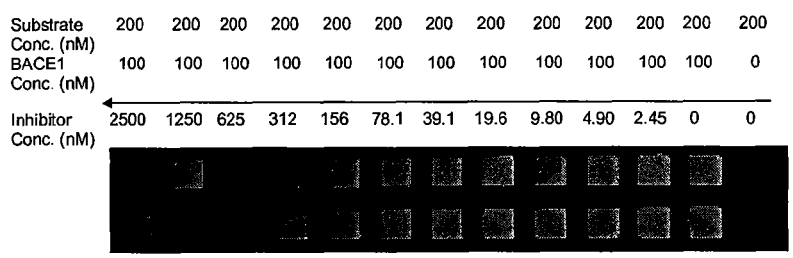
FIGS. 22A-B pertains to an BACE-1 enzyme inhibition assay of the invention by a Statine inhibitor.
Figure 22:
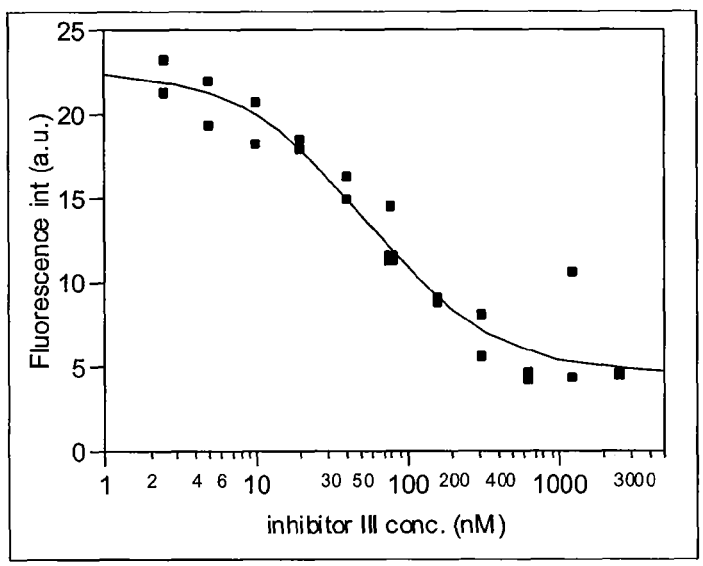

BACE-1 Enzyme Inhibition Assay:

The inhibitor concentration at 50% inhibition ($IC_{50}$) of a characterized Statine-derived peptide inhibitor of BACE-1 (i.e., H-Glu-Val-Asn-Statine-Val-Ala-Glu-Phe-$NH_2$; SEQ ID NO:11), is measured by using this assay method. The serially diluted solutions containing the BACE-1 peptide inhibitor (final concentrations from 0 to 2500 nM) were mixed with BACE-1 in BACE-1 assay buffer (total BACE-1 mixture final concentration of 100 nM) for 15 minutes followed by the addition of the BACE-1 protease substrate having Structure IV in a final concentration 200 nM. After incubating the reaction solutions at room temperature for 1 hour, the enzymatic reactions were terminated with BACE-1 stop buffer. The fluorescence intensity was measured on Aerius® infrared imaging system (FIG. 22A). The dose-response curve obtained in this experiment was fitted into the Rodbard model, as plotted in FIG. 22B; and the $IC_{50}$ was determined as 57 nM. The maxima substrate conversion with no inhibitor in this experiment is 67% based on the fluorescence standard intensity measurement.

Example 18

Figure 23:
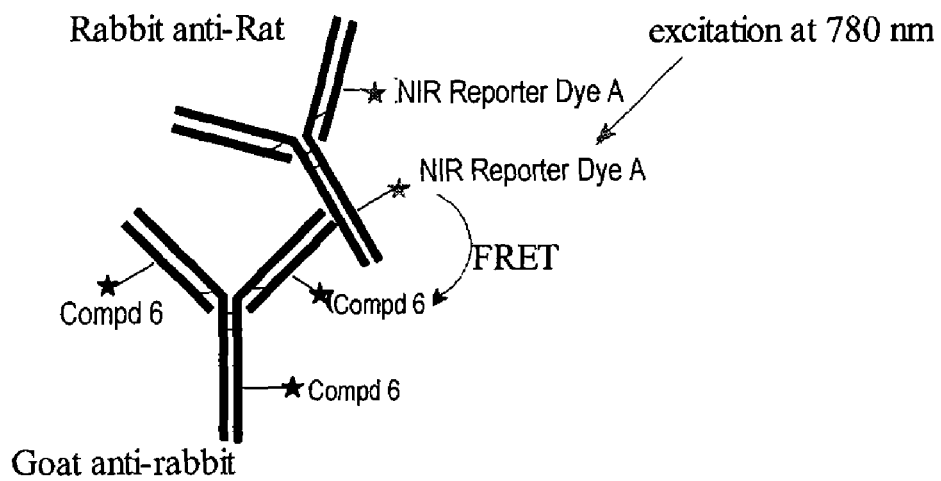
FIG. 23 shows a scheme which outlines a fluorescence quenching assay of the invention in which fluorescence of a NIR reporter dye-labeled secondary antibody of the invention is quenched using a quencher dye-labeled antibody of the invention.

Fluorescence Quenching Using Dye-Labeled Antibodies:

The following experiment demonstrates the potential application of an inventive reporter-quencher dye pair (e.g., Compound 6 (a quencher) with NIR Reporter Dye A (a reporter) in a phospho-specific antibody-based kinase assay system. In particular, it has been demonstrated in a test system as depicted in FIG. 23, that when Compound 6 that is conjugated to an antibody (Goat anti-Rabbit) is combined in an assay medium with a NIR Reporter Dye A which is conjugated to a complementary secondary antibody (Rabbit anti-Rat), the fluorescence of the reporter-labeled secondary antibody is quenched. The observed quenching in the antibody system is noteworthy because the reporter and acceptor distance is much longer due to the size of the antibodies.

Figure 24:
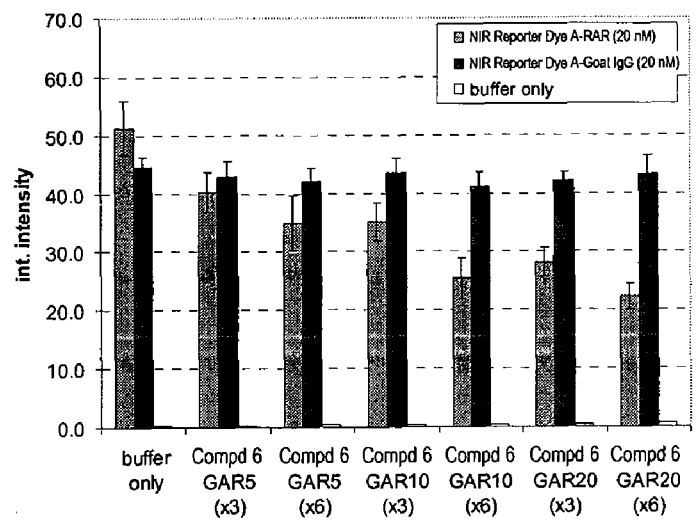
FIG. 24 shows the fluorescence intensity readout from the quenching assay performed as described in FIG. 23.

In this experiment, the (NIR Reporter Dye A)-labeled secondary antibody (Rabbit anti-Rat; RAR) was purchased from Rockland which has a dye to protein ratio (D/P) of 1.4. The antibody (Goat anti-Rabbit; GAR) was conjugated with Compound 6 at several dye to protein ratios, i.e. (D/P) of 1.4, 2.5 and 4.7. An NIR Reporter Dye A labeled antibody (Goat IgG) in a D/P ratio of 1.5, which does not bind to the goat anti-rabbit antibody, was prepared as a control. The results of this experiment (FIG. 24) show that the quencher labeled antibody (i.e., compound 6-labeled antibody (GAR)) quenched the fluorescence signal of NIR Reporter Dye A up to 55% quenching efficiency from its binding partner (RAR), while having no quenching effect of the NIR Reporter Dye A signal from its non-binding counterpart (Goat IgG). The background fluorescence from Compound 6-labeled GAR is small at conditions used in this experiment. Furthermore, it was observed that a high D/P ratio of a labeled antibody (Compd 6-GAR) is helpful to increase the quenching efficiency. For example, Compound 6-labeled Goat anti-rabbit antibody, i.e., Compd 6-GAR20 (with a D/P ratio of 4.7), has the highest quenching efficiency as compared to Compd 6-GAR5 (D/P=1.4); and Compd 6-GAR10 (D/P=2.5). Increasing the amount of -GAR has marginal improvement on its quenching efficiency for all three conjugates with different D/P ratios.

Example 19

Tyrosine Kinase Assay Using Dye-Labeled Phospho-Antibodies—A Model System:

The following experiment demonstrates the potential utility of a tyrosine kinase assay system using an inventive quencher-labeled phospho-specific antibody, i.e., Compound 6 conjugated P-Tyr-100 antibody. The P-Tyr-100 antibody binds specifically to phosphotyrosine regardless of the flank amino acid sequence in the peptide. P-Tyr-100 (cell signaling technology), is a monoclonal antibody supplied in dye conjugate-able form with 58 mM $Na_2HPO_4$, 17 mM $NaH_2PO_4$ and 68 mM NaCl (pH 7.4) for drug discovery. The conjugation of p-Tyr-100 to the quencher dye was performed by diluting the original antibody solution by equal volume of 1× PBS buffer and then mixing with the Compound 6-NHS ester at 4° C. for 4 hours. Purification of the conjugated product was accomplished by dialyzing against phosphate buffer saline (1× PBS) at 4° C. overnight. Compound 6-pTyr100 conjugates in various D/P ratios (D/P=3.5, 6.5, 8.3) were prepared. Compound 6-conjugated P-Tyr-100 antibody binds to the a phosphorylated peptide product that is conjugated to a reporter dye; and is produced in a kinase reaction as depicted FIG. 25A and described below.

A primary purpose of this experiment is to evaluate the quenching efficiency of an inventive quencher labeled-phospho-antibody (e.g., compound 6 conjugated P-Tyr-100 antibody) for application to a kinase assay. For the purpose of this experiment, the actual kinase phosphorylation reaction step is bypassed. Instead, the phosphorylated product of the enzymatic kinase reaction is mimicked using a reporter dye-labeled phospho-Src peptide, i.e., NIR Reporter Dye A conjugated to the phosphorylated Src peptide 521-533 (H-TSTEPQpYQPGENL-OH; SEQ ID NO:14). As a control, its non-phosphorylated counterpart, i.e., Src peptide 521-533 (H-TSTEPQYQPGENL-OH; SEQ ID NO:15), was also prepared, to assess the specificity of the quencher conjugated P-Tyr-100 antibody for the phosphorylated product. This experiment was performed in a HEPES buffer system containing 20 mM HEPES, 10 mM $MgCl_2$, 0.1% BSA, and also 0.01% Tween-20.

Figure 25:
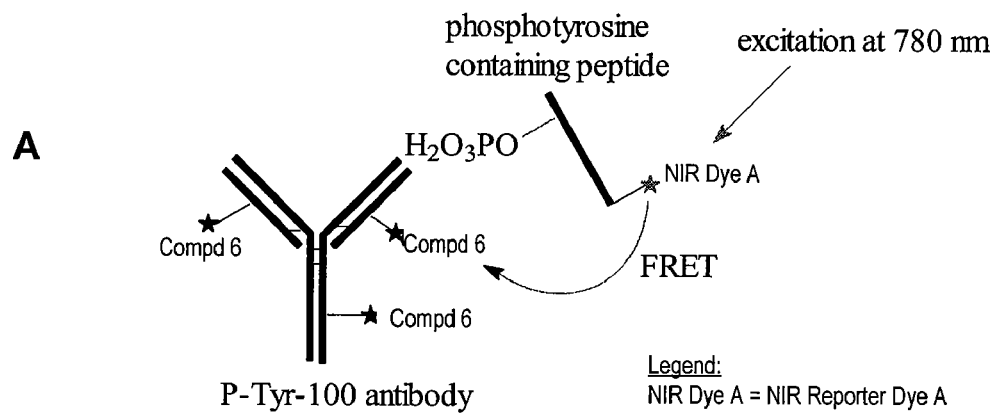
FIGS. 25A-B pertains a model tyrosine kinase assay of the invention.
Figure 25:
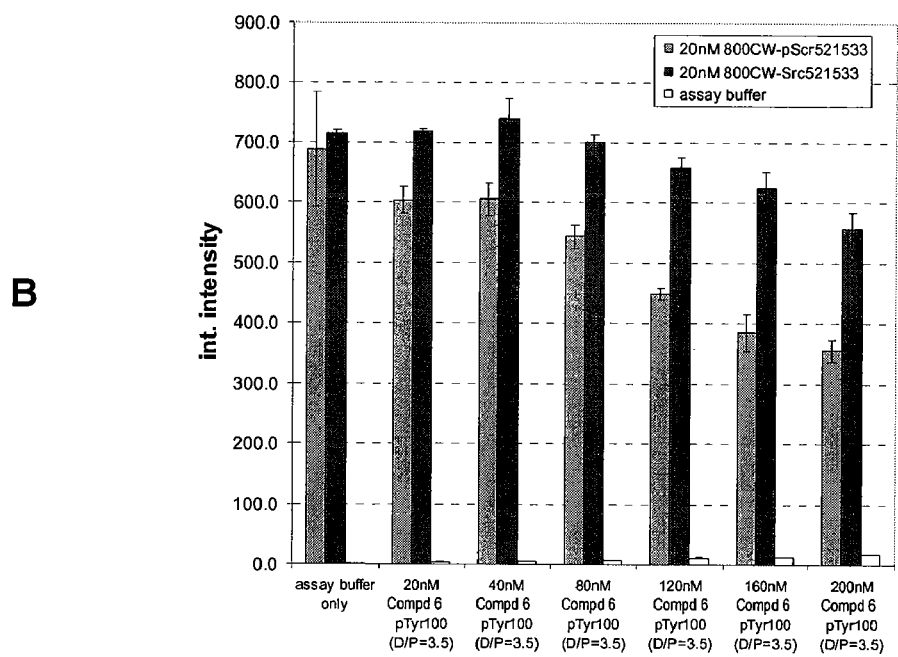

Shown in FIG. 25B is the quenching efficiency test result for the Compound 6-pTyr100 conjugate with D/P ratio 3.5. Compound 6 conjugated pTyr100 (Compd 6-pTyr100), from 0 nM to 200 nM concentrations, is incubated with a phosphorylated tyrosine or a non-phosphorylated tyrosine substrate having a reporter dye (i.e., NIR Reporter Dye A) attached thereto. As shown in FIG. 25B, as the Compd 6-pTyr100 conjugate concentration is increased to 200 nM, the fluorescence intensity by the reporter dye conjugated to the phosphorylated tyrosine peptide (i.e., (NIR Reporter Dye A)-pSrc521-533 peptide) decreases. Interestingly, when high concentrations of a quencher conjugated antibody is incubated with the reporter dye labeled non-phosphorylated peptide, i.e., 20 nM (NIR Reporter Dye A)-Src521-533 peptide a decrease in fluorescence (about 20% decrease) is also observed. Since the non-phosphorylated peptide has no binding epitope to the pTyr100, it would have been expected that the fluorescence signal of the non-phosphorylated peptide to remain constant regardless of the amount Compd 6-pTyr100 present. This loss in fluorescence with the non-phosphorylated substrate suggests that there may be some sort of non-specific binding affinity for the non-phosphorylated peptide for the quencher labeled p-Tyr-100 antibody. The intrinsic fluorescence of the Compound 6-labeled pTyr100 antibody is very low.

Example 20

Evaluation of Fluorescence Intensity Change as a Function of Substrate Conversion:

In a kinase assay, it is useful to be able to detect a linear response in the conversion of a substrate to product, e.g., in the conversion of the Scr 521-533 peptide to its phosphorylated product. A series of wells were prepared containing from 0% to 100% phosphorylated peptides (using a combination of phosphorylated-Scr 521-533 and non-phosphorylated-Scr 521-533 peptides) having the reporter dye (NIR Reporter Dye A) attached thereto. To each well was added the Compound 6-pTyr100 conjugate, and the plate was incubated, then recorded on LI-COR's Odyssey® Infrared Imaging System. In each well, the final concentration of the Scr 521-533 peptide regardless of its phosphorylation state is 20 nM and the concentration of the Compound 6-pTyr100 conjugate is 200 nM.

Figure 26:
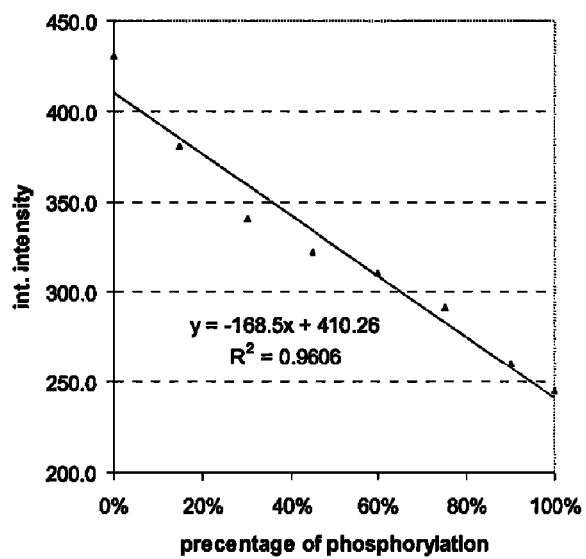
FIG. 26 pertains to an experiment to evaluate the fluorescence intensity change in a tyrosine kinase assay of the invention as a function of substrate conversion.

The signal decreases with respect to the increase of the degree of phosphorylation as shown in FIG. 26. The linear regression fitting shows a good correlation coefficient (R2=0.96). The fluorescence intensity signal change window is approximately 2-fold, i.e., signal change from 100% phosphorylation to 0% phosphorylation.

Example 21

Enhancement of Fluorescence Intensity Signal Changes in a Kinase Assay Using Dye-Labeled Phospho-Antibodies:

To enhance the fluorescence intensity signal change window of a tyrosine kinase assay described in Example 20, a protein precipitation method is evaluated. The protein precipitation method works on the principle that, depending on the physiochemical properties of the proteins, certain proteins can be selectively precipitated out from the buffer solution if the environment of the solution (e.g., salt concentration, pH, and percentage of organic solvent) is altered. Therefore, if the phosphorylated-peptide substrate that is bound to the quencher labeled pTyr100 antibody is selectively precipitated out from the buffer solution, the supernatant should contain a lower phospho-peptide bound antibody concentration as compared to the non-phosphorylated-peptide substrate. The non-phosphorylated-peptide substrate should remain in the supernatant.

The same experiment was performed as described in Example 20. However, prior to scanning each well with the LI-COR's Odyssey® Infrared Imaging System, the phosphorylated-peptide substrate that is bound to the quencher labeled pTyr100 antibody was precipitated out of solution by the addition of methanol to the reaction solution. The fluorescence intensity of the supernatant after precipitation of the phosphorylated-peptide substrate that is bound to the quencher labeled pTyr100 antibody then was recorded. The results indicates that approximately a 3-fold signal change window can be achieved using the protein precipitation approach (using a quencher labeled antibody with a D/P ratio of 3.5).

Figure 27:
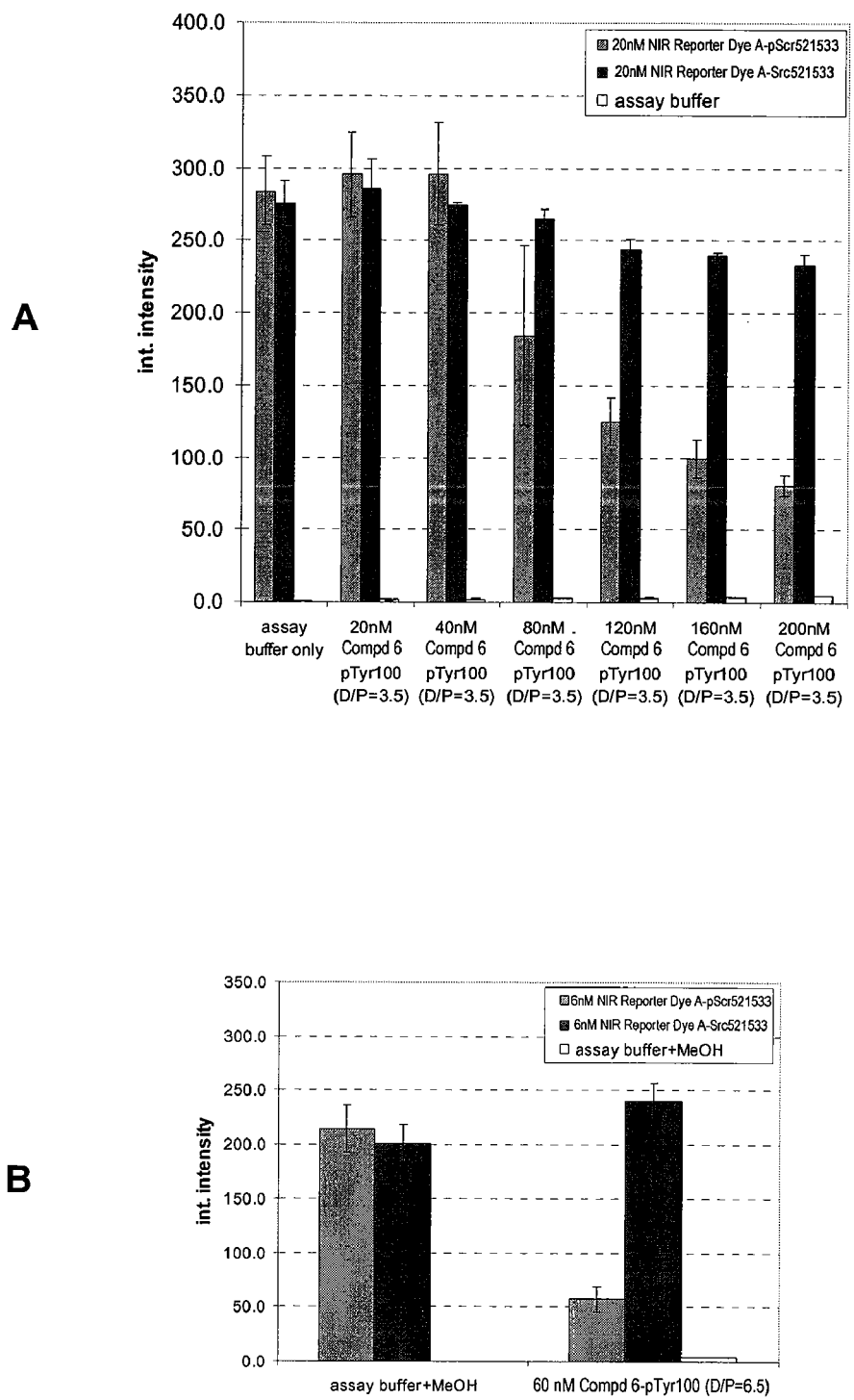
FIGS. 27A-B illustrate the results of a protein precipitation method for enhancing the fluorescence intensity signal change in the model tyrosine kinase assay. In particular.

Additionally, the signal change window, using the protein precipitation approach, can be further increased if the quencher labeled-pTyr100 antibody with an even higher D/P ratio is used in the experiment. The results of using a quencher labeled-pTyr100 conjugate with D/P ratio at 6.5 in the experiment as described in Example 20 is shown in FIG. 27B. The signal increase window improves to 4-fold using the quencher labeled-p-Tyr100 conjugate with the higher D/P ratio.

All publications, patents and patent publications mentioned in this specification are herein incorporated by reference into the specification in their entirety for all purposes. Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. An essentially non-fluorescent compound of formula Ib:

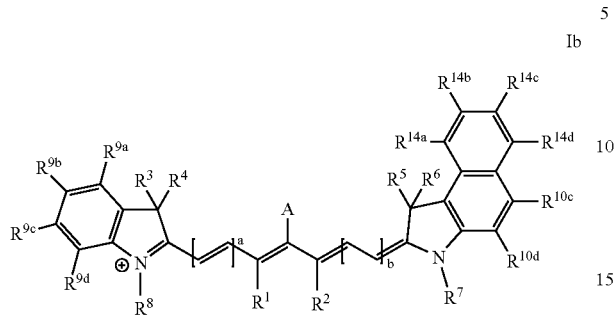

wherein:
$R^1$ and $R^2$ are each independently selected from the group consisting of hydrogen and optionally substituted ($C_1$-$C_6$)alkyl; or alternatively, $R^1$ and $R^2$ together with the

group to which they are bonded form a 5- to 7-membered ring, said ring being optionally substituted with 1 to 4 substituents selected from the group consisting of halogen, cyano, sulfonate, ($C_1$-$C_8$)haloalkyl, hydroxy, ($C_1$-$C_6$)alkoxy and optionally substituted ($C_1$-$C_8$)alkyl;

$R^3$ and $R^4$ are each an optionally substituted ($C_1$-$C_6$)alkyl, and may optionally join together with the atom to which they are attached to form a 5- to 7-membered carbocyclic ring;

or alternatively the substituents $R^3$ and $R^4$ are replaced with the group

wherein B is ($C_1$-$C_6$)alkyl; or B and $R^{9a}$ together with the carbon atoms to which they are attached join to form a 5- or 6-membered ring optionally having 1 or 2 heteroatoms and optionally having up to 3 double bonds;

$R^5$ and $R^6$ are each an optionally substituted ($C_1$-$C_6$)alkyl, and may optionally join together with the atom to which they are attached to form a ring;

$R^7$ and $R^8$ are each independently selected from the group consisting of optionally substituted ($C_1$-$C_6$)alkyl, optionally substituted aryl($C_1$-$C_6$)alkyl, optionally substituted heteroaryl($C_1$-$C_6$)alkyl, —(CH$_2$)$_c$R$^{13}$, —(CH$_2$)$_d$R$^{15}$, —(CH$_2$)$_d$C(O)OR$^{15}$, and —(CH$_2$)$_d$C(O)NH(CH$_2$)$_d$R$^{15}$, wherein c and d are each independently an integer from 1-50, $R^{13}$ is a functional group that does not directly react with a carboxyl, hydroxyl, amino or thio group on a biomolecule, $R^{15}$ is a linking group selected from the group consisting of mercapto, amino, haloalkyl, phosphoramidityl, N-hydroxysuccinimidyl ester, sulfo N-hydroxysuccinimidyl ester, isothiocyanato, iodoacetamidyl, maleimidyl and an activated carboxylic acid;

$R^{9a-9d}$ and $R^{10c-10d}$ are each independently selected from the group consisting of hydrogen, optionally substituted ($C_1$-$C_6$)alkyl, —SO$_3$Cat, halogen, —C(O)OR$^{11}$, —C(O)NR$^{11}$R$^{12}$, —C(O)O(CH$_2$)$_d$R$^{15}$, —C(O)NR$^{11}$(CH$_2$)$_d$R$^{15}$, —NR$^{12}$C(O)O(CH$_2$)$_d$R$^{15}$, —NR$^{12}$C(O)OR$^{11}$, —(CH$_2$)$_d$R$^{15}$, —S(O)$_2$NR$^{12}$(CH$_2$)$_d$R$^{15}$, —R$^{15}$ and —NR$^{20}$R$^{21}$, wherein Cat is a cation, wherein $R^{11}$ and $R^{12}$ are each independently selected from the group consisting of hydrogen and optionally substituted ($C_1$-$C_6$)alkyl; $R^{20}$ and $R^{21}$ are each independently selected from the group consisting of optionally substituted ($C_1$-$C_8$)alkyl, CatO$_3$S($C_1$-$C_{50}$)alkylene, a is an integer from 0-3;
b is an integer from 0-2; and
A is selected from the group consisting of hydrogen, halogen, cyano, optionally substituted ($C_1$-$C_8$)alkyl, optionally substituted ($C_1$-$C_6$)dialkylamino, optionally substituted alkylthio, —(CH$_2$)$_d$R$^{15}$, —R$^{15}$, optionally substituted ($C_1$-$C_6$)heteroalkyl, phenoxy, and an optionally substituted aryloxy group having the formula

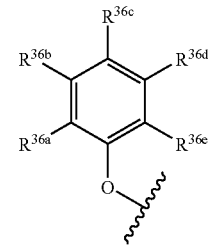

wherein $R^{36a}$-$R^{36e}$ are each independently selected from the group consisting of hydrogen, —SO$_3$Cat, —(CH$_2$)$_d$R$^{15}$, —C(O)O(CH$_2$)$_d$R$^{15}$, —C(O)NR$^{11}$(CH$_2$)$_d$R$^{15}$, —NR$^{12}$C(O)O(CH$_2$)$_d$R$^{15}$, —S(O)$_2$NR$^{12}$(CH$_2$)$_d$R$^{15}$, —R$^{15}$, ($C_1$-$C_6$)alkyl, carboxyl and NR$^{20}$R$^{21}$;

wherein said compound contains at least one linking group;

wherein said compound has at least one —NR$^{20}$R$^{21}$ group substituted at a position selected from the group consisting of $R^{10c}$ and $R^{10d}$;

wherein $R^{14a-14d}$ are each independently selected from the group consisting of hydrogen, optionally substituted ($C_1$-$C_6$)alkyl, —SO$_3$Cat, halogen, —C(O)OR$^{11}$, —C(O)NR$^{11}$R$^{12}$, —C(O)O(CH$_2$)$_d$R$^{15}$, —C(O)NR$^{11}$(CH$_2$)$_d$R$^{15}$, —NR$^{12}$C(O)O(CH$_2$)$_d$R$^{15}$, —NR$^{12}$C(O)OR$^{11}$, —(CH$_2$)$_d$R$^{15}$, —S(O)$_2$NR$^{12}$(CH$_2$)$_d$R$^{15}$, —R$^{15}$ and —NR$^{20}$R$^{21}$; and wherein said compound is essentially non-fluorescent and is charge neutral.

2. The compound of claim 1, wherein $R^{10c}$ in formula Ib is —NR$^{20}$R$^{21}$.

3. The compound of claim 1, wherein $R^{10d}$ in formula Ib is —NR$^{20}$R$^{21}$.

4. The compound of claim 1, wherein at least one of $R^{14a}$ to $R^{14d}$ is —SO$_3$Cat.

5. The compound of claim 1, wherein $R^{10c}$ and $R^{10d}$ are both NR$^{20}$R$^{21}$.

6. The compound of claim 1, of formula Ic:

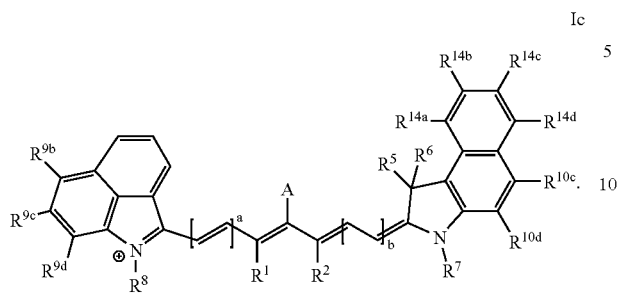

7. The compound of claim 6, wherein at least one of $R^{9b}$, $R^{9d}$ and $R^{10d}$ in formula Ic is an —$NR^{20}R^{21}$ group.

8. An essentially non-fluorescent compound of formula Id:

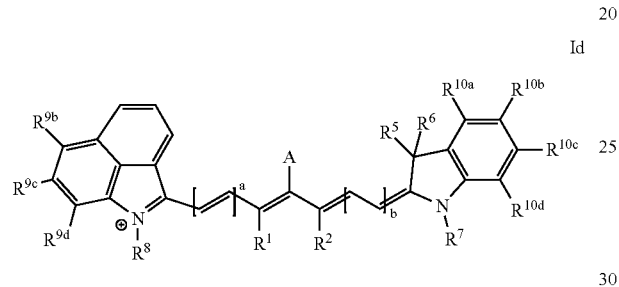

wherein:
$R^1$ and $R^2$ are each independently selected from the group consisting of hydrogen and optionally substituted ($C_1$-$C_6$)alkyl; or alternatively, $R^1$ and $R^2$ together with the

group to which they are bonded form a 5- to 7-membered ring, said ring being optionally substituted with 1 to 4 substituents selected from the group consisting of halogen, cyano, sulfonate, ($C_1$-$C_8$)haloalkyl, hydroxy, ($C_1$-$C_6$)alkoxy and optionally substituted ($C_1$-$C_8$)alkyl;
$R^5$ and $R^6$ are each an optionally substituted ($C_1$-$C_6$)alkyl, and may optionally join together with the atom to which they are attached to form a ring;
$R^7$ and $R^8$ are each independently selected from the group consisting of optionally substituted ($C_1$-$C_6$)alkyl, optionally substituted aryl($C_1$-$C_6$)alkyl, optionally substituted heteroaryl($C_1$-$C_6$)alkyl, —$(CH_2)_cR^{13}$, —$(CH_2)_dR^{15}$, —$(CH_2)_dC(O)OR^{15}$, and —$(CH_2)_dC(O)NH(CH_2)_dR^{15}$, wherein c and d are each independently an integer from 1-50, $R^{13}$ is a functional group that does not directly react with a carboxyl, hydroxyl, amino or thio group on a biomolecule, $R^{15}$ is a linking group selected from the group consisting of mercapto, amino, haloalkyl, phosphoramidityl, N-hydroxysuccinimidyl ester, sulfo N-hydroxysuccinimidyl ester, isothiocyanato, iodoacetamidyl, maleimidyl and an activated carboxylic acid;
$R^{9b-9d}$ and $R^{10a-10d}$ are each independently selected from the group consisting of hydrogen, optionally substituted ($C_1$-$C_6$)alkyl, —$SO_3Cat$, halogen, —$C(O)OR^{11}$, —$C(O)NR^{11}R^{12}$, —$C(O)O(CH_2)_dR^{15}$, —$C(O)NR^{11}$ $(CH_2)_dR^{15}$, —$NR^{12}C(O)O(CH_2)_dR^{15}$, —$NR^{12}C(O)OR^{11}$, —$(CH_2)_dR^{15}$, —$S(O)_2NR^{12}(CH_2)_dR^{15}$, —$R^{15}$ and —$NR^{20}R^{21}$, wherein Cat is a cation, wherein $R^{11}$ and $R^{12}$ are each independently selected from the group consisting of hydrogen and optionally substituted ($C_1$-$C_6$)alkyl; $R^{20}$ and $R^{21}$ are each independently selected from the group consisting of hydrogen, optionally substituted ($C_1$-$C_8$)alkyl, $CatO_3S(C_1$-$C_{50}$)alkylene,
alternatively, any two substituents of $R^{10a-10d}$ located on adjacent atoms, together with the atroms to which are attached, join to form a 5- or 6-membered ring optionally having 1 or 2 hetroatoms and optionally having up to 3 double bonds; wherein said ring may be further substituted with 1 to 3 substituents selected from the group consisting of optionally substituted ($C_1$-$C_6$)alky, —$SO_3Cat$, halogen, —$C(O)OR^{11}$, —$C(O)NR^{11}R^{12}$, —$C(O)O(CH_2)_dR^{15}$, —$C(O)NR^{11}(CH_2)_dR^{15}$, —$NR^{12}C(O)O(CH_2)_dR^{15}$, —$NR^{12}C(O)OR^{11}$, —$S(O)_2$ $NR^{12}(CH_2)_dR^{15}$, —$R^{15}$ and —$NR^{20}R^{21}$;
a is an integer from 0-3;
b is an integer from 0-2; and
A is selected from the group consisting of hydrogen, halogen, cyano, optionally substituted ($C_1$-$C_8$)alkyl, optionally substituted ($C_1$-$C_6$)dialkylamino, optionally substituted alkylthio, —$(CH_2)_dR^{15}$, —$R^{15}$, optionally substituted ($C_1$-$C_6$)heteroalkyl, phenoxy, and an optionally substituted aryloxy group having the formula

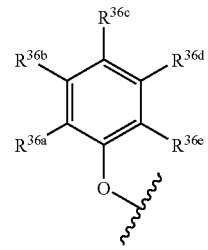

wherein $R^{36a}$-$R^{36e}$ are each independently selected from the group consisting of hydrogen, —$SO_3Cat$, —$(CH_2)_d$ $R^{15}$, —$C(O)O(CH_2)_dR^{15}$, —$C(O)NR^{11}(CH_2)_dR^{15}$, —$NR^{12}C(O)O(CH_2)_dR^{15}$, —$S(O)_2NR^{12}(CH_2)_dR^{15}$, —$R^{15}$, ($C_1$-$C_6$)alkyl, carboxyl and $NR^{20}R^{21}$;
wherein said compound contains at least one linking group;
wherein said compound has at least one —$NR^{20}R^{21}$ group substituted on an aromatic ring; and
wherein said compound is essentially non-fluorescent and is charge neutral.

9. The compound of claim 8, wherein at least one of $R^{9b}$, $R^{9d}$, $R^{10b}$ and $R^{10d}$ on formula Id is a —$NR^{20}R^{21}$ group.

10. The compound of claim 1, 6 or 8, wherein A is halogen; $R^1$ and $R^2$ together with the

group to which they are bonded form a 5- to 7-membered ring; and a and b are each 1.

11. The compound of claim 1, 6 or 8 wherein A is halogen.

12. The compound of claim 1, 6 or 8, wherein A is a substituted aryloxy group, wherein $R^{36a}$, $R^{36b}$, $R^{36d}$ and $R^{36e}$ are each hydrogen, and $R^{36c}$ is —$SO_3Cat$, wherein Cat is a sodium or potassium cation.

13. The compound of claim 1, 6 or 8, wherein A is hydrogen; $R^1$ and $R^2$ are both hydrogen;
a is 0 or 1; and
b is 0 or 1.
14. The compound of claim 1, wherein $R^7$ is —$(CH_2)_dR^{15}$, wherein d is an integer from 1-10, and wherein $R^{15}$ is a N-hydroxy succinimidyl ester, a sulfo N-hydroxysuccinimidyl ester or a maleimide.
15. A compound, wherein said compound is selected from the group consisting of:
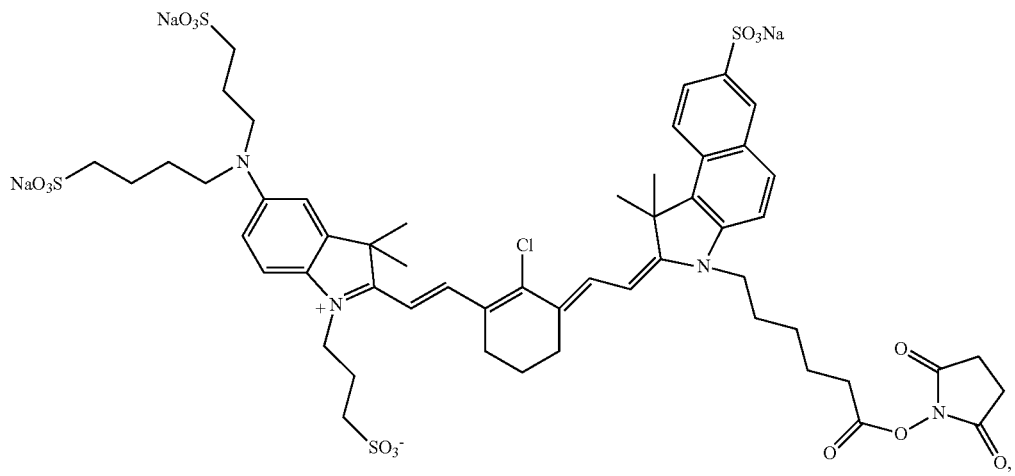
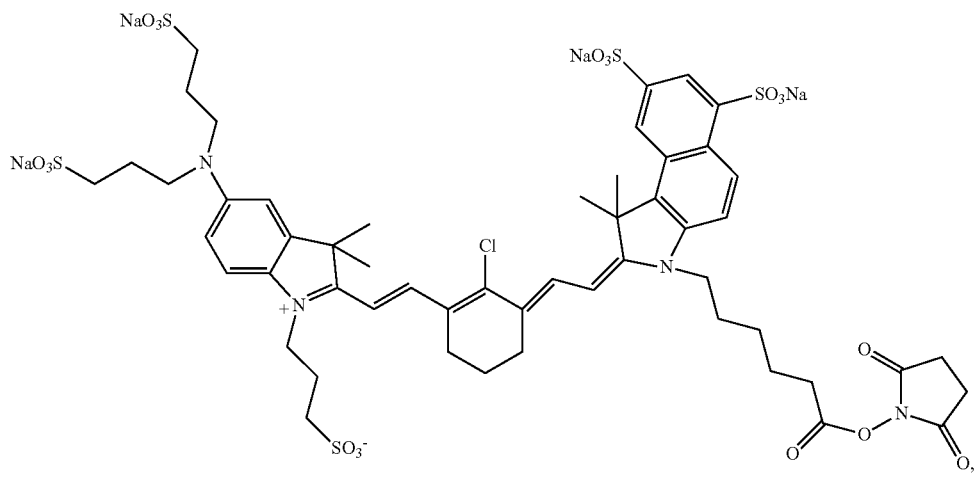
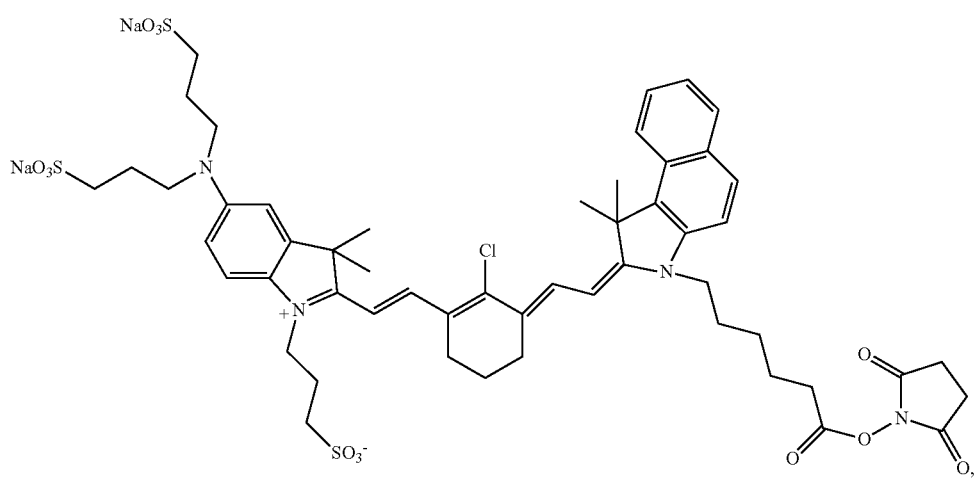

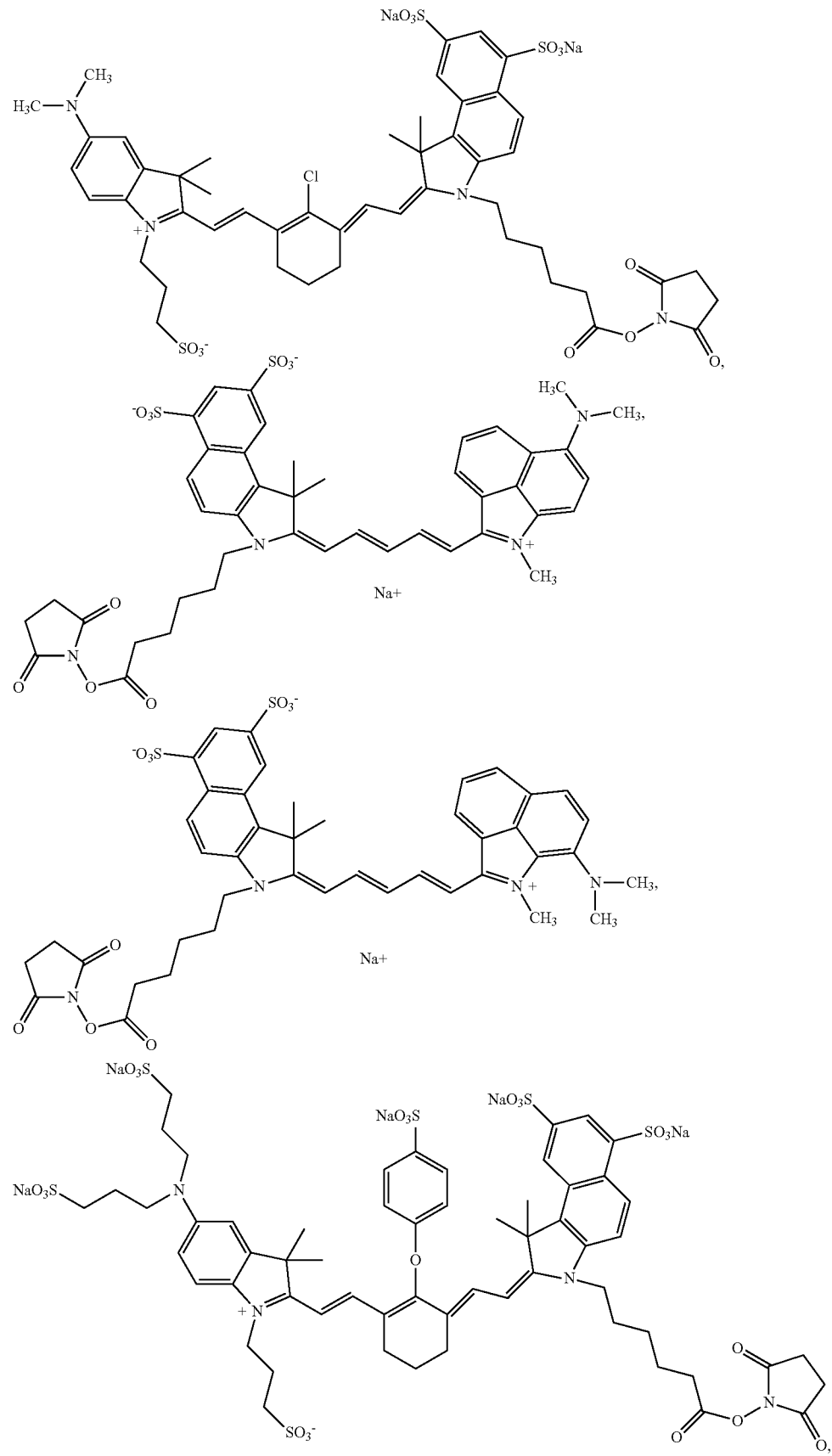

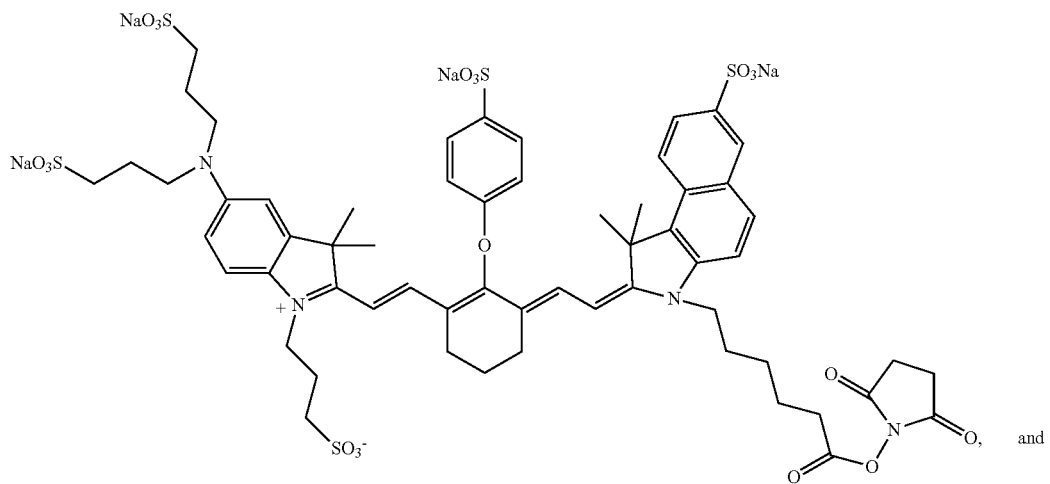
and
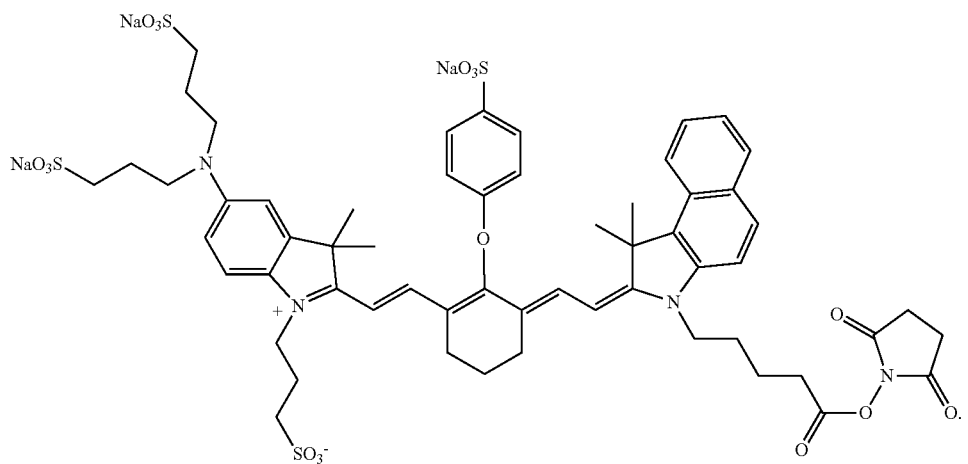
16. A compound, wherein said compound is selected from the group consisting of:
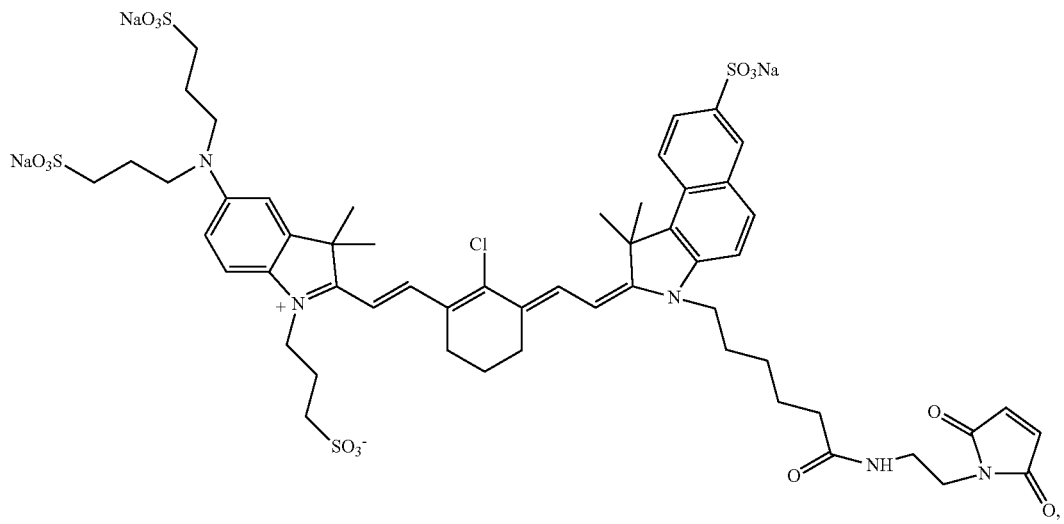

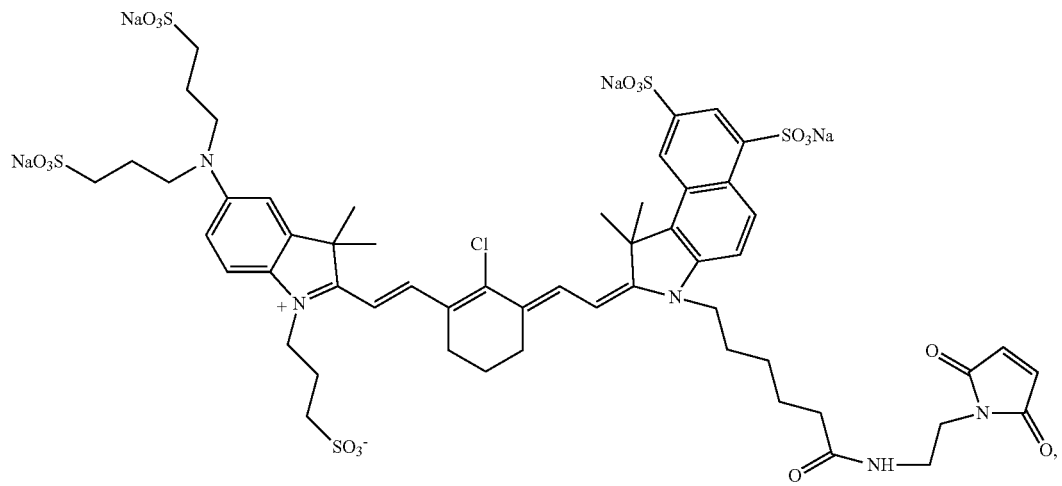
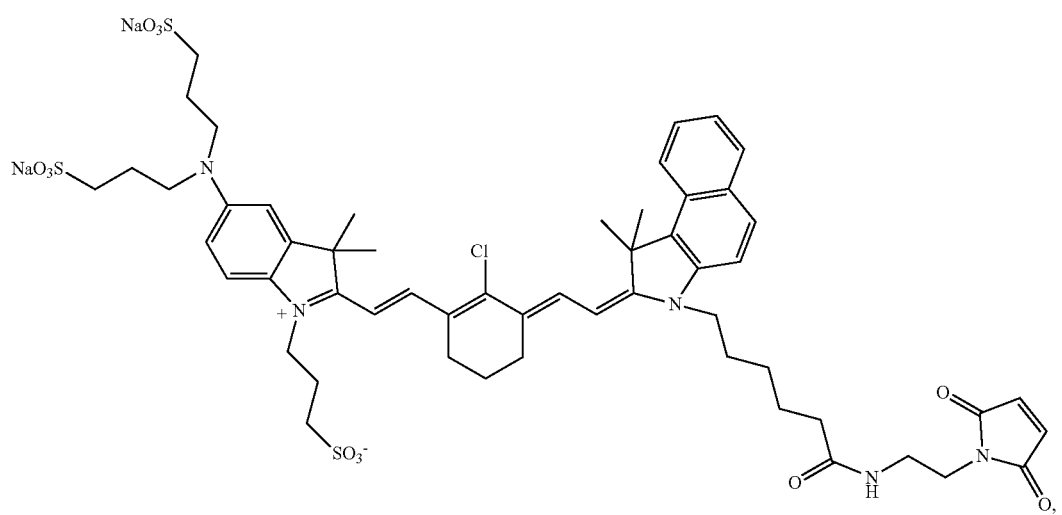
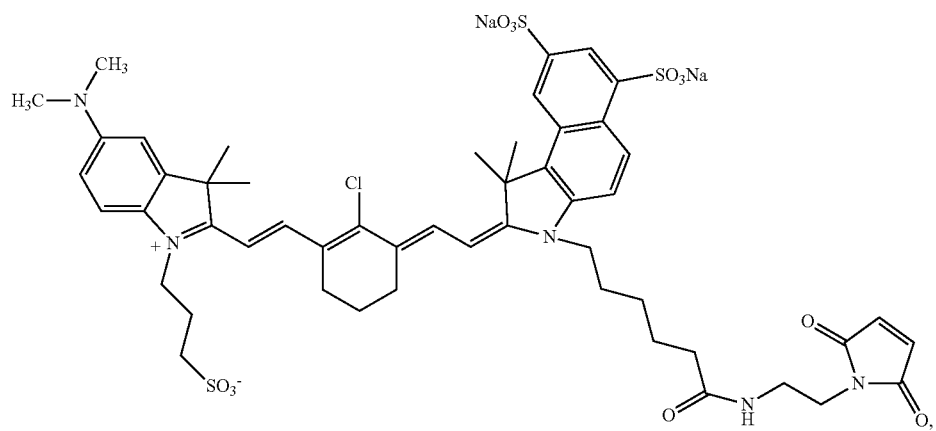

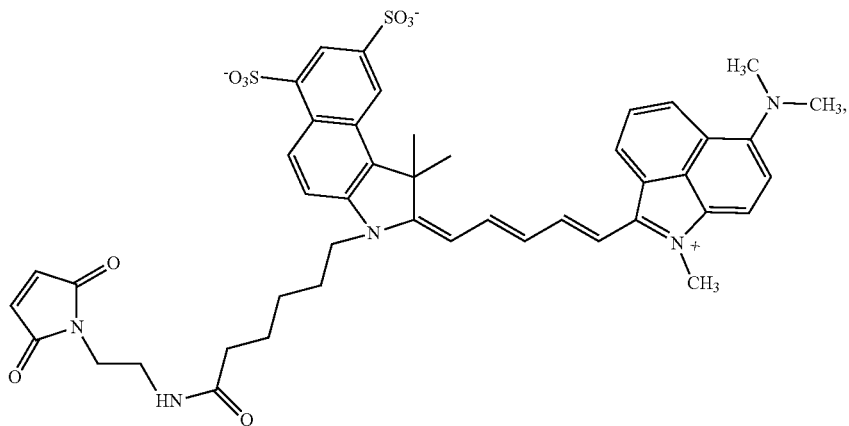
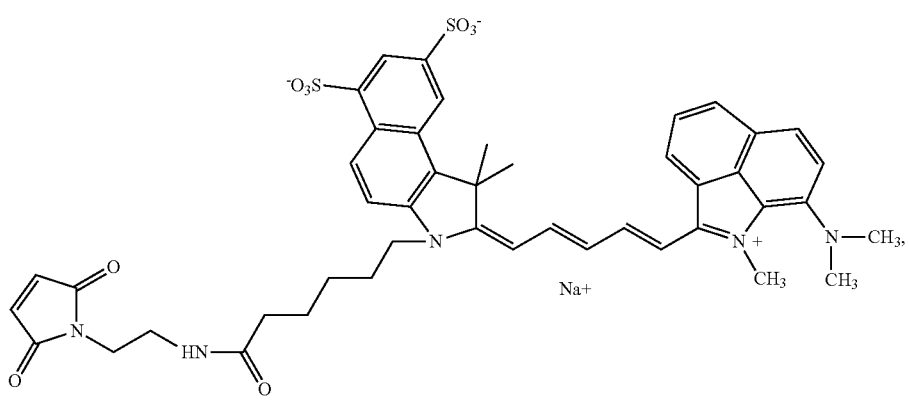
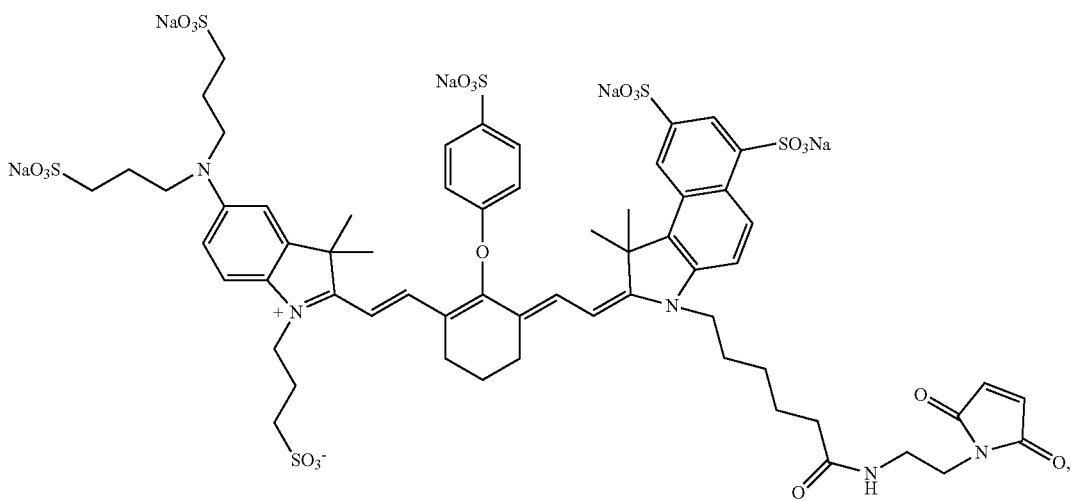

-continued
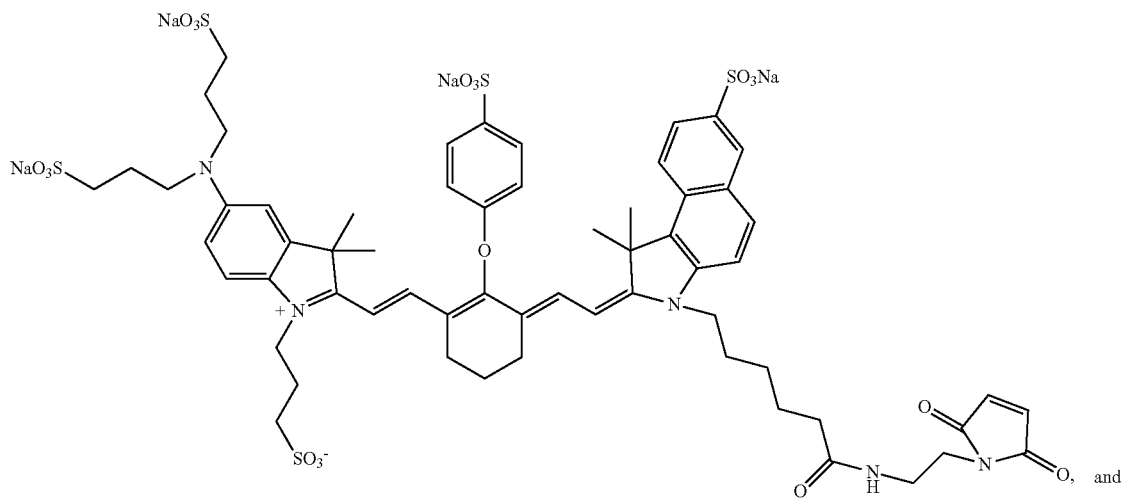
, and
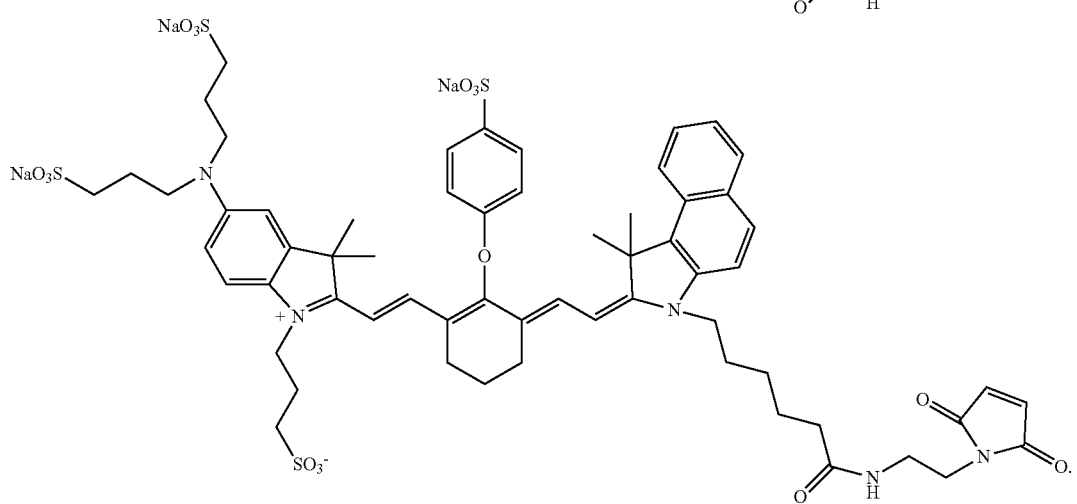
17. A compound having the formula:
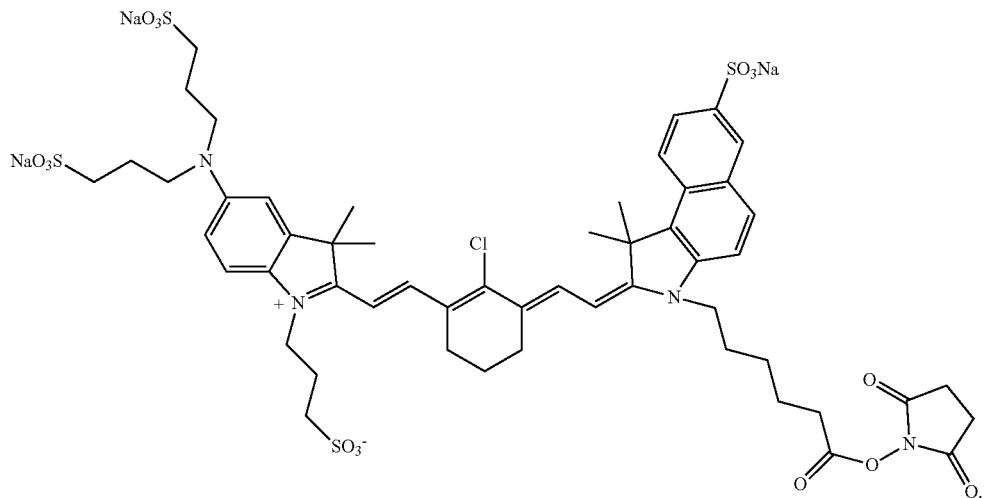
* * * * *

UNITED STATES PATENT AND TRADEMARK OFFICE
CERTIFICATE OF CORRECTION

PATENT NO. : 8,227,621 B2  Page 1 of 1
APPLICATION NO. : 11/423675
DATED : July 24, 2012
INVENTOR(S) : Xinzhan Peng et al.

It is certified that error appears in the above-identified patent and that said Letters Patent is hereby corrected as shown below:

(75)    Inventors should read: Xinzhan Peng, Lincoln, NE (US); Xinshe Xu, Lincoln, NE (US); Daniel R. Draney, Lincoln, NE (US); Garrick M. Little, Lincoln, NE (US)

Signed and Sealed this
Twentieth Day of November, 2012

David J. Kappos
*Director of the United States Patent and Trademark Office*

SEQUENCE LISTING

```
<160> NUMBER OF SEQ ID NOS: 15

<210> SEQ ID NO 1
<211> LENGTH: 11
<212> TYPE: PRT
<213> ORGANISM: Artificial Sequence
<220> FEATURE:
<223> OTHER INFORMATION: reporter-quencher conjugated HIV-1 protease
      substrate structure III
<220> FEATURE:
<221> NAME/KEY: MOD_RES
<222> LOCATION: (1)...(1)
<223> OTHER INFORMATION: Xaa = Val conjugated to near infrared (NIR)
      fluorescent donor Reporter Dye A via Val N-terminal amino group
<220> FEATURE:
<221> NAME/KEY: MOD_RES
<222> LOCATION: (11)...(11)
<223> OTHER INFORMATION: Xaa = Lys conjugated to essentially
      non-fluorescent (ENF) dark quencher cyanine dye Compound 6 via Lys
      side-chain amino group

<400> SEQUENCE: 1

Xaa Ser Gln Asn Tyr Pro Ile Val Gln Asn Xaa
1               5                   10

<210> SEQ ID NO 2
<211> LENGTH: 5
<212> TYPE: PRT
<213> ORGANISM: Artificial Sequence
<220> FEATURE:
<223> OTHER INFORMATION: reporter cleavage product of reporter-quencher
      conjugated HIV-1 protease substrate
<220> FEATURE:
<221> NAME/KEY: MOD_RES
<222> LOCATION: (1)...(1)
<223> OTHER INFORMATION: Xaa = Val conjugated to near infrared (NIR)
      fluorescent donor Reporter Dye A via Val N-terminal amino group

<400> SEQUENCE: 2

Xaa Ser Gln Asn Tyr
1               5

<210> SEQ ID NO 3
<211> LENGTH: 6
```

```
<212> TYPE: PRT
<213> ORGANISM: Artificial Sequence
<220> FEATURE:
<223> OTHER INFORMATION: quencher cleavage product of reporter-quencher
      conjugated HIV-1 protease substrate
<220> FEATURE:
<221> NAME/KEY: MOD_RES
<222> LOCATION: (6)...(6)
<223> OTHER INFORMATION: Xaa = Lys conjugated to essentially
      non-fluorescent (ENF) dark quencher cyanine dye Compound 6 via Lys
      side-chain amino group

<400> SEQUENCE: 3

Pro Ile Val Gln Asn Xaa
 1               5

<210> SEQ ID NO 4
<211> LENGTH: 11
<212> TYPE: PRT
<213> ORGANISM: Artificial Sequence
<220> FEATURE:
<223> OTHER INFORMATION: HIV-1 protease substrate derived from natural
      cleavage site at junction of matrix protein (MA)
      and capsid protein (CA) in HIV-1 gag polyprotein

<400> SEQUENCE: 4

Val Ser Gln Asn Tyr Pro Ile Val Gln Asn Lys
 1               5                  10

<210> SEQ ID NO 5
<211> LENGTH: 13
<212> TYPE: PRT
<213> ORGANISM: Artificial Sequence
<220> FEATURE:
<223> OTHER INFORMATION: reporter-quencher conjugated beta-secretase
      (beta-amyloid converting enzyme (BACE-1)) protease
      substrate structure IV
<220> FEATURE:
<221> NAME/KEY: MOD_RES
<222> LOCATION: (1)...(1)
<223> OTHER INFORMATION: Xaa = Ser conjugated to near infrared (NIR)
      fluorescent donor Reporter Dye A via Ser N-terminal amino group
<220> FEATURE:
<221> NAME/KEY: MOD_RES
<222> LOCATION: (11)...(11)
<223> OTHER INFORMATION: Xaa = Lys conjugated to essentially
      non-fluorescent (ENF) dark quencher cyanine dye Compound 6 via Lys
      side-chain amino group

<400> SEQUENCE: 5

Xaa Glu Val Asn Leu Asp Ala Glu Phe Arg Xaa Arg Arg
 1               5                  10

<210> SEQ ID NO 6
<211> LENGTH: 5
<212> TYPE: PRT
<213> ORGANISM: Artificial Sequence
<220> FEATURE:
<223> OTHER INFORMATION: reporter cleavage product of reporter-quencher
      conjugated beta-secretase (beta-amyloid converting
      enzyme (BACE-1)) protease substrate
<220> FEATURE:
<221> NAME/KEY: MOD_RES
<222> LOCATION: (1)...(1)
<223> OTHER INFORMATION: Xaa = Ser conjugated to near infrared (NIR)
      fluorescent donor Reporter Dye A via Ser N-terminal amino group

<400> SEQUENCE: 6

Xaa Glu Val Asn Leu
 1               5

<210> SEQ ID NO 7
```

```
<211> LENGTH: 8
<212> TYPE: PRT
<213> ORGANISM: Artificial Sequence
<220> FEATURE:
<223> OTHER INFORMATION: quencher cleavage product of reporter-quencher
      conjugated beta-secretase (beta-amyloid converting
      enzyme (BACE-1)) protease substrate
<220> FEATURE:
<221> NAME/KEY: MOD_RES
<222> LOCATION: (6)...(6)
<223> OTHER INFORMATION: Xaa = Lys conjugated to essentially
      non-fluorescent (ENF) dark quencher cyanine dye Compound 6 via Lys
      side-chain amino group

<400> SEQUENCE: 7

Asp Ala Glu Phe Arg Xaa Arg Arg
1               5

<210> SEQ ID NO 8
<211> LENGTH: 13
<212> TYPE: PRT
<213> ORGANISM: Artificial Sequence
<220> FEATURE:
<223> OTHER INFORMATION: reporter-quencher conjugated beta-secretase
      (beta-amyloid converting enzyme (BACE-1)) protease
      substrate TGA resin-tethered peptide synthesis
      precursor
<220> FEATURE:
<221> NAME/KEY: MOD_RES
<222> LOCATION: (1)...(1)
<223> OTHER INFORMATION: Xaa = tert-butyl Ser
<220> FEATURE:
<221> NAME/KEY: MOD_RES
<222> LOCATION: (2)...(2)
<223> OTHER INFORMATION: Xaa = Glu tert butyl ester
<220> FEATURE:
<221> NAME/KEY: MOD_RES
<222> LOCATION: (4)...(4)
<223> OTHER INFORMATION: Xaa = trityl Asn
<220> FEATURE:
<221> NAME/KEY: MOD_RES
<222> LOCATION: (6)...(6)
<223> OTHER INFORMATION: Xaa = Asp tert butyl ester
<220> FEATURE:
<221> NAME/KEY: MOD_RES
<222> LOCATION: (8)...(8)
<223> OTHER INFORMATION: Xaa = Glu tert butyl ester
<220> FEATURE:
<221> NAME/KEY: MOD_RES
<222> LOCATION: (10)...(10)
<223> OTHER INFORMATION: Xaa = 2,2,4,6,7-pentamethyl
      dihydrobenzofuran-S-sulfonyl Arg
<220> FEATURE:
<221> NAME/KEY: MOD_RES
<222> LOCATION: (11)...(11)
<223> OTHER INFORMATION: Xaa = tert butyl carbonyl Lys
<220> FEATURE:
<221> NAME/KEY: MOD_RES
<222> LOCATION: (12)...(12)
<223> OTHER INFORMATION: Xaa = 2,2,4,6,7-pentamethyl
      dihydrobenzofuran-S-sulfonyl Arg
<220> FEATURE:
<221> NAME/KEY: MOD_RES
<222> LOCATION: (13)...(13)
<223> OTHER INFORMATION: Xaa = 2,2,4,6,7-pentamethyl
      dihydrobenzofuran-S-sulfonyl Arg conjugated to TGA
      resin

<400> SEQUENCE: 8

Xaa Xaa Val Xaa Leu Xaa Ala Xaa Phe Xaa Xaa Xaa Xaa
1               5                   10

<210> SEQ ID NO 9
<211> LENGTH: 13
<212> TYPE: PRT
<213> ORGANISM: Artificial Sequence
```

-continued

```
<220> FEATURE:
<223> OTHER INFORMATION: reporter-quencher conjugated beta-secretase
      (beta-amyloid converting enzyme (BACE-1)) protease
      substrate TGA resin-tethered peptide synthesis
      precursor
<220> FEATURE:
<221> NAME/KEY: MOD_RES
<222> LOCATION: (1)...(1)
<223> OTHER INFORMATION: Xaa = tert-butyl Ser conjugated to near
      infrared (NIR) fluorescent donor Reporter Dye A
<220> FEATURE:
<221> NAME/KEY: MOD_RES
<222> LOCATION: (2)...(2)
<223> OTHER INFORMATION: Xaa = Glu tert butyl ester
<220> FEATURE:
<221> NAME/KEY: MOD_RES
<222> LOCATION: (4)...(4)
<223> OTHER INFORMATION: Xaa = trityl Asn
<220> FEATURE:
<221> NAME/KEY: MOD_RES
<222> LOCATION: (6)...(6)
<223> OTHER INFORMATION: Xaa = Asp tert butyl ester
<220> FEATURE:
<221> NAME/KEY: MOD_RES
<222> LOCATION: (8)...(8)
<223> OTHER INFORMATION: Xaa = Glu tert butyl ester
<220> FEATURE:
<221> NAME/KEY: MOD_RES
<222> LOCATION: (10)...(10)
<223> OTHER INFORMATION: Xaa = 2,2,4,6,7-pentamethyl
      dihydrobenzofuran-S-sulfonyl Arg
<220> FEATURE:
<221> NAME/KEY: MOD_RES
<222> LOCATION: (11)...(11)
<223> OTHER INFORMATION: Xaa = tert butyl carbonyl Lys
<220> FEATURE:
<221> NAME/KEY: MOD_RES
<222> LOCATION: (12)...(12)
<223> OTHER INFORMATION: Xaa = 2,2,4,6,7-pentamethyl
      dihydrobenzofuran-S-sulfonyl Arg
<220> FEATURE:
<221> NAME/KEY: MOD_RES
<222> LOCATION: (13)...(13)
<223> OTHER INFORMATION: Xaa = 2,2,4,6,7-pentamethyl
      dihydrobenzofuran-S-sulfonyl Arg conjugated to TGA
      resin

<400> SEQUENCE: 9

Xaa Xaa Val Xaa Leu Xaa Ala Xaa Phe Xaa Xaa Xaa Xaa
 1               5                  10

<210> SEQ ID NO 10
<211> LENGTH: 13
<212> TYPE: PRT
<213> ORGANISM: Artificial Sequence
<220> FEATURE:
<223> OTHER INFORMATION: reporter-quencher conjugated beta-secretase
      (beta-amyloid converting enzyme (BACE-1)) protease
      substrate TGA resin-tethered peptide synthesis
      precursor
<220> FEATURE:
<221> NAME/KEY: MOD_RES
<222> LOCATION: (1)...(1)
<223> OTHER INFORMATION: Xaa = tert-butyl Ser conjugated to near
      infrared (NIR) fluorescent donor Reporter Dye A

<400> SEQUENCE: 10

Xaa Glu Val Asn Leu Asp Ala Glu Phe Arg Lys Arg Arg
 1               5                  10

<210> SEQ ID NO 11
<211> LENGTH: 9
<212> TYPE: PRT
<213> ORGANISM: Artificial Sequence
<220> FEATURE:
<223> OTHER INFORMATION: statine-derived peptide inhibitor of
```

```
      beta-secretase (beta-amyloid converting enzyme
      (BACE-1))
<220> FEATURE:
<221> NAME/KEY: MOD_RES
<222> LOCATION: (4)...(5)
<223> OTHER INFORMATION: Xaa at positions 4 and 5 is dipeptide analog
      statine ((3S,4S)-4-amino-3-hydroxy-6-methylheptanoic acid)
<220> FEATURE:
<221> NAME/KEY: MOD_RES
<222> LOCATION: (9)...(9)
<223> OTHER INFORMATION: Xaa = phenylalaninamide

<400> SEQUENCE: 11

Glu Val Asn Xaa Xaa Val Ala Glu Xaa
1               5

<210> SEQ ID NO 12
<211> LENGTH: 13
<212> TYPE: PRT
<213> ORGANISM: Artificial Sequence
<220> FEATURE:
<223> OTHER INFORMATION: beta-secretase (beta-amyloid converting enzyme
      (BACE-1)) peptide substrate

<400> SEQUENCE: 12

Ser Glu Val Asn Leu Asp Ala Glu Phe Arg Lys Arg Arg
1               5                   10

<210> SEQ ID NO 13
<211> LENGTH: 11
<212> TYPE: PRT
<213> ORGANISM: Artificial Sequence
<220> FEATURE:
<223> OTHER INFORMATION: reporter-quencher conjugated HIV-1 protease
      substrate peptide synthesis presursor
<220> FEATURE:
<221> NAME/KEY: MOD_RES
<222> LOCATION: (1)...(1)
<223> OTHER INFORMATION: Xaa = Val conjugated to near infrared (NIR)
      fluorescent donor Reporter Dye A via Val N-terminal amino group

<400> SEQUENCE: 13

Xaa Ser Gln Asn Tyr Pro Ile Val Gln Asn Lys
1               5                   10

<210> SEQ ID NO 14
<211> LENGTH: 13
<212> TYPE: PRT
<213> ORGANISM: Artificial Sequence
<220> FEATURE:
<223> OTHER INFORMATION: phosphorylated Src peptide 521-533
<220> FEATURE:
<221> NAME/KEY: MOD_RES
<222> LOCATION: (7)...(7)
<223> OTHER INFORMATION: Xaa = phosphotyrosine

<400> SEQUENCE: 14

Thr Ser Thr Glu Pro Gln Xaa Gln Pro Gly Glu Asn Leu
1               5                   10

<210> SEQ ID NO 15
<211> LENGTH: 13
<212> TYPE: PRT
<213> ORGANISM: Artificial Sequence
<220> FEATURE:
<223> OTHER INFORMATION: control non-phosphorylated Src peptide 521-533

<400> SEQUENCE: 15

Thr Ser Thr Glu Pro Gln Tyr Gln Pro Gly Glu Asn Leu
1               5                   10
```